US012016860B2

(12) United States Patent
Guiducci et al.

(10) Patent No.: US 12,016,860 B2
(45) Date of Patent: Jun. 25, 2024

(54) COMBINATION THERAPIES WITH CBL-B INHIBITOR COMPOUNDS

(71) Applicant: Nurix Therapeutics, Inc., San Francisco, CA (US)

(72) Inventors: Cristiana Guiducci, San Francisco, CA (US); Marilena Gallotta, San Francisco, CA (US)

(73) Assignee: NURIX THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 17/716,982

(22) Filed: Apr. 8, 2022

(65) Prior Publication Data

US 2022/0339152 A1  Oct. 27, 2022

Related U.S. Application Data

(60) Provisional application No. 63/290,619, filed on Dec. 16, 2021, provisional application No. 63/277,122, (Continued)

(51) Int. Cl.
*A61K 31/502* (2006.01)
*A61K 31/337* (2006.01)
(Continued)

(52) U.S. Cl.
CPC .......... *A61K 31/502* (2013.01); *A61K 31/337* (2013.01); *A61K 31/454* (2013.01);
(Continued)

(58) Field of Classification Search
CPC .......... A61K 2039/505; A61K 2300/00; A61K 31/337; A61K 31/4196; A61K 31/454; A61K 31/502; A61K 31/5025; A61K 39/39541; A61K 39/39558; A61K 45/06; A61P 35/00; A61P 35/02; C07K 16/2803; C07K 16/2818; C07K 16/2887; C07K 2317/24; C07K 2317/31; C07K 2317/622;
(Continued)

(56) References Cited

U.S. PATENT DOCUMENTS 5,273,986 A  12/1993 Holland et al.
11,401,267 B2  8/2022 Sands et al.
(Continued)

FOREIGN PATENT DOCUMENTS

CN  101918544 A  12/2010
CN  103898051 A  7/2014
(Continued)

OTHER PUBLICATIONS

International Search Report and Written Opinion for International Patent Application PCT/US2019/015250, 10 pages, dated Jun. 11, 2019.
(Continued)

*Primary Examiner* — Savitha M Rao
(74) *Attorney, Agent, or Firm* — Squire Patton Boggs (US) LLP

(57) ABSTRACT

The present disclosure relates to combination therapies with Cbl-b inhibitor compounds, and compositions and kits comprising combinations with the Cbl-b compounds. Also provided are methods of using the combinations with Cbl-b compounds and compositions thereof, such as in therapeutic methods.

4 Claims, 17 Drawing Sheets

Related U.S. Application Data filed on Nov. 8, 2021, provisional application No. 63/172,644, filed on Apr. 8, 2021.

(51) Int. Cl.
A61K 31/454 (2006.01)
A61K 31/5025 (2006.01)
A61P 35/00 (2006.01)
C07K 16/28 (2006.01)
C12N 5/0783 (2010.01)

(52) U.S. Cl.
CPC .......... *A61K 31/5025* (2013.01); *A61P 35/00* (2018.01); *C07K 16/2887* (2013.01); *C12N 5/0646* (2013.01); *C07K 2317/24* (2013.01); *C07K 2317/31* (2013.01); *C07K 2317/622* (2013.01); *C07K 2317/76* (2013.01); *C07K 2319/74* (2013.01)

(58) Field of Classification Search
CPC .......... C07K 2317/732; C07K 2317/76; C07K 2319/74; C12N 5/0646
See application file for complete search history.

(56) References Cited

U.S. PATENT DOCUMENTS

| | | |
|---|---|---|
| 11,464,802 B2 | 10/2022 | Sands et al. |
| 11,530,229 B2 | 12/2022 | Sands et al. |
| 2007/0054355 A1 | 3/2007 | Reiss et al. |
| 2014/0010781 A1 | 1/2014 | Lametschwandtner et al. |
| 2017/0015655 A1 | 1/2017 | Kaieda et al. |
| 2020/0323904 A1 | 10/2020 | Sands et al. |
| 2021/0053961 A1 | 2/2021 | Sands et al. |
| 2021/0053986 A1 | 2/2021 | Sands et al. |
| 2021/0085717 A1 | 3/2021 | Gosling et al. |
| 2021/0087259 A1 | 3/2021 | Gosling et al. |
| 2021/0198280 A1 | 7/2021 | Kelly et al. |
| 2022/0324835 A1 | 10/2022 | Barsanti et al. |
| 2022/0339152 A1 | 10/2022 | Guiducci et al. |
| 2022/0378839 A1 | 12/2022 | Sands et al. |
| 2022/0387395 A1 | 12/2022 | Sands et al. |
| 2023/0086137 A1 | 3/2023 | Somanath et al. |
| 2023/0355599 A1 | 11/2023 | Powers et al. |
| 2023/0414598 A1 | 12/2023 | Brown et al. |

FOREIGN PATENT DOCUMENTS

| | | |
|---|---|---|
| EP | 1 364 949 A1 | 11/2003 |
| EP | 3 254 701 A1 | 12/2017 |
| WO | WO 1986/05779 A1 | 10/1986 |
| WO | WO 2005/021532 A1 | 3/2005 |
| WO | WO 2005/080367 A1 | 9/2005 |
| WO | WO 2007/072225 A2 | 6/2007 |
| WO | WO 2008/033403 A2 | 3/2008 |
| WO | WO 2009/073905 A2 | 6/2009 |
| WO | WO 2009/098144 A1 | 8/2009 |
| WO | WO 2011/076725 A1 | 6/2011 |
| WO | WO 2011/140488 A1 | 11/2011 |
| WO | WO 2012/020008 A1 | 2/2012 |
| WO | WO 2012/089736 A1 | 7/2012 |
| WO | WO 2012/175513 A1 | 12/2012 |
| WO | WO 2013/067264 A1 | 5/2013 |
| WO | WO 2013/067274 A1 | 5/2013 |
| WO | WO 2013/106643 A2 | 7/2013 |
| WO | WO 2013/1066543 A2 | 7/2013 |
| WO | WO 2014/040965 A1 | 3/2014 |
| WO | WO 2015/084998 A1 | 6/2015 |
| WO | WO 2016/196776 A2 | 12/2016 |
| WO | WO 2018/098275 A1 | 5/2018 |
| WO | WO 2018/215801 A1 | 11/2018 |
| WO | WO 2019/063748 A1 | 4/2019 |
| WO | WO 2019/148005 A1 | 8/2019 |
| WO | WO 2020/081450 A1 | 4/2020 |
| WO | WO 2020/167518 A1 | 8/2020 |
| WO | WO 2020/210508 A1 | 10/2020 |
| WO | WO 2020/236654 A1 | 11/2020 |
| WO | WO 2020/264398 A1 | 12/2020 |
| WO | WO 2021/021761 A1 | 2/2021 |
| WO | WO 2021/061853 A1 | 4/2021 |
| WO | WO 2021/091575 A1 | 5/2021 |
| WO | WO 2021/113557 A1 | 6/2021 |
| WO | WO 2022/217123 A1 | 10/2022 |
| WO | WO 2023/250097 A1 | 12/2023 |

OTHER PUBLICATIONS

International Search Report and Written Opinion for International Patent Application PCT/US2019/056112, 8 pages, dated Dec. 6, 2019.

International Search Report and Written Opinion for International Patent Application PCT/US2020/016489, 8 pages, dated May 27, 2020.

International Search Report and Written Opinion for International Patent Application PCT/US2020/027492, 21 pages, dated Aug. 11, 2020.

International Search Report and Written Opinion for International Patent Application PCT/US2020/039957, 16 pages, dated Oct. 5, 2020.

International Search Report and Written Opinion for International Patent Application PCT/US2020/033274, 19 pages, dated Oct. 23, 2020.

International Search Report and Written Opinion for International Patent Application PCT/US2019/043788, 13 pages, dated Oct. 23, 2020.

International Search Report and Written Opinion for International Patent Application PCT/US2020/052335, 12 pages, dated Apr. 1, 2021.

International Search Report and Written Opinion for International Patent Application PCT/US2019/060584, pages, dated May 14, 2021.

Extended European Search Report for European Patent Application No. 19744118.1, 12 pages dated Sep. 22, 2021.

Riling et al.: "Abstract A206: Small-molecule Cbl-b inhibitors as novel intracellular checkpoint inhibitors for cancer immunotherapy | Molecular Cancer Therapeutics", Jan. 1, 2018 (Jan. 1, 2018), XP055700949, Retrieved from the Internet:URL:https:// mct.aacrjournals.org/content/17/1_Supplement/A206 [retrieved on Jun. 4, 2020].

Gosling et al.: "Abstract 2696: Genetic and pharmacologic evaluation of the ubiquitin ligase CBL-B as a small-molecule, tumor immunotherapy target | Cancer Research", Apr. 3, 2019 (Apr. 3, 2019), XP055701108, Retrieved from the Internet:URL:https:// cancerres.aacrjournals.org/content/79/13_Supplement/2696 [retrieved on Jun. 4, 2020].

Marelli et al., Tumor targeting via integrin ligands, Frontiers in Oncology, vol. 3, Article 222, pp. 1-12, 2013.

Wang et al., Mathematical modeling in cancer drug discovery, Drug Discovery Today, vol. 19, No. 2, pp. 145-150, 2014.

Pearce et al., "Failure modes in anticancer drug discovery and development", Cancer Drug Design and Discovery Edited by Stephen Neidle, Chapter 18, pp. 424-435 (2008).

Johnson et al., "Relationships between drug activity in NCI preclinical in vitro and in vivo models and early clinical trials", British Journal of Cancer (2001) 64(10): 1424-1431.

Tigno-Aranjuez et al., "Inhibition of RIP2's tyrosine kinase activity limits NOD2-driven cytokine responses", Genes & Development, 2010, 24:2666-2677; http://www.genesdev.org/cgi/doi/10.1101/gad.964410.

International Search Report and Written Opinion for International Patent Application PCT/US2022/049171, 14 pages, dated Mar. 16, 2023.

Ray et al., "A novel TLR-9 agonist C792 inhibits plasmacytoid dendritic cell-induced myeloma cell growth and enhance cytotoxicity of bortexomib", Leukemia, Nature Publishing Group UK, London, vol. 28, No. 8 Jan. 30, 2014, pp. 1716-1724. DOI:10.1038/LEU.2014.46.

(56) References Cited

OTHER PUBLICATIONS

International Search Report and Written Opinion for International Patent Application PCT/US2020/024119, 19 19 pages, dated Jan. 5, 2023.
International Search Report and Written Opinion for International Patent Application PCT/US2022/049171, 11 pages, dated Mar. 16, 2023.
Acute Leukemia, Merck Manual (Online Edition) 6 pages, pp. 1-6 (2013).
Gura, T. "Systems for Identifying New Drugs Are Often Faulty," Cancer Models, Science, vol. 278, No. 5340, pp. 1041-1042, Nov. 1997.
Jack, J. et al., "Gene Expression and Linkage Analysis Implicate CBLB as a Mediator of Rituximab Reistsance," The Pharmacogenomics Journal (2018) 18: 467-473.
Ray, A. et al., "A novel TLR-9 agonist C792 inhibits plasmacytoid dendritic cell-induced myeloma cell growth and enhance cytotoxicity of bortexomib," Leukemia, Nature Publishing Group UK, London, vol. 28, No. 8 Jan. 30, 2014, pp. 1716-1724. DOI:10.1038/LEU.2014.46.
Simone, Oncology: Introduction, Cecil Textbook of Medicine, 20th Edition, vol. 1, pp. 1004-1010, 1996.
Sitaram, P. et al., "Beyond the Cell Surface: Targeting Intracellular Negative Regulators to Enhance T cell Anti-Tumor Activity," International Journal of Molecular Sciences, 20, 5821, 28 pages (2019).
Augustin et al., "Targeting cbl-b in cancer immunotherapy", Journal for Immunotherapy of Cancer (2023) 11(2): pp. 1-17.
Bachmaier K et al: "Negative regulation of lymphocyte activation and autoimmunity by the molecular adaptor Cbl-b", Nature, Nature Publishing Group UK, London, vol. 403, No. 6766, Jan. 13, 2000 (Jan. 13, 2000), pp. 211-216, XP002575145, ISSN: 0028-0836, DOI: 10.1038/35003228 the whole document abstract.
Chimera L. et al: "c-Cbl: An Important Regulator and a Target in Angiogenesis and Tumorigenesis", Cells, vol. 8, No. 5, May 23, 2019 (May 23, 2019), p. 498, XP93071522, DOI: 10.3390/cells8050498 the whole document figure 3.
Lupher et al: "Cbl-mediated negative regulation of the Syk tyrosine kinase. A critical role for Cbl phosphotyrosine-binding domain binding to Syk phosphotyrosine 323", The Journal of biological chemistry, Dec. 25, 1998 (Dec. 25, 1998), pp. 35273-35281, XP93071643, United States DOI:10.1074/jbc.273.52.35273.
Lyle et al., "c-CBL: An Important Regulator and a Taregt in Angiogenesis and Tumorigenesis" Cells Review 2019, 8, 498; doi:10.3390/cells8050498.
Ota Y et al: "The Product of the Proto-Oncogene c-cbl: A Negative Regulator of the Syk Tyrosine Kinase", Science Apr. 18, 1997;276(5311):418-20, Jan. 1, 1997(Jan. 1, 1997), XP93071617, Retrieved from the Internet:URL:https://www.science.org/doi/pdf/10.112 6/science.276.5311.418 [retrieved on Aug. 8, 2023] the whole document, p. 419,col. 2.
Ota Y et al: "Characterization of Cbl tyrosine phosphorylation and a Cbl-Syk complex in RBL-2H3 cells.", Journal of Experimental Medicine, vol. 184, No. 5, Nov. 1, 1996 (Nov. 1, 1996), pp. 1713-1723, XP93071596 ISSN: 0022-1007, DOI 10.1084/Jem.184.5.1713.
STN International Search—Stereochemistry searched—Performed by Examiner in U.S. Appl. No. 16/964,979 (Final OA dated Oct. 23, 2023).
Stewart et al., "Efforts toward elucidating Thalidomide's molecular target: an expedient synthesis of the first Thalidomide biotin analogue", Org. Biomol. Chem., 2010, 8:4059-4062.
Synergies LLC: Antiemetics Review, Feb. 17, 200, pp. 1-15 Retrieved from Internet:URL:https://medicaid.nv.gov/downloads/provided/NVRx_DCR_20090625_Antiemetics.pdf [Retrieved from Internet Aug. 31, 2023].

Effect of Compound 23 Treatment on Long Term Survival of Mice in the 4T1, Syngeneic Triple Negative Mammary Carcinoma Model Effect of Compound 23 Treatment on Immune Cell infiltration in CT26 Tumor Tissue after 4 or 19 Doses of Compound 23

Effect of Compound 23 Treatment on Gene Expression Immune Related Pathway Scores in CT26 Tumor Tissue after 4 Doses Effect of Compound 23 Treatment on Gene Expression Immune Related Pathway Scores in CT26 Tumor Tissue after 19 Doses Combination of Compound 23 and Anti-PD-1 synergize to Enhance anti-tumor effects and survival of mice with CT26, MC38, or 4T1 tumors Effect of Compound 23 Treatment on CD8+ T cell immune phenotype, both in tumor and blood samples from treated 4T1-tumor-bearing mice:

Effect of Compound 23 Treatment on the density and phenotype of tumor-infiltrating leukocytes from treated CT26-tumor-bearing mice:

Antitumor activity of compound 23 strongly correlates with increased level of circulating T and NK cells, CD8+ T cells and activated CD8+ T cells and decreased level of circulating myeloid cells (CD11b+) in the blood of treated CT26-tumor-bearing mice:

A)

B)

COMBINATION THERAPIES WITH CBL-B INHIBITOR COMPOUNDS

CROSS-REFERENCE TO RELATED APPLICATIONS

This application claims the benefit of U.S. Provisional Application No. 63/172,644, filed Apr. 8, 2021; U.S. Provisional Application No. 63/277,122, filed Nov. 8, 2021; and U.S. Provisional Application No. 63/290,619, filed Dec. 16, 2021. The contents of each priority patent application are incorporated herein by reference in their entireties for all purposes.

FIELD

Provided herein are combination therapies with Cbl-b inhibitor compounds, compositions for administering the same, including pharmaceutical compositions, and kits for administering the same. The methods and compositions are useful for the treatment and prevention of cell proliferation and cancer.

BACKGROUND

Casitas B-lineage lymphoma proto-oncogene-b (Cbl-b) is an E3 ubiquitin ligase that negatively regulates T-cell activation (Wallner et al., Clin. Dev. Immunol., 2012: 692639). Certain Cbl-b inhibitor compounds have shown promise for several potential immunotherapy applications through enhancing T-cell mediated anti-tumor activity by lowering the activation threshold of T-cells in a suppressive tumor microenvironment where Cbl-b plays a role in the down-regulation of T-cells. Because of the mechanism of Cbl-b inhibitors, they have the potential to enhance, and in certain cases, to synergize the efficacy of another cancer therapeutic. Particularly effective Cbl-b inhibitor combinations include checkpoint inhibitors and agents that trigger NK cell-mediated antibody-dependent cellular cytotoxicity (ADCC).

SUMMARY

Provided herein are Cbl-b inhibitor compounds for use in combination with a second therapeutic agent used to treat cancer. As demonstrated in the Examples herein, combination of a Cbl-b inhibitor compound with the second therapeutic agent yields substantially increased efficacy against solid tumors in an in vivo model. Cbl-b inhibitor compounds are described in detail herein, as are their pharmaceutical compositions, and methods for making them. In particular embodiments, the second therapeutic agent is a checkpoint inhibitor. In particular embodiments, the second therapeutic agent is an agent that triggers NK cell-mediated ADCC.

In one aspect, provide herein are methods of using the Cbl-b inhibitor compounds in combination with a second anti-cancer agent to treat cancer. In certain embodiments, the second anti-cancer agent is a checkpoint inhibitor. In certain other embodiments, the second anti-cancer agent is an agent that triggers NK cell-mediated ADCC.

In another aspect, provided are kits or compositions comprising a Cbl-b inhibitor compound and a second anti-cancer agent. In certain embodiments, the Cbl-b compound and the second anti-cancer agent are in separate pharmaceutical compositions. In certain embodiments, the Cbl-b compound and the second anti-cancer agent are administered separately. In certain embodiments, the Cbl-b compound and the second anti-cancer agent are administered cyclically. In certain embodiments, the compositions are pharmaceutical compositions. Any suitable pharmaceutical composition may be used. In certain embodiments, the pharmaceutical composition for the Cbl-b compound is a composition for oral administration. In certain embodiments, the pharmaceutical composition for the second anti-cancer agent is a composition for parenteral administration. In a particular embodiment, the second anti-cancer agent is a checkpoint inhibitor. In a particular embodiment, the second anti-cancer agent is an agent that triggers NK cell-mediated ADCC.

The methods, kits, and compositions are useful for inhibiting cell proliferation. In certain embodiments, the methods, kits, and compositions are useful for treating cancer.

DETAILED DESCRIPTION OF THE EMBODIMENTS

1. Definitions

Figure 1:
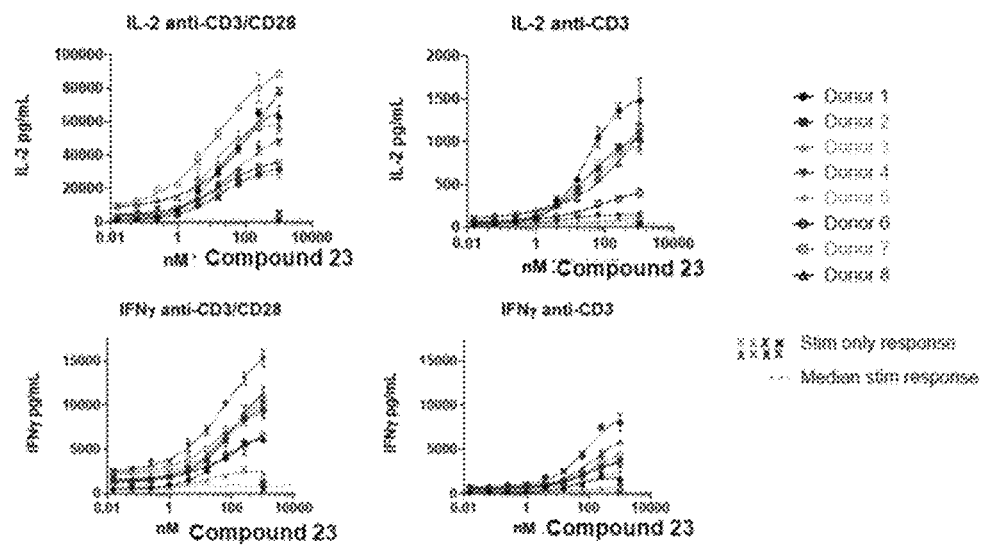
FIG. 1 provides effects of compound 23 on total primary human T-cells.

Unless otherwise defined, all terms of art, notations, and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

It is understood that aspects and embodiments described herein as "comprising" include "consisting of" and "consisting essentially of" embodiments.

As used herein and in the appended claims, the singular forms "a," "an," and "the" include plural referents unless otherwise indicated or clear from context. For example, "an" excipient includes one or more excipients.

Reference to "about" a value, encompasses from 90% to 110% of that value. For instance, about 50 billion cells refers to 45 to 55 billion cells, and includes 50 billion cells. For instance, a temperature of "about 100 degrees" refers to a temperature of about 90 degrees to about 110 degrees.

When numerical ranges of compounds are given, all compounds within those numerical limits designated "a" and "b" are included, unless expressly excluded. For example, reference to compounds 9-13 refers to compounds 9, 10, 11, 12, and 13.

The term "binding antagonist" in reference to a target refers to a molecule that decreases, blocks, inhibits, abrogates or interferes with signal transduction resulting from the interaction of such molecule with the target or with one or more the target's binding partners.

"Cbl-b" as used herein refers to a Cbl-b protein. The term also includes naturally occurring variants of Cbl-b, including splice variants or allelic variants. The term also includes non-naturally occurring variants of Cbl-b, such as a recombinant Cbl-b protein or truncated variants thereof, which generally preserve the binding ability of naturally occurring Cbl-b or naturally occurring variants of Cbl-b (e.g., the ability to bind to an E2 enzyme).

"Cbl-b inhibitor" as used herein refers to a molecule that inhibits the activity of Cbl-b, c-Cbl, or both Cbl-b and c-Cbl proteins.

"c-Cbl" as used herein refers to a c-Cbl protein. The term also includes naturally occurring variants of c-Cbl, including splice variants or allelic variants. The term also includes non-naturally occurring variants of c-Cbl, such as a recombinant c-Cbl protein or truncated variants thereof, which generally preserve the binding ability of naturally occurring c-Cbl or naturally occurring variants of c-Cbl (e.g., the ability to bind to an E2 enzyme).

"CD20" refers to B-lymphocyte antigen CD20 encoded, for example in humans, by the MS4A1 gene. It is known to enable B-cell immune response, for instance to T-independent antigens. Sequences include NM_152866, NM_021950, and NM_152867 (mRNA); and NP_068769, NP_690605, and NP_690606 (protein).

The term "CD20 axis antagonist" refers to a molecule that inhibits the interaction of a CD20 axis binding partner with either one or more of its binding partners.

The term "CD20 binding antagonist" refers to a molecule that decreases, blocks, inhibits, abrogates, or interferes with signal transduction resulting from the interaction of CD20 with its one or more binding partners.

The term "CD47" refers to a surface immunoglobulin that forms a signaling complex with signal-regulatory protein α. In cancer cells, when CD47 forms the signaling complex, it enables the cancer cell to escape from macrophage-mediated phagocytosis. Sequences include NM_001025079, NM_001025080, NM_001777, NM_198793, and NM_001382306 (mRNA); and NP_001768, NP_942088, and NP_001369235 (protein).

The term "CD47 axis antagonist" refers to a molecule that inhibits the interaction of a CD47 axis binding partner with either one or more of its binding partners such as signal-regulatory protein α (SIRP α).

The term "CD47 binding antagonist" refers to a molecule that decreases, blocks, inhibits, abrogates, or interferes with signal transduction resulting from the interaction of CD47 with its one or more binding partners.

The term "checkpoint inhibitor" refers to a compound that impedes the immune checkpoint, a signaling pathway that suppresses the activation of immune cells. Illustrative examples of T-cell checkpoint inhibitors include CTLA-4 axis antagonists, LAG3 binding antagonists, PD-1 axis antagonists, TIGIT binding antagonists, TIM3 binding antagonists, and VISTA binding antagonists. An illustrative example of a macrophage checkpoint inhibitor is a CD47 binding antagonist.

The term "PARP inhibitor" refers to a compound that repairs DNA when the DNA becomes damaged (i.e., blocking poly ADP ribose polymerase (PARP) may prevent cancer cells from repairing damaged cancer cell DNA, thus causing the cancer cells to die). Exemplary PARP inhibitors include olaparib, talazoparib, and niraparib.

The term "taxane" refers to compounds that block cell growth by terminating mitosis (i.e., cell division) via interfering with microtubules. Taxanes can also refer to types of mitotic inhibitors and types of antimicrotubule agents. Exemplary taxanes include paclitaxel and docetaxel.

"CTLA-4" refers to cytotoxic T-lymphocyte associated protein 4. Alternative names or synonyms for CTLA-4 include CD152 (cluster of differentiation 152), ALPS5, CELIAC3, GRD4, GSE, and IDDM12. The mature form of human CLTA-4 amino acid sequence, set forth as residues 36-223 in NCBI Locus No. NP_005205, is incorporated by reference. Further sequences include NM_001037631 and NM_005214 (mRNA) and NP_001032720 (protein).

The term "CTLA-4 axis antagonist" refers to a molecule that inhibits the interaction of a CTLA-4 axis binding partner with either one or more of its binding partners. In certain embodiments, a CTLA-4 axis antagonist removes T-cell dysfunction resulting from signaling on the CTLA-4 signaling axis. In certain embodiments, a CTLA-4 axis antagonist restores or enhances T-cell function (e.g., proliferation, cytokine production, and/or target cell killing). As used herein, CTLA-4 axis antagonist includes CTLA-4 binding antagonists, CD80 binding antagonists, CD86 binding antagonist, and combinations thereof.

The term "CTLA-4 binding antagonist" refers to a molecule that decreases, blocks, inhibits, abrogates, or interferes with signal transduction resulting from the interaction of CTLA-4 with one or more of its binding partners, such as CD80 or CD86. In certain embodiments, the CTLA-4 binding antagonist is ipilimumab. In certain embodiments, the CTLA-4 binding antagonist is tremelimumab.

"Enhancing T-cell function" means to induce, cause, or stimulate a T-cell to have a sustained or amplified biological function, or renew or reactivate exhausted or inactive T-cells. Examples of enhanced T-cell function include increased T-cell activation (e.g., increased cytokine production, increased expression of T-cell activation markers, etc.), increased T-cell proliferation, decreased T-cell exhaustion, and/or decreased T-cell tolerance relative to the state of the T-cells before treatment with a Cbl-b inhibitor compound. Methods of measuring enhancement of T-cell function are known in the art.

"HER2" refers to receptor tyrosine-protein kinase erbB-2. Synonyms include CD340, Neu, Erbb2, ERBB2, and HER2/neu. Sequences include NM_001005862, NM_001289936, NM_001289937, NM_001289938, and NM_004448 (mRNA); and NP_001005862, NP_001276865, NP_001276866, NP_001276867, and NP_004439.

The term "HER2 axis antagonist" refers to a molecule that inhibits the interaction of a HER2 axis binding partner with either one or more of its binding partners.

The term "HER2 binding antagonist" refers to a molecule that decreases, blocks, inhibits, abrogates, or interferes with signal transduction resulting from the interaction of HER2 with one or more of its binding partners. In certain embodiments, the HER2 binding antagonist is trastuzumab. In certain embodiments, the HER2 binding antagonist is pertuzumab.

As used herein, the term "inhibits growth" (e.g. referring to cells, such as tumor cells) is intended to include any measurable decrease in cell growth (e.g., tumor cell growth) when contacted with a compound or combination described herein, as compared to the growth of the same cells not in contact with the same compound or combination. In certain embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

"LAG3" refers to lymphocyte activating gene 3 protein. LAG3 is also known as CD223. The amino acid sequence of the mature form of human LAG3 is set forth as residues 23-525 in NCBI Locus No. NP_002277 which is incorporated by reference. The LAG3 mRNA sequence is set forth in NM_002286, which is incorporated by reference.

The term "LAG3 axis antagonist" refers to a molecule that inhibits the interaction of a LAG3 axis binding partner with either one or more of its binding partners.

The term "LAG3 binding antagonist" refers to a molecule that decreases, blocks, inhibits, abrogates, or interferes with signal transduction resulting from the interaction of LAG3 with its one or more binding partners, such as MHC class II. In certain embodiments the LAG3 binding antagonist is an anti-LAG3 monoclonal antibody.

"Monoclonal antibody" or "mAb" or "Mab," as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731. "PD-1" refers to programmed cell death protein-1. Alternative names or synonyms for PD-1 include PDCD1, PD1, CD279, and SLEB. Human PD-1 amino acid sequences can be found in NCBI Locus No.: NP_005009, incorporated herein by reference in its entirety.

"PD-L1" refers to programmed death-ligand 1. Alternative names for PD-L1 include cluster of differentiation 274 (CD274), B7 homolog 1 (B7-H1), PDCD1L1, PDL1, and B7-4. Human PD-L1 amino acid sequences can be found in NCBI Locus No.: NP_054862, incorporated herein by reference in its entirety.

"PD-L2" refers to programmed cell death ligand 2. Alternative names for PD-L2 include cluster of differentiation 273 (CD273), PDCD1L2, PDL2, B7-DC, and Btdc. Human PD-L1 and PD-L2 amino acid sequences can be found in NCBI Locus No.: NP_079515, incorporated herein by reference in its entirety.

The term "PD-1 axis antagonist" refers to a molecule that inhibits the interaction of a PD-1 axis binding partner with either one or more of its binding partners. In certain embodiments, a PD-1 axis antagonist removes T-cell dysfunction resulting from signaling on the PD-1 signaling axis. In certain embodiments, a PD-1 axis antagonist restores or enhances T-cell function (e.g., proliferation, cytokine production, and/or target cell killing). As used herein, PD-1 axis antagonists include PD-1 binding antagonists, PD-1 binding antagonists, PD-L2 binding antagonist, and combinations thereof.

The term "PD-1 binding antagonist" refers to a molecule that decreases, blocks, inhibits, abrogates, or interferes with signal transduction resulting from the interaction of PD-1 with one or more of its binding partners, such as PD-L1 and/or PD-L2. In certain embodiments, the PD-1 binding antagonist is a molecule that inhibits the binding of PD-1 to one or more of its binding partners. In certain embodiments, the PD-1 binding antagonist inhibits the binding of PD-1 to PD-1 L1 and/or PD-L2. For example, PD-1 binding antagonists include anti-PD-1 antibodies, antigen-1-binding fragments thereof, immunoadhesins, fusion proteins, oligopeptides, and other molecules that decrease, block, inhibit, abrogate, or interfere with signal transduction resulting from the interaction of PD-1 with PD-L1 and/or PD-L2. In certain embodiments, the PD-1 binding antagonist reduces the negative co-stimulatory signal mediated by or through cell surface proteins expressed on T lymphocyte-mediated signaling through PD-1 so as render a dysfunctional T-cell less dysfunctional (e.g., enhancing effector responses to antigen recognition). In certain embodiments, the PD-1 binding antagonist is an anti-PD-1 antibody. In certain embodiments, the PD-11-binding antagonist is pembrolizumab. In certain embodiments, the PD-1 binding antagonist is nivolumab. In certain embodiments, the PD-1 binding antagonist is lambrolizumab. In certain embodiments, the PD-1 binding antagonist is pidilizumab. In certain embodiments, the PD-1 binding antagonist is cemiplimab. In certain embodiments, the PD-1 binding antagonist is AMP-224.

The term "PD-L1 binding antagonist" refers to a molecule that decreases, blocks, inhibits, abrogates, or interferes with signal transduction resulting from the interaction of PD-L1 with either one or more of its binding partners, such as PD-1 and/or CD80. In certain embodiments, the PD-1 binding antagonist is a molecule that inhibits the binding of PD-L1 to its binding partners. In certain embodiments, the PD-L1 binding antagonist inhibits binding of PD-L1 to PD-1 and/or CD80. In certain embodiments, the PD-1 binding antagonists include anti-PD-1 antibodies, antigen-binding fragments thereof, immunoadhesins, fusion proteins, oligopeptides, and other molecules that decrease, block, inhibit, abrogate, or interfere with signal transduction resulting from the interaction of PD-1 with one or more of its binding partners, such as PD-1 and/or CD80. In certain embodiments, the PD-1 binding antagonist reduces the negative co-stimulatory signal mediated by or through cell surface proteins expressed on T lymphocyte-mediated signaling through PD-1 so as to render a dysfunctional T-cell less dysfunctional (e.g., enhancing effector responses to antigen recognition). In certain embodiments, the PD-1 binding antagonist is an anti-PD-1 antibody. In certain embodiments, the PD-1 binding antagonist is atezolizumab. In certain embodiments, the PD-1 binding antagonist is avelumab. In certain embodiments, the PD-PD-1 binding antagonist is durvalumab.

The term "PD-L2 binding antagonist" refers to a molecule that decreases, blocks, inhibits, abrogates, or interferes with signal transduction resulting from the interaction of PD-L2 with either one or more of its binding partners, such as PD-1. In certain embodiments, a PD-L2 binding antagonist is a molecule that inhibits the binding of PD-L2 to one or more of its binding partners. In certain embodiments, the PD-L2 binding antagonist inhibits binding of PD-L2 to PD-1. In certain embodiments, the PD-L2 binding antagonists include anti-PD-L2 antibodies, antigen binding fragments thereof, immunoadhesins, fusion proteins, oligopeptides, and other molecules that decrease, block, inhibit, abrogate, or interfere with signal transduction resulting from the interaction of PD-L2 with either one or more of its binding partners, such as PD-1. In certain embodiments, the PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In certain embodiments, the PD-L2 binding antagonist is an anti-PD-L2 antibody. In certain embodiments, the PD-L2 binding antagonist is an immunoadhesin.

"Proliferation" is used herein to refer to the proliferation of a cell. Increased proliferation encompasses the production of a greater number of cells relative to a baseline value. Decreased proliferation encompasses the production of a reduced number of cells relative to a baseline value. In certain embodiments, the cell is an immune cell such as a T-cell and increased proliferation is desired. In certain embodiments, the cell is a cancer cell and reduced proliferation is desired.

The term "T-cell anergy" refers to the state of unresponsiveness to antigen stimulation resulting from incomplete or insufficient signals delivered through the T-cell receptor. "T-cell anergy" can also result upon stimulation with antigen in the absence of co-stimulation, resulting in the cell becoming refractory to subsequent activation by the antigen even in the context of co-stimulation.

A "T-cell dysfunction disorder" is a disorder or condition characterized by decreased responsiveness of T-cells to antigenic stimulation. Decreased responsiveness may result in ineffective control of a tumor. In certain embodiments, the term "T-cell dysfunction disorder" encompasses cancer such as a hematologic cancer or a non-hematologic cancer. In certain embodiments, a "T-cell dysfunctional disorder" is one in which T-cells are anergic or have decreased ability to secrete cytokines, proliferate, or execute cytolytic activity.

As used herein, the term "T-cell dysfunction" refers to a state of reduced immune responsiveness to antigenic stimulation. The term "T-cell dysfunction" includes common elements of both T-cell exhaustion and/or T-cell anergy in which antigen recognition may occur, but the ensuing immune response is ineffective to control tumor growth. The term "T-cell dysfunction" also includes being refractory or unresponsive to antigen recognition, such as, impaired capacity to translate antigen recognition to downstream T-cell effector functions, such as proliferation, cytokine production, and/or target cell killing.

The term "T-cell exhaustion" refers to a state of T-cell dysfunction that arises from sustained TCR signaling that can occur during cancer. It is distinguished from anergy in that it arises not through incomplete or deficient signaling, but from sustained signaling. It is defined by poor effector function, sustained expression of inhibitory receptors, and a transcriptional state distinct from that of functional effector or memory T-cell.

"TIGIT" refers to T-cell immunoreceptor with Ig and ITIM domains protein. Alternative names or synonyms for TIGIT include VSIG9, V-set and immunoglobulin domain containing 9, VSTM3, V-set and transmembrane domain containing 3, and Washington University cell adhesion molecule (WUCAM). The amino acid sequence of the mature form of human TIGIT is set forth as residues 22-244 in NCBI Locus No.: NP_776160 which is incorporated herein by reference. The mRNA sequence of human TIGIT is set forth in NM_173799, which is incorporated herein by reference.

The term "TIGIT axis antagonist" refers to a molecule that inhibits the interaction of a TIGIT axis binding partner with either one or more of its binding partners.

The term "TIGIT binding antagonist" refers to a molecule that decreases, blocks, inhibits, abrogates, or interferes with signal transduction resulting from the interaction of TIGIT with its one or more binding partners such as CD155 or CD112.

"TIM3" refers to T-cell immunoglobulin and mucin-domain containing-3 protein. Alternative names or synonyms for TIM3 include CD366, HAVCR2, hepatitis A virus cellular receptor 2, KIM3, and SPTCL. The amino acid sequence of the mature form of human TIM3 is set forth as residues 22-301 in NCBI Locus No. NP_116171 which is incorporated herein by reference. The mRNA sequence of human TIM3 is set forth in NM_032782, which is incorporated herein by reference.

The term "TIM3 axis antagonist" refers to a molecule that inhibits the interaction of a TIM3 axis binding partner with either one or more of its binding partners.

The term "TIM3 binding antagonist" refers to a molecule that decreases, blocks, inhibits, abrogates, or interferes with signal transduction resulting from the interaction of TIM3 with its one or more binding partners such as the immunoglobulin V domain.

"VISTA" refers to V-domain Ig suppressor of T-cell activation. Alternative names or synonyms for VISTA include VSIR, V-set immunoregulatory receptor, PD-1H, B7H5, GI24, PP2135, SISP1, and Dies1. The amino acid sequence of the mature form of human VISTA is set forth as residues 33-311 in NCBI Locus No.: NP_071436 which is incorporated herein by reference. The mRNA sequence of human VISTA is set forth in NM_022153, which is incorporated herein by reference.

The term "VISTA axis antagonist" refers to a molecule that inhibits the interaction of a VISTA axis binding partner with either one or more of its binding partners.

The term "VISTA binding antagonist" refers to a molecule that decreases, blocks, inhibits, abrogates, or interferes with signal transduction resulting from the interaction of VISTA with its one or more binding partners.

"Alkyl" as used herein refers to a saturated linear (i.e., unbranched) or branched univalent hydrocarbon chain or combination thereof. Particular alkyl groups are those having a designated number of carbon atoms, for example, an alkyl group having 1 to 20 carbon atoms (a "$C_1$-$C_{20}$ alkyl"), having 1 to 10 carbon atoms (a "$C_1$-$C_{10}$" alkyl), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C═C). Particular alkenyl groups are those having a designated number of carbon atoms, for example, an alkenyl group having 2 to 20 carbon atoms (a "$C_2$-$C_{20}$ alkenyl"), having 2 to 10 carbon atoms (a "$C_2$-$C_{10}$" alkenyl), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). The alkenyl group may be in cis- or trans-configurations or, alternatively, in E- or Z-configurations. Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e., unbranched) or branched univalent hydrocarbon chain or combination thereof, having at least one site of acetylenic unsaturation (i.e., having at least one moiety of the formula C≡C). Particular alkynyl groups are those having a designated number of carbon atoms, for example, an alkynyl group having 2 to 20 carbon atoms (a "$C_2$-$C_{20}$ alkynyl"), having 2 to 10 carbon atoms (a "$C_2$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl groups include, but are not limited to, groups such as ethynyl (or acetylenyl), prop-1-ynyl, prop-2-ynyl (or propargyl), but-1-ynyl, but-2-ynyl, but-3-ynyl, homologs, and isomers thereof, and the like.

"Alkylene" as used herein refers to the same residues as alkyl, but having bivalency, or are divalent. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene"), or 1 to 3 carbon atoms (a "$C_1$-$C_3$ alkylene"). Examples of alkylene groups include, but are not limited to, groups such as methylene (—CH$_2$—), —CH$_2$CH$_2$—, —CH$_2$CH$_2$CH$_2$—, —CH$_2$CH$_2$CH$_2$CH$_2$—, and the like.

"Alkenylene" as used herein refers to the same residues as alkenyl, but having bivalency, or are divalent. Particular alkenylene groups are those having 2 to 6 carbon atoms (a "$C_2$-$C_6$ alkenylene"), 2 to 5 carbon atoms (a "$C_2$-$C_5$ alkenylene"), 2 to 4 carbon atoms (a "$C_2$-$C_4$ alkenylene"), or 2 to 3 carbon atoms (a "$C_2$-$C_3$ alkenylene"). Examples of alkylene groups include, but are not limited to, groups such as —CH═CH—, —CH═CHCH$_2$—, —CH═CHCH$_2$CH$_2$-, and the like.

"Alkynylene" as used herein refers to the same residues as alkynyl, but having bivalency, or are divalent. Particular alkynylene groups are those having 2 to 6 carbon atoms (a "$C_2$-$C_6$ alkynylene"), 2 to 5 carbon atoms (a "$C_2$-$C_5$ alkynylene"), 2 to 4 carbon atoms (a "$C_2$-$C_4$ alkynylene"), or 2 to 3 carbon atoms (a "$C_2$-$C_3$ alkylene"). Examples of alkynylene groups include, but are not limited to, groups such as —CCCH$_2$CH$_2$—, and the like.

"Amino" refers to the group —NH$_2$.

"Aryl" as used herein refers to an aromatic carbocyclic group having a single ring (e.g., phenyl), or multiple condensed rings (e.g., naphthyl or anthryl) where one or more of the condensed rings may not be aromatic. Particular aryl groups are those having from 6 to 14 annular (i.e., ring) carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryls include, but are not limited to, groups such as phenyl, naphthyl, 1-naphthyl, 2-naphthyl, 1,2,3,4-tetrahydronaphthalen-6-yl

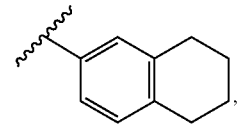

and the like.

"Arylene" as used herein refers to the same residues as aryl, but having bivalency, or are divalent. Particular arylene groups are those having from 6 to 14 annular carbon atoms (a "$_6$-$C_{14}$ arylene"). Examples of arylene include, but are not limited to, groups such as phenylene, o-phenylene (i.e., 1,2-phenylene), m-phenylene (i.e., 1,3-phenylene), p-phenylene (i.e., 1,4-phenylene), naphthylene, 1,2-naphthylene, 1,3-naphthylene, 1,4-naphthylene, 2,7-naphthylene, 2,6-naphthylene, and the like.

"Carbocyclyl" or "carbocyclic" refers to an aromatic or non-aromatic univalent cyclic group in which all of the ring members are carbon atoms, such as cyclohexyl, phenyl, 1,2-dihydronaphthyl, etc.

"Cycloalkyl" as used herein refers to non-aromatic, saturated or unsaturated, cyclic univalent hydrocarbon structures. Particular cycloalkyl groups are those having a designated number of annular (i.e., ring) carbon atoms, for example, a cycloalkyl group having from 3 to 12 annular carbon atoms (a "$C_3$-$C_{12}$ cycloalkyl"). A particular cycloalkyl is a cyclic hydrocarbon having from 3 to 8 annular carbon atoms (a "$C_3$-$C_8$ cycloalkyl"), or having 3 to 6 annular carbon atoms (a "$C_3$-$C_6$ cycloalkyl"). Cycloalkyl can consist of one ring, such as cyclohexyl, or multiple rings, such as adamantyl, but excludes aryl (i.e., aromatic) groups. A cycloalkyl comprising more than one ring may be fused, spiro, or bridged, or combinations thereof. Examples of cycloalkyl groups include, but are not limited to, cyclopropyl

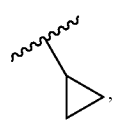

cyclobutyl

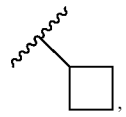 [SMILES: *C1CCC1]

cyclopentyl

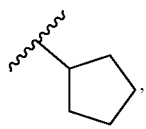

cyclohexyl

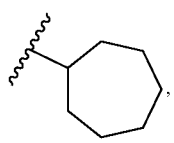 [SMILES: *C1CCCCCC1]

1-cyclohexenyl, 3-cyclohexenyl, cycloheptyl

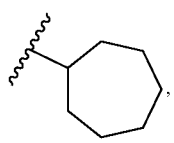 [SMILES: *C1CCCCCC1]

norbornyl, and the like.

"Cycloalkylene" as used herein refers to the same residues as cycloalkyl, but having bivalency, or are divalent. Particular cycloalkylene groups are those having 3 to 12 annular carbon atoms (a "$C_3$-$C_{12}$ cycloalkylene"), having from 3 to 8 annular carbon atoms (a "$C_3$-$C_8$ cycloalkylene"), or having 3 to 6 annular carbon atoms (a "$C_3$-$C_6$ cycloalkylene"). Examples of cycloalkylene groups include, but are not limited to, cyclopropylene

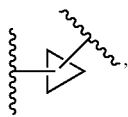

cyclobutylene

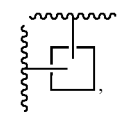

cyclopentylene

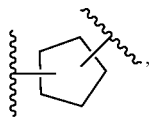

cyclohexylene

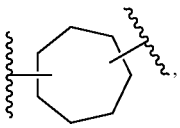

1,2-cyclohexenylene, 1,3-cyclohexenylene, 1,4-cyclohexenylene, cycloheptylene

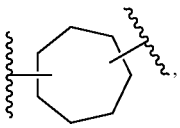

norbornylene, and the like.

"Halo" or "halogen" refers to elements of the Group 17 series having atomic number 9 to 85. Halo groups include fluoro (F), chloro (Cl), bromo (Br), and iodo (I).

"Haloalkyl," "haloalkylene," "haloaryl," "haloarylene," "haloheteroaryl," and similar terms refer to a moiety substituted with at least one halo group. Where a haloalkyl moiety or other halo-substituted moiety is substituted with more than one halogen, it may be referred to by using a prefix corresponding to the number of halogen moieties attached. For example, dihaloaryl, dihaloalkyl, trihaloaryl, trihaloalkyl, etc., refer to aryl and alkyl substituted with two ("di") or three ("tri") halo groups, which may be, but are not necessarily, the same halo; thus, for example, the haloaryl group 4-chloro-3-fluorophenyl is within the scope of dihaloaryl. The subset of haloalkyl groups in which each hydrogen (H) of an alkyl group is replaced with a halo group is referred to as a "perhaloalkyl." A particular perhaloalkyl group is trifluoroalkyl (—$CF_3$). Similarly, "perhaloalkoxy" refers to an alkoxy group in which a halogen takes the place of each hydrogen (H) in the hydrocarbon making up the alkyl moiety of the alkoxy group. An example of a perhaloalkoxy group is trifluoromethoxy (—$OCF_3$). "Haloalkyl"

includes monohaloalkyl, dihaloalkyl, trihaloalkyl, perhaloalkyl, and any other number of halo substituents possible on an alkyl group; and similarly for other groups such as haloalkylene, haloaryl, haloarylene, haloheteroaryl, etc.

"Heteroaryl" as used herein refers to an unsaturated aromatic cyclic group having from 1 to 14 annular carbon atoms and at least one annular heteroatom, including, but not limited to, heteroatoms such as nitrogen (N), oxygen (O), and sulfur (S). A heteroaryl group may have a single ring (e.g., pyridyl or imidazolyl) or multiple condensed rings (e.g., indolizinyl, indolyl, or quinolinyl) where at least one of the condensed rings is aromatic. Particular heteroaryl groups are 5- to 14-membered rings having 1 to 12 annular carbon atoms and 1 to 6 annular heteroatoms independently selected from the group consisting of nitrogen (N), oxygen (O), and sulfur (S) (a "5- to 14-membered heteroaryl"); 5- to 10-membered rings having 1 to 8 annular carbon atoms and 1 to 4 annular heteroatoms independently selected from the group consisting of nitrogen, oxygen, and sulfur (a "5- to 10-membered heteroaryl"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroaryl"). In one variation, heteroaryl includes monocyclic aromatic 5-, 6-, or 7-membered rings having from 1 to 6 annular carbon atoms and 1 to 4 annular heteroatoms independently selected from the group consisting of nitrogen, oxygen, and sulfur. In another variation, heteroaryl includes polycyclic aromatic rings having from 1 to 12 annular carbon atoms and 1 to 6 annular heteroatoms independently selected from the group consisting of nitrogen, oxygen, and sulfur. A heteroaryl group having more than one ring where at least one ring is non-aromatic may be connected to the parent structure at either an aromatic ring position or at a non-aromatic ring position. Examples of heteroaryl include, but are not limited to, groups such as pyridyl, benzimidazolyl, benzotriazolyl, benzo[b]thienyl, quinolinyl, indolyl, benzothiazolyl, and the like. "Heteroaryl" also includes moieties such as

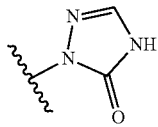 [SMILES: *n1nc[nH]c1=O]

(2,4-dihydro-3H-1,2,4-tri azol-3-one-2-yl), which has the aromatic tautomeric structure

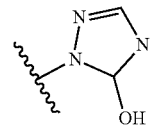 [SMILES: *N1N=CNC1O]

(1H-1,2,4-triazol-5-ol-1-yl).

"Heteroarylene" as used herein refers to the same residues as heteroaryl, but having bivalency, or are divalent. Particular heteroarylene groups are 5- to 14-membered rings having 1 to 12 annular carbon atoms and 1 to 6 annular heteroatoms independently selected from the group consisting of nitrogen, oxygen, and sulfur (a "5- to 14-membered heteroarylene"); 5- to 10-membered rings having 1 to 8 annular carbon atoms and 1 to 4 annular heteroatoms independently selected from the group consisting of nitrogen, oxygen, and sulfur (a "5- to 10-membered heteroarylene"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroarylene"). Examples of heteroarylene include, but are not limited to, groups such as pyridylene, benzimidazolylene, benzotriazolylene, benzo[b]thienylene, quinolinylene, indolylene, benzothiazolylene, and the like.

"Heterocyclyl" and "heterocyclic groups" as used herein refer to non-aromatic saturated or partially unsaturated cyclic groups having the number of atoms and heteroatoms as specified, or if no number of atoms or heteroatoms is specified, having at least three annular atoms, from 1 to 14 annular carbon atoms, and at least one annular heteroatom, including, but not limited to, heteroatoms such as nitrogen, oxygen, and sulfur. A heterocyclic group may have a single ring (e.g., tetrahydrothiopheneyl, oxazolidinyl) or multiple condensed rings (e.g., decahydroquinolinyl, octahydrobenzo[d]oxazolyl). Multiple condensed rings include, but are not limited to, bicyclic, tricyclic, and quadracylic rings, as well as bridged or spirocyclic ring systems. Examples of heterocyclic groups include, but are not limited to, aziridinyl, azetidinyl, pyrrolidinyl, piperidinyl, oxiranyl, oxetanyl, tetrahydrofuranyl, tetrahydropyranyl, oxazolidinyl, piperazinyl, morpholinyl, dioxanyl, 3,6-dihydro-2H-pyranyl, 2,3-dihydro-1H-imidazolyl, and the like.

"Oxo" refers to the group =O (e.g., carbonyl), that is, an oxygen atom doubly bonded to carbon or another chemical element.

"Optionally substituted," unless otherwise specified, means that a group is unsubstituted or substituted by one or more (e.g., 1, 2, 3, 4, or 5) of the substituents listed for that group, in which the substituents may be the same or different. In one embodiment, an optionally substituted group is unsubstituted. In one embodiment, an optionally substituted group has one substituent. In another embodiment, an optionally substituted group has two substituents. In another embodiment, an optionally substituted group has three substituents. In another embodiment, an optionally substituted group has four substituents. In certain embodiments, an optionally substituted group has 1 to 2, 1 to 3, 1 to 4, or 1 to 5 substituents. When multiple substituents are present, each substituent is independently chosen unless indicated otherwise. For example, each ($C_1$-$C_4$ alkyl) substituent on the group —N($C_1$-$C_4$ alkyl)($C_1$-$C_4$ alkyl) can be selected independently from the other, so as to generate groups such as —N($CH_3$)($CH_2CH_3$), etc.

The term "substituted," when used to modify a specified group or radical, can also mean that one or more hydrogen atoms (H) of the specified group or radical are each, independently of one another, replaced with the same or different substituent groups as defined herein. In certain embodiments, a group that is substituted has 1, 2, 3, or 4 substituents, 1, 2, or 3 substituents, 1 or 2 substituents, or one substituent.

Substituents can be attached to any chemically possible location on the specified group or radical, unless indicated otherwise. Thus, in one embodiment, —$C_1$-$C_8$ alkyl-OH includes, for example, —$CH_2CH_2OH$, —CH(OH)—$CH_3$, —$CH_2C(OH)(CH_3)_2$, and the like. By way of further example, in one embodiment, —$C_1$-$C_6$ alkyl-OH includes, for example, —$CH_2CH_2OH$, —CH(OH)—$CH_3$, —$CH_2C(OH)(CH_3)_2$, and the like. By way of further example, in one embodiment, —$C_1$-$C_6$ alkyl-CN includes, for example, —$CH_2CH_2CN$, —CH(CN)—$CH_3$, —$CH_2C(CN)(CH_3)_2$, and the like.

Unless a specific isotope of an element is indicated in a formula, the disclosure includes all isotopologues of the compounds disclosed herein, such as, for example, deuterated derivatives of the compounds (where H can be $^2$H, i.e., deuterium (D)). Deuterated compounds may provide favorable changes in pharmacokinetic (ADME) properties. Isotopologues can have isotopic replacements at any or at all locations in a structure, or can have atoms present in natural abundance at any or all locations in a structure.

A "small molecule" as used herein refers to a compound of 1,000 daltons or less in molecular weight.

Hydrogen atoms can also be replaced with bioisosteres, or close bioisosteres, such as fluorine, provided that such replacements result in stable compounds.

This disclosure also includes any or all of the stereochemical forms, including any enantiomeric or diastereomeric forms of the compounds described herein, and cis/trans or E/Z isomers. Unless stereochemistry is explicitly indicated in a chemical structure or name, the structure or name is intended to embrace all possible stereoisomers of a compound depicted. In addition, where a specific stereochemical form is depicted, it is understood that all other stereochemical forms are also described and embraced by this disclosure, as well as the general non-stereospecific form and mixtures of the disclosed compounds in any ratio, including mixtures of two or more stereochemical forms of a disclosed compound in any ratio, such that racemic, non-racemic, enantioenriched, and scalemic mixtures of a compound are embraced. Compositions comprising a disclosed compound also are intended, such as a composition of a substantially pure compound, including a specific stereochemical form thereof. Compositions comprising a mixture of disclosed compounds in any ratio also are embraced by the disclosure, including compositions comprising mixtures of two or more stereochemical forms of a disclosed compound in any ratio, such that racemic, non-racemic, enantioenriched, and scalemic mixtures of a compound are embraced by the disclosure. If stereochemistry is explicitly indicated for one portion or portions of a molecule, but not for another portion or portions of a molecule, the structure is intended to embrace all possible stereoisomers for the portion or portions where stereochemistry is not explicitly indicated.

This disclosure also embraces any and all tautomeric forms of the compounds described herein.

This disclosure is intended to embrace all salts of the compounds described herein, as well as methods of using such salts of the compounds. In one embodiment, the salts of the compounds comprise pharmaceutically acceptable salts. Pharmaceutically acceptable salts are those salts that can be administered as drugs or pharmaceuticals to humans and/or animals and that, upon administration, retain at least some of the biological activity of the free compound (i.e., neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, also can be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, NY-dibenzylethylenediamine, and triethylamine salts. Salts of acidic compounds with amino acids, such as lysine salts, also can be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66:1 (1977).

The terms "pharmaceutical formulation" and "pharmaceutical composition" refer to preparations that are in such form as to permit the biological activity of the active ingredient to be effective, and that contain no additional components that are unacceptably toxic to an individual to which the formulation or composition would be administered. Such formulations or compositions may be sterile. Such formulations or compositions may be sterile, with the exception of the inclusion of an oncolytic virus.

"Excipients" as used herein include pharmaceutically acceptable excipients, carriers, vehicles, or stabilizers that are nontoxic to the cell or mammal being exposed thereto at the dosages and concentrations employed. Often the physiologically acceptable excipient is an aqueous pH buffered solution.

Reference to a compound as described in a pharmaceutical composition, or to a compound as described in a claim to a pharmaceutical composition, refers to the compound described by the formula recited in the pharmaceutical composition, without the other elements of the pharmaceutical composition, that is, without carriers, excipients, etc.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "subject" means a mammalian subject. Exemplary subjects include, but are not limited to, humans, monkeys, dogs, cats, mice, rats, cows, horses, camels, avians, goats, and sheep. In certain embodiments, the subject is a human. In certain embodiments, the subject has a disease that can be treated or diagnosed with an antibody, an effective amount of Cbl-b inhibitor compound described herein, one or more checkpoint inhibitors described herein, and combinations thereof as provided herein. In certain embodiments, the disease is gastric carcinoma, colorectal carcinoma, renal cell carcinoma, cervical carcinoma, non-small cell lung carcinoma, ovarian cancer, breast cancer, triple-negative breast cancer, endometrial cancer, prostate cancer, and/or a cancer of epithelial origin.

An "effective amount" of an agent disclosed herein is an amount sufficient to carry out a specifically stated purpose. An "effective amount" may be determined empirically and in a routine manner, in relation to the stated purpose. An "effective amount" or an "amount sufficient" of an agent is that amount adequate to produce a desired biological effect, such as a beneficial result, including a beneficial clinical result. In certain embodiments, the term "effective amount" refers to an amount of an agent effective to "treat" a disease or disorder in an individual (e.g., a mammal such as a human).

2. Cbl-b Compounds

Figure 3:
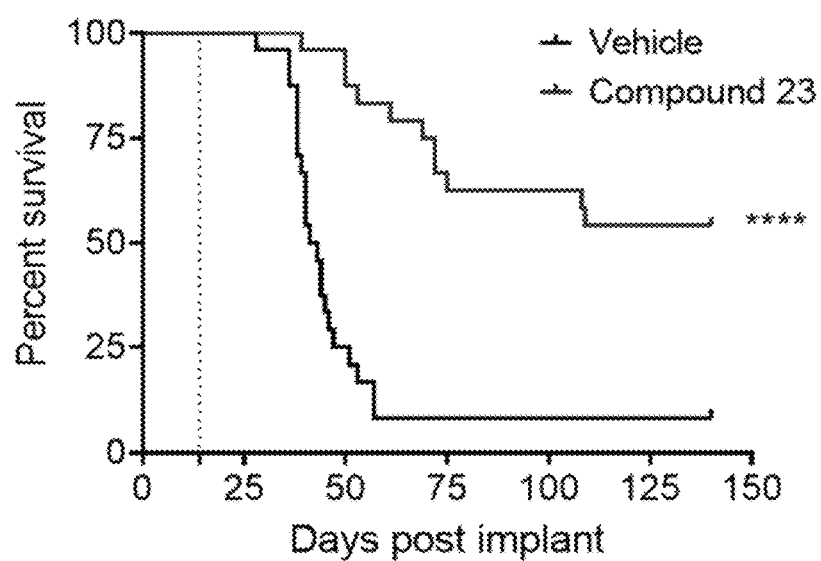
FIG. 3 provides the effect of compound 23 on survival of mice bearing 4T1 primary tumors, which are syngenic triple negative mammary carcinoma models.

Cbl-b is a negative regulator of immune cell activation and is expressed in leukocytes such as lymphocytes (e.g., T-cells and NK cells) and macrophages. As such, the Cbl-b signaling pathway is often exploited by cancer cells to evade and limit the antitumor effector function of these immune cells. Because Cbl-b inhibitors work across multiple immune cell types, inhibiting the Cbl-b signaling pathway has the potential to reverse these effects and enhance the effector function of various immune cells. For example, in CT26-tumor bearing mice treated with a Cbl-b inhibitor, increased levels of T-cell (in particular CD8+ T-cells and show elevated secretion of IL-2 and IFNγ) and NK cells are observed in circulation as well as in the tumor itself. This translates to anti-tumor efficacy as shown in FIG. 3. Experiments such as the one illustrated by FIG. 5 indicates that in some cancers, the anti-tumor effect of compound 23 is primarily mediated by CD8+ T-cells and NK cells.

Cbl-b inhibitors include small molecules, peptides, nucleic acids, or antibodies that inhibit the Cbl-h ligase. Illustrative examples of Cbl-b inhibitors include those described in PCT Publications WO 2019/148005, WO 2021/210508, WO 2020/236654, WO 2020/2643298, and WO 2021/021761. In certain embodiments, the Cbl-b inhibitor compound is a compound of Formula (I):

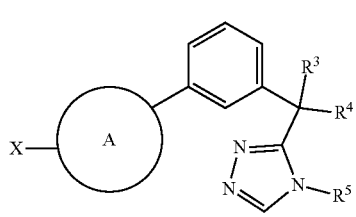

(I)

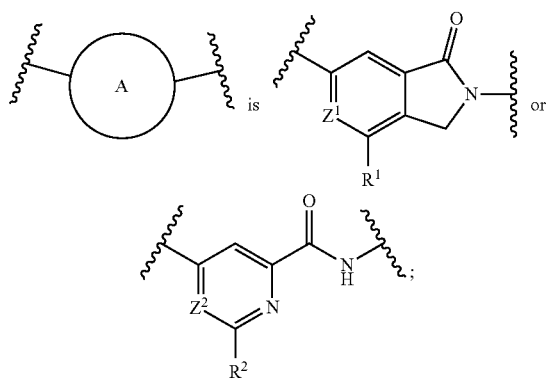

or a tautomer thereof, or a pharmaceutically acceptable salt thereof,
wherein:

$Z^1$ is CH or nitrogen;
$Z^2$ is CH or nitrogen;
$R^1$ is —$CF_3$ or cyclopropyl;
$R^2$ is —$CF_3$ or cyclopropyl;
$R^3$ is hydrogen, $C_1$-$C_2$ alkyl, or $C_1$-$C_2$ haloalkyl;
$R^4$ is hydrogen, $C_1$-$C_6$ alkyl, $C_1$-$C_6$ haloalkyl, 4- to 8-membered heterocyclyl, or $C_3$-$C_6$ cycloalkyl, wherein the heterocyclyl or cycloalkyl groups are optionally substituted by 1-5 $R^6$ groups;
or $R^3$ and $R^4$ are taken together with the carbon atom to which they are attached to form $C_1$-$C_5$ cycloalkyl or 4- to 6-membered heterocyclyl, each of which is optionally substituted by 1-5 $R^6$ groups;
$R^5$ is hydrogen, $C_1$-$C_6$ alkyl, $C_1$-$C_6$ haloalkyl, or $C_1$-$C_6$ cycloalkyl;
each $R^6$ is independently $C_1$-$C_6$ alkyl, halo, hydroxy, —O—($C_1$-$C_6$ alkyl), —CN, $C_1$-$C_6$ alkyl-CN, $C_1$-$C_6$ alkyl-OH, or $C_1$-$C_6$ haloalkyl;
or two $R^6$ groups attached to the same carbon atom are taken together with the carbon atom to which they are attached to form a spiro $C_1$-$C_6$ cycloalkyl or spiro 4- to 6-membered heterocyclyl;
X is hydrogen, $C_1$-$C_6$ alkyl, $C_1$-$C_6$ haloalkyl, $C_1$-$C_6$ alkyl-OH, $C_1$-$C_6$ alkyl-CN, $C_3$-$C_6$ cycloalkyl optionally substituted by 1-5 $R^8$ groups, or

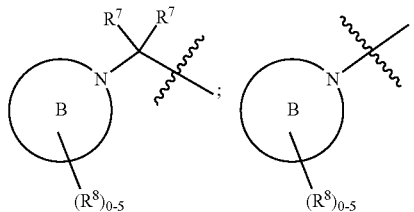

is 4- to 7-membered heterocyclyl or 5- to 8-membered heteroaryl, each of which heterocyclyl or heteroaryl optionally contains 1-2 additional heteroatoms selected from the group consisting of nitrogen, oxygen, and sulfur, and each of which heterocyclyl or heteroaryl is optionally substituted by 1-5 $R^8$ groups;
each $R^7$ is independently hydrogen, $C_1$-$C_6$ alkyl, $C_1$-$C_6$ alkyl-OH, or $C_1$-$C_6$ haloalkyl; or two $R^7$ groups are taken together with the carbon atom to which they are attached to form a $C_3$-$C_5$ cycloalkyl or 3- to 5-membered heterocyclyl; and
each $R^8$ is independently halo, $C_1$-$C_6$ alkyl, $C_1$-$C_6$ alkyl-CN, $C_1$-$C_6$ alkyl-OH, $C_1$-$C_6$ haloalkyl, —CN, oxo, or —O($C_1$-$C_6$ alkyl);
or two $R^8$ groups are taken together with the carbon atom or atoms to which they are attached to form a spiro or fused $C_3$-$C_5$ cycloalkyl or 3- to 5-membered heterocyclyl.

In certain embodiments,

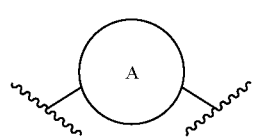

(i.e., the Ring A moiety), is

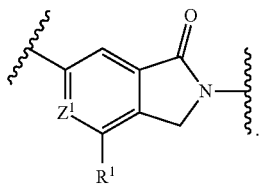

In certain embodiments, $Z^1$ is CH. In other embodiments, $Z^1$ is nitrogen. In certain embodiments, $R^1$ is —CF$_3$. In other embodiments, $R^1$ is cyclopropyl. In certain embodiments, the Ring A moiety is

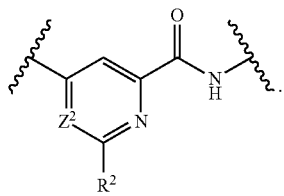

In certain embodiments, $Z^2$ is CH. In other embodiments, $Z^2$ is nitrogen. In certain embodiments, $R^2$ is —CF$_3$. In other embodiments, $R^2$ is cyclopropyl. In certain embodiments, the Ring A moiety is selected from the group consisting of:

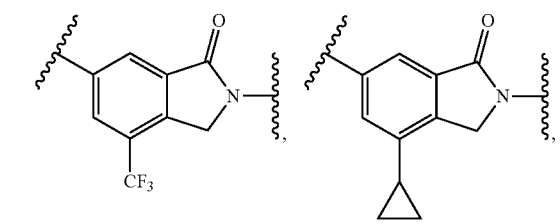

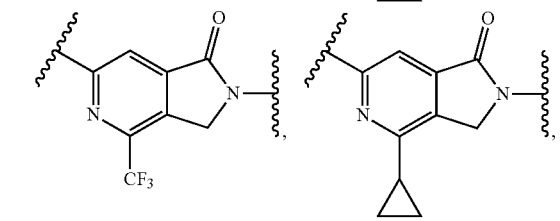

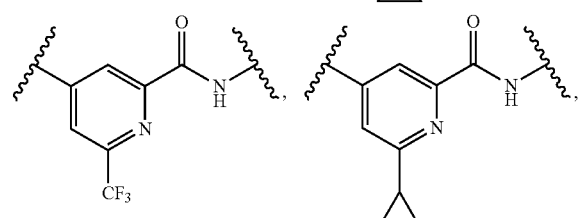

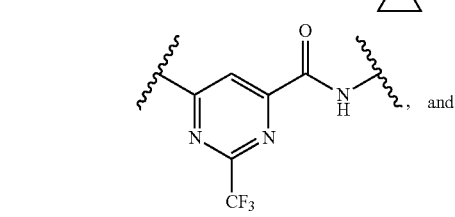, and

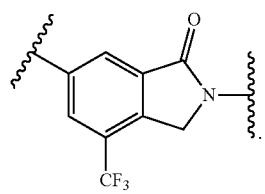 [SMILES: *c1cc2c(c(C(F)(F)F)c1)CN(*)C2=O]

In certain embodiments, the Ring A moiety is

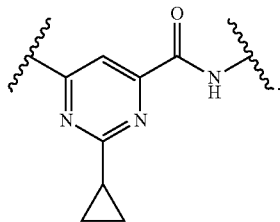

In certain embodiments, the Ring A moiety is

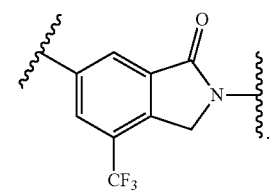

In certain embodiments, the Ring A moiety is

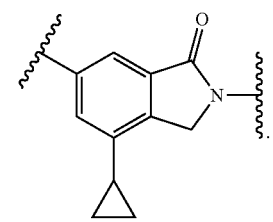 [SMILES: *c1cc2c(c(C3CC3)c1)CN(*)C2=O]

In certain embodiments, the Ring A moiety is

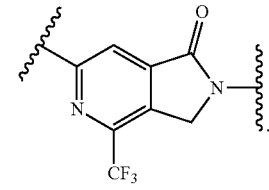 [SMILES: *c1cc2c(c(C(F)(F)F)n1)CN(*)C2=O]

In certain embodiments, the Ring A moiety is

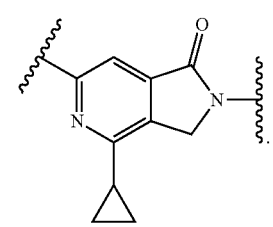 [SMILES: *c1cc2c(c(C3CC3)n1)CN(*)C2=O]

In certain embodiments, the Ring A moiety is

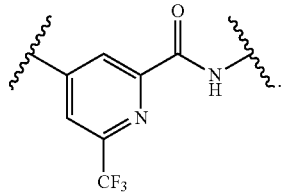

In certain embodiments, the Ring A moiety is

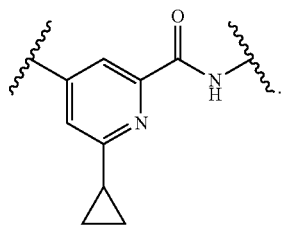 [SMILES: *NC(=O)c1cc(*)cc(C2CC2)n1]

In certain embodiments, the Ring A moiety is

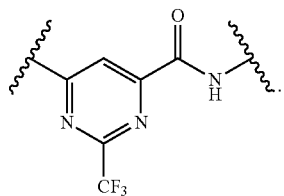 [SMILES: *NC(=O)c1cc(*)nc(C(F)(F)F)n1]

In certain embodiments, the Ring A moiety is

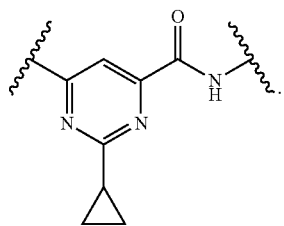 [SMILES: *NC(=O)c1cc(*)nc(C2CC2)n1]

In certain embodiments, $R^3$ is hydrogen, $C_1$-$C_2$ alkyl, or $C_1$-$C_2$ haloalkyl. In certain embodiments, $R^3$ is hydrogen, —$CH_3$, or —$CF_3$.

In certain embodiments, $R^3$ is hydrogen.

In certain embodiments, $R^3$ is $C_1$-$C_2$ alkyl. In certain embodiments, $R^3$ is methyl. In certain embodiments, $R^3$ is ethyl.

In certain embodiments, $R^3$ is $C_1$-$C_2$ haloalkyl. In certain embodiments, $R^3$ is $C_1$-$C_2$ haloalkyl containing 1-5 halogen atoms. In certain embodiments, $R^3$ is $C_1$-$C_2$ haloalkyl containing 1-3 halogen atoms. In certain embodiments, $R^3$ is $C_1$ haloalkyl. In certain embodiments, $R^3$ is $C_2$ haloalkyl. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, $R^3$ is —$CF_3$, —$CCl_3$, —$CF_2Cl$, —$CFCl_2$, —$HF_2$, —$CH_2F$, —$CHCl_2$, —$CH_2Cl$, or —$CHFCl$. In certain embodiments, $R^3$ is —$CF_3$.

In certain embodiments, $R^4$ is hydrogen, $C_1$-$C_6$ alkyl, $C_1$-$C_6$ haloalkyl, 4- to 8-membered heterocyclyl, or $C_1$-$C_6$ cycloalkyl, wherein the heterocyclyl or cycloalkyl groups are optionally substituted by 1-5 $R^6$ groups. In certain embodiments, $R^4$ is hydrogen, $C_1$-$C_3$ alkyl, $C_1$-$C_3$ haloalkyl, 4- to 6-membered heterocyclyl, or $C_1$-$C_5$ cycloalkyl, wherein the heterocyclyl or cycloalkyl groups are optionally substituted by 1-3 $R^6$ groups. In certain embodiments, $R^4$ is hydrogen, —$CH_3$, —$CF_3$, cyclobutyl, or

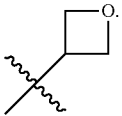

In certain embodiments, $R^4$ is hydrogen.

In certain embodiments, $R^4$ is $C_1$-$C_6$ alkyl. In certain embodiments, $R^4$ is $C_1$-$C_3$ alkyl. In certain embodiments, $R^4$ is methyl, ethyl, n-propyl, or isopropyl. In certain embodiments, $R^4$ is —$CH_3$.

In certain embodiments, $R^4$ is $C_1$-$C_6$ haloalkyl. In certain embodiments, $R^4$ is $C_1$-$C_6$ haloalkyl containing 1-7 halogen atoms. In certain embodiments, $R^4$ is $C_1$-$C_3$ haloalkyl. In certain embodiments, $R^4$ is $C_1$-$C_3$ haloalkyl containing 1-7 halogen atoms. In certain embodiments, $R^4$ is $C_1$-$C_2$ haloalkyl containing 1-5 halogen atoms. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, $R^4$ is —$CF_3$, —$CCl_3$, —$CF_2Cl$, —$CFCl_2$, —$CHF_2$, —$CH_2F$, —$CHCl_2$, —$CH_2F$, or —$CHFCl$. In certain embodiments, $R^4$ is —$CF_3$.

In certain embodiments, $R^4$ is 4- to 8-membered heterocyclyl optionally substituted by 1-5 $R^6$ groups. In certain embodiments, $R^4$ is 4- to 6-membered heterocyclyl optionally substituted by 1-3 $R^6$ groups. In certain embodiments, $R^4$ is a 4-membered heterocyclyl optionally substituted by 1-2 $R^6$ groups. In certain embodiments, the heterocyclyl is substituted by five $R^6$ groups. In certain embodiments, the heterocyclyl is substituted by four $R^6$ groups. In certain embodiments, the heterocyclyl is substituted by three $R^6$ groups. In certain embodiments, the heterocyclyl is substituted by two $R^6$ groups. In certain embodiments, the heterocyclyl is substituted by one $R^6$ group. In certain embodiments, the heterocyclyl is unsubstituted. In certain embodiments, the heterocyclyl contains 1-3 heteroatoms selected from the group consisting of nitrogen, oxygen, and sulfur. In certain embodiments, the heterocyclyl contains one nitrogen atom. In certain embodiments, the heterocyclyl contains two nitrogen atoms. In certain embodiments, the heterocyclyl contains one oxygen atom. In certain embodiments, the heterocyclyl contains two oxygen atoms. In certain embodiments, the heterocyclyl contains one oxygen atom and one nitrogen atom. In certain embodiments, the heterocyclyl contains one sulfur atom. In certain embodiments, the heterocyclyl contains one nitrogen atom and one sulfur atom. In certain embodiments, $R^4$ is oxetanyl, azetidinyl, tetrahydrofuranyl, dioxolanyl, pyrrolidinyl, pyrazolidinyl, piperidinyl, isoxazolidinyl, or tetrahydropyranyl, each of which is optionally substituted by 1-5 $R^6$ groups. In certain embodiments, $R^4$ is:

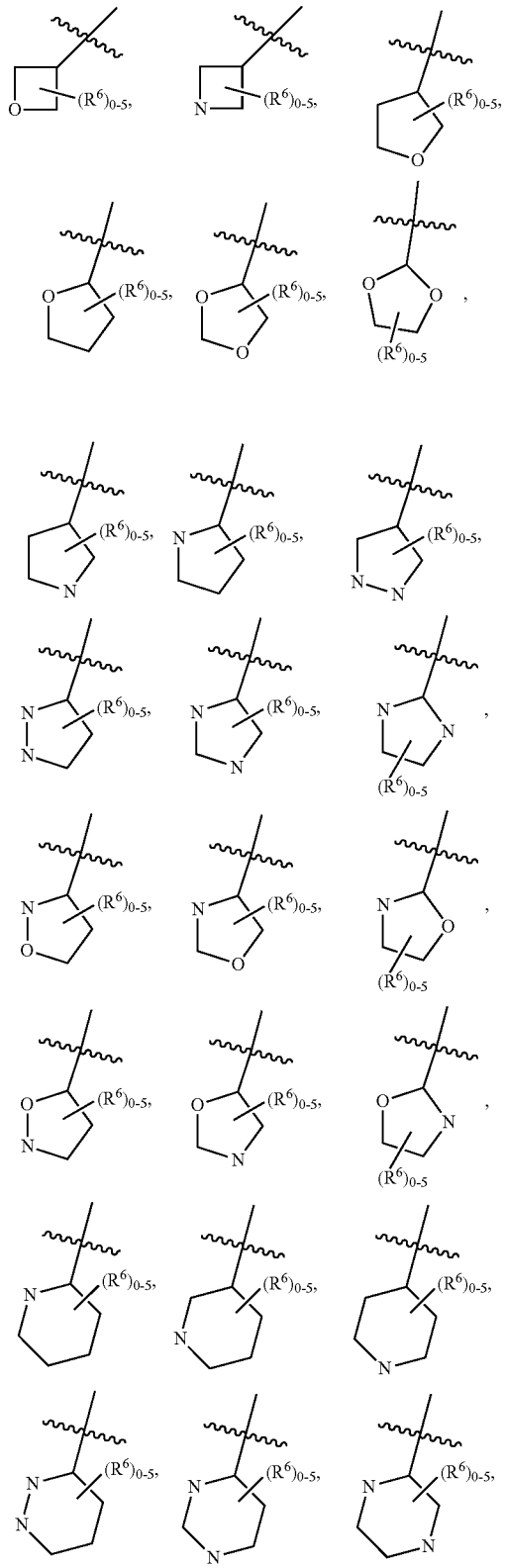

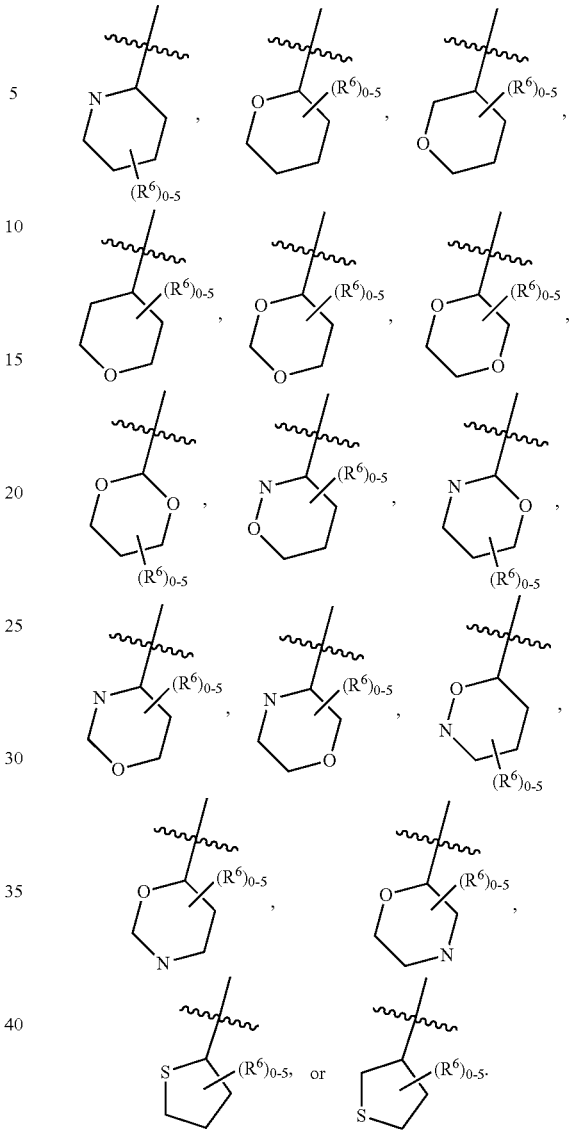

In certain embodiments, $R^4$ is

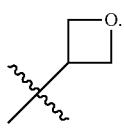

In certain embodiments, $R^4$ is $C_3$-$C_6$ cycloalkyl optionally substituted by 1-5 $R^6$ groups. In certain embodiments, $R^4$ is $C_4$-$C_5$ cycloalkyl optionally substituted by 1-3 $R^6$ groups. In certain embodiments, the cycloalkyl is substituted by five $R^6$ groups. In certain embodiments, the cycloalkyl is substituted by four $R^6$ groups. In certain embodiments, the cycloalkyl is substituted by three $R^6$ groups. In certain embodiments, the cycloalkyl is substituted by two $R^6$ groups. In certain embodiments, the cycloalkyl is substituted by one $R^6$ group. In certain embodiments, the cycloalkyl is unsubstituted. In certain embodiments, $R^4$ is cyclopropyl, cyclobutyl, cyclopentyl, or cyclohexyl, each of which is optionally substituted by 1-5 $R^6$ groups. In certain embodiments, $R^4$ is cyclopropyl or cyclobutyl. In certain embodiments, $R^4$ is cyclobutyl.

In certain embodiments, $R^3$ and $R^4$ are taken together with the carbon atom to which they are attached to form $C_3$-$C_5$ cycloalkyl or 4- to 6-membered heterocyclyl, each of which is optionally substituted by 1-5 $R^6$ groups. In certain embodiments, $R^3$ and $R^4$ are taken together with the carbon atom to which they are attached to form $C_4$-$C_5$ cycloalkyl or 4- to 6-membered heterocyclyl, each of which is optionally substituted by 1-3 $R^6$ groups. In certain embodiments, $R^3$ and $R^4$ are taken together with the carbon atom to which they are attached to form

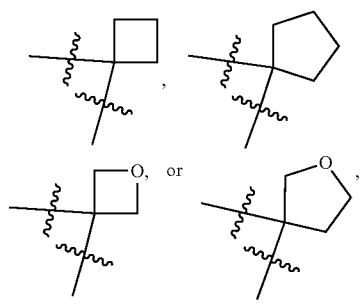

each of which is optionally substituted by 1-3 $R^6$ groups. In certain embodiments, $R^3$ and $R^4$ are taken together with the carbon atom to which they are attached, and
are substituted by one $R^6$ group which is methyl, to form

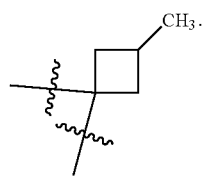

In certain embodiments, $R^3$ and $R^4$ are taken together with the carbon atom to which they are attached to form $C_3$-$C_5$ cycloalkyl optionally substituted by 1-5 $R^6$ groups. In certain embodiments, $R^3$ and $R^4$ are taken together with the carbon atom to which they are attached to form $C_4$-$C_5$ cycloalkyl optionally substituted by 1-3 $R^6$ groups. In certain embodiments, the cycloalkyl is substituted by five $R^6$ groups. In certain embodiments, the cycloalkyl is substituted by four $R^6$ groups. In certain embodiments, the cycloalkyl is substituted by three $R^6$ groups. In certain embodiments, the cycloalkyl is substituted by two $R^6$ groups. In certain embodiments, the cycloalkyl is substituted by one $R^6$ group. In certain embodiments, the cycloalkyl is unsubstituted. In certain embodiments, $R^3$ and $R^4$ are taken together with the carbon atom to which they are attached to form

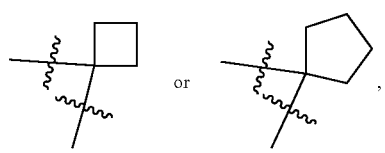 [SMILES: *C1(*)CCC1 ; *C1(*)CCCC1]

each of which is optionally substituted by 1-3 $R^6$ groups. In certain embodiments, $R^3$ and $R^4$ are taken together with the carbon atom to which they are attached, and are substituted by one $R^6$ group which is methyl, to form

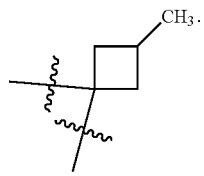 [SMILES: *C1(*)CC(C)C1 ; "."]

In certain embodiments, the absolute stereochemistry at the carbon atom to which the methyl group of

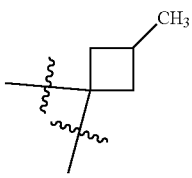 [SMILES: *C1(*)CC(C)C1]

is attached is (R)— (using the Cahn-Ingold-Prelog rules). In certain embodiments, the absolute stereochemistry at the carbon atom to which the methyl group of

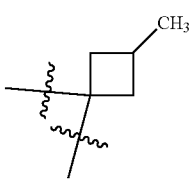 [SMILES: *C1(*)CC(C)C1]

is attached is (S)—.

In certain embodiments, $R^3$ and $R^4$ are taken together with the carbon atom to which they are attached to form 4- to 6-membered heterocyclyl optionally substituted by 1-5 $R^6$ groups. In certain embodiments, $R^3$ and $R^4$ are taken together with the carbon atom to which they are attached to form 4- to 6-membered heterocyclyl optionally substituted by 1-3 $R^6$ groups. In certain embodiments, the heterocyclyl is substituted by five $R^6$ groups. In certain embodiments, the heterocyclyl is substituted by four $R^6$ groups. In certain embodiments, the heterocyclyl is substituted by three $R^6$ groups. In certain embodiments, the heterocyclyl is substituted by two $R^6$ groups. In certain embodiments, the heterocyclyl is substituted by one $R^6$ group. In certain embodiments, the heterocyclyl is unsubstituted. In certain embodiments, the heterocyclyl contains 1-3 heteroatoms selected from the group consisting of nitrogen, oxygen, and sulfur. In certain embodiments, the heterocyclyl contains one nitrogen atom. In certain embodiments, the heterocyclyl contains two nitrogen atoms. In certain embodiments, the heterocyclyl contains one oxygen atom. In certain embodiments, the heterocyclyl contains two oxygen atoms. In certain embodiments, the heterocyclyl contains one oxygen atom and one nitrogen atom. In certain embodiments, the heterocyclyl contains one sulfur atom. In certain embodiments, the heterocyclyl contains one nitrogen atom and one sulfur atom. In certain embodiments, $R^4$ is oxetanyl, azetidinyl, tetrahydrofuranyl, dioxolanyl, pyrrolidinyl, pyrazolidinyl, piperidinyl, isoxazolidinyl, or tetrahydropyranyl, each of which is optionally substituted by 1-5 $R^6$ groups. In certain embodiments, $R^3$ and $R^4$ are taken together with the carbon atom to which they are attached to form

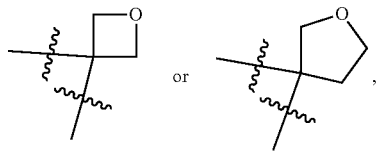 [SMILES: *C1(*)COC1 ; *C1(*)CCOC1]

each of which is optionally substituted by 1-3 $R^6$ groups. In certain embodiments, $R^3$ and $R^4$ are taken together with the carbon atom to which they are attached to form

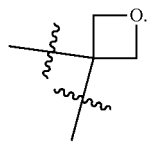

In certain embodiments, $R^3$ and $R^4$ are taken together with the carbon atom to which they are attached to form

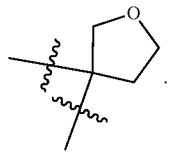 [SMILES: *C1(*)CCOC1]

In certain embodiments, each $R^6$ is independently $C_1$-$C_6$ alkyl, halo, hydroxy, —O—($C_1$-$C_6$ alkyl), —CN, $C_1$-$C_6$ alkyl-CN, $C_1$-$C_6$ alkyl-OH, or $C_1$-$C_6$ haloalkyl. In certain embodiments, each $R^6$ is independently $C_1$-$C_6$ alkyl, halo, hydroxy, —O—($C_1$-$C_3$ alkyl), —CN, $C_1$-$C_3$ alkyl-CN, $C_1$-$C_3$ alkyl-OH, or $C_1$-$C_3$ haloalkyl. In certain embodiments, each $R^6$ is independently —$CH_3$, fluoro (F), hydroxy, —$OCH_3$, —CN, —$CH_2CN$, —$CH_2OH$, or —$CF_3$.

In certain embodiments, $R^6$ is $C_1$-$C_6$ alkyl. In certain embodiments, $R^6$ is $C_1$-$C_3$ alkyl. In certain embodiments, $R^6$ is methyl, ethyl, n-propyl, or isopropyl. In certain embodiments, $R^6$ is —$CH_3$.

In certain embodiments, $R^6$ is halo. In certain embodiments, $R^6$ is chloro, fluoro, or bromo. In certain embodiments, $R^6$ is chloro or fluoro. In certain embodiments, $R^7$ is fluoro.

In certain embodiments, $R^6$ is hydroxyl.

In certain embodiments, $R^6$ is —O($C_1$-$C_6$ alkyl). In certain embodiments, $R^6$ is —O—($C_1$-$C_6$ alkyl). In certain embodiments, $R^6$ is —O(methyl), —O(ethyl), —O(n-propyl), or —O(isopropyl). In certain embodiments, $R^6$ is —$OCH_3$ or —$OCH_2CH_3$. In certain embodiments, $R^6$ is —$OCH_3$.

In certain embodiments, $R^6$ is —CN. In certain embodiments, $R^6$ is $C_1$-$C_6$ alkyl-CN. In certain embodiments, $R^6$ is $C_1$-$C_3$ alkyl-CN. In certain embodiments, $R^6$ is —$CH_2CN$, —$CH_2CH_2$—CN, —$CH_2CH_2CH_2$—CN, or —$C(CH_3)_2$—CN. In certain embodiments, $R^6$ is —$CH_2CN$.

In certain embodiments, $R^6$ is $C_1$-$C_6$ alkyl-OH. In certain embodiments, $R^6$ is $C_1$-$C_3$ alkyl-OH. In certain embodiments, $R^6$ is —$CH_2OH$, —$CH_2CH_2$—OH, —$CH_2CH_2CH_2$—OH, or —$C(CH_3)_2$—OH. In certain embodiments, $R^6$ is —$CH_2OH$.

In certain embodiments, $R^6$ is $C_1$-$C_6$ haloalkyl. In certain embodiments, $R^6$ is $C_1$-$C_6$ haloalkyl containing 1-7 halogen atoms. In certain embodiments, $R^6$ is $C_1$-$C_3$ haloalkyl. In certain embodiments, $R^6$ is $C_1$-$C_3$ haloalkyl containing 1-7 halogen atoms. In certain embodiments, $R^6$ is $C_1$-$C_5$ haloalkyl containing 1-5 halogen atoms. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, $R^6$ is —$CF_3$, —$CCl_3$, —$CF_2Cl$, —$CFCl_2$, —$CHF_2$, —$CH_2F$, —$CHCl_2$, —$CH_2Cl$, or —$CHFCl$. In certain embodiments, $R^6$ is —$CF_3$.

In certain embodiments, two $R^6$ groups attached to the same carbon atom are taken together with the carbon atom to which they are attached to form a spiro $C_3$-$C_6$ cycloalkyl or spiro 4- to 6-membered heterocyclyl. In certain embodiments, two $R^6$ groups attached to the same carbon atom are taken together with the carbon atom to which they are attached to form a spiro $C_3$-$C_6$ cycloalkyl or spiro 4- to 5-membered heterocyclyl.

In certain embodiments, two $R^6$ groups attached to the same carbon atom are taken together with the carbon atom to which they are attached to form a spiro $C_3$-$C_6$ cycloalkyl. In certain embodiments, two $R^6$ groups attached to the same carbon atom are taken together with the carbon atom to which they are attached to form a spiro $C_3$-$C_6$ cycloalkyl. In certain embodiments, two $R^6$ groups attached to the same carbon atom are taken together with the carbon atom to which they are attached to form a spiro $C_3$-$C_4$ cycloalkyl. In certain embodiments, two $R^6$ groups attached to the same carbon atom are taken together with the carbon atom to which they are attached to form a spiro cyclopropyl, cyclobutyl, or cyclopentyl. In certain embodiments, two $R^6$ groups attached to the same carbon atom are taken together with the carbon atom to which they are attached to form a spiro cyclopropyl.

In certain embodiments, two $R^6$ groups attached to the same carbon atom are taken together with the carbon atom to which they are attached to form a spiro 4- to 6-membered heterocyclyl. In certain embodiments, two $R^6$ groups attached to the same carbon atom are taken together with the carbon atom to which they are attached to form a spiro 4- to 5-membered heterocyclyl. In certain embodiments, the heterocyclyl contains 1-3 heteroatoms selected from the group consisting of nitrogen, oxygen, and sulfur. In certain embodiments, the heterocyclyl contains one nitrogen atom. In certain embodiments, the heterocyclyl contains two nitrogen atoms. In certain embodiments, the heterocyclyl contains one oxygen atom. In certain embodiments, the heterocyclyl contains two oxygen atoms. In certain embodiments, the heterocyclyl contains one oxygen atom and one nitrogen atom. In certain embodiments, the heterocyclyl contains one sulfur atom. In certain embodiments, the heterocyclyl contains one nitrogen atom and one sulfur atom. In certain embodiments, two $R^6$ groups attached to the same carbon atom are taken together with the carbon atom to which they are attached to form a spiro oxetanyl, azetidinyl, tetrahydrofuranyl, dioxolanyl, pyrrolidinyl, pyrazolidinyl, piperidinyl, isoxazolidinyl, or tetrahydropyranyl.

In certain embodiments, $R^5$ is hydrogen, $C_1$-$C_6$ alkyl, $C_1$-$C_6$ haloalkyl, or $C_3$-$C_6$ cycloalkyl. In certain embodiments, $R^5$ is hydrogen, $C_1$-$C_3$ alkyl, $C_1$-$C_3$ haloalkyl, or $C_3$-$C_4$ cycloalkyl. In certain embodiments, $R^5$ is hydrogen, —$CH_3$, —$CHF_2$, or cyclopropyl.

In certain embodiments, $R^5$ is hydrogen.

In certain embodiments, $R^5$ is $C_1$-$C_6$ alkyl. In certain embodiments, $R^5$ is $C_1$-$C_6$ alkyl. In certain embodiments, $R^5$ is methyl, ethyl, n-propyl, or isopropyl. In certain embodiments, $R^5$ is —$CH_3$.

In certain embodiments, $R^5$ is $C_3$-$C_6$ haloalkyl. In certain embodiments, $R^5$ is $C_3$-$C_6$ haloalkyl containing 1-7 halogen atoms. In certain embodiments, $R^5$ is $C_1$-$C_3$ haloalkyl. In certain embodiments, $R^5$ is $C_1$-$C_3$ haloalkyl containing 1-7 halogen atoms. In certain embodiments, $R^5$ is $C_1$-$C_3$ haloalkyl containing 1-5 halogen atoms. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, $R^5$ is —$CF_3$, —$CCl_3$, —$CF_2Cl$, —$CFCl_2$, —$CHF_2$, —$CH_2F$, —$CHCl_2$, —$CH_2Cl$, or —$CHFCl$. In certain embodiments, $R^5$ is —$CHF_2$.

In certain embodiments, $R^5$ is $C_3$-$C_6$ cycloalkyl. In certain embodiments, $R^5$ is $C_3$-$C_6$ cycloalkyl. In certain embodiments, $R^5$ is $C_3$-$C_4$ cycloalkyl. In certain embodiments, $R^5$ is cyclopropyl, cyclobutyl, or cyclopentyl. In certain embodiments, $R^5$ is cyclopropyl.

In certain embodiments, X is hydrogen, $C_1$-$C_6$ alkyl, $C_1$-$C_6$ haloalkyl, $C_1$-$C_6$ alkyl-OH, $C_1$-$C_6$ alkyl-CN, or $C_3$-$C_6$ cycloalkyl optionally substituted by 1-5 $R^8$ groups. In certain embodiments, X is hydrogen, $C_1$-$C_3$ alkyl, $C_1$-$C_6$ haloalkyl, $C_1$-$C_3$ alkyl-OH, $C_1$-$C_6$ alkyl-CN, or $C_3$-$C_5$ cycloalkyl optionally substituted by 1-3 $R^8$ groups. In certain embodiments, X is hydrogen or —$CH_3$.

In certain embodiments, X is hydrogen.

In certain embodiments, X is $C_1$-$C_6$ alkyl. In certain embodiments, X is $C_1$-$C_3$ alkyl. In certain embodiments, X is methyl, ethyl, n-propyl, or isopropyl. In certain embodiments, X is —$CH_3$.

In certain embodiments, X is $C_1$-$C_6$ haloalkyl. In certain embodiments, X is $C_1$-$C_6$ haloalkyl containing 1-7 halogen atoms. In certain embodiments, X is $C_1$-$C_3$ haloalkyl. In certain embodiments, X is $C_1$-$C_3$ haloalkyl containing 1-7 halogen atoms. In certain embodiments, X is $C_1$-$C_3$ haloalkyl containing 1-5 halogen atoms. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, X is —$CF_3$, —$CCl_3$, —$CF_2Cl$, —$CFCl_2$, —$CHF_2$, —$CH_2F$, —$CHCl_2$, —$CH_2Cl$, or —$CHFCl$. In certain embodiments, X is —$CF_3$.

In certain embodiments, X is $C_1$-$C_6$ alkyl-OH. In certain embodiments, X is $C_1$-$C_3$ alkyl-OH. In certain embodiments, X is —$CH_2OH$, —$CH_2CH_2$—OH, —$CH_2CH_2CH_2$—OH, or —$C(CH_3)_2$—OH. In certain embodiments, X is —$CH_2OH$.

In certain embodiments, X is $C_1$-$C_6$ alkyl-CN. In certain embodiments, X is $C_1$-$C_3$ alkyl-CN. In certain embodiments, X is —$CH_2CN$, —$CH_2CH_2$—CN, —$CH_2CH_2CH_2$—CN, or —$C(CH_3)_2$—CN. In certain embodiments, X is —$CH_2CN$.

In certain embodiments, X is $C_3$-$C_6$ cycloalkyl optionally substituted by 1-5 $R^8$ groups. In certain embodiments, X is $C_3$-$C_5$ cycloalkyl optionally substituted by 1-3 $R^8$ groups. In certain embodiments, the cycloalkyl is substituted by five $R^8$ groups. In certain embodiments, the cycloalkyl is substituted by four $R^8$ groups. In certain embodiments, the cycloalkyl is substituted by three $R^8$ groups. In certain embodiments, the cycloalkyl is substituted by two $R^8$ groups. In certain embodiments, the cycloalkyl is substituted by one $R^8$ group. In certain embodiments, the cycloalkyl is unsubstituted. In certain embodiments, X is cyclopropyl, cyclobutyl, or cyclopentyl, each of which is optionally substituted by 1-5 $R^8$ groups. In certain embodiments, X is cyclopropyl.

In certain embodiments, X is

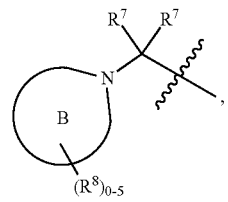

wherein the Ring B moiety, shown as

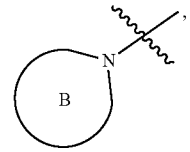

is a 4- to 7-membered heterocyclyl or 5- to 8-membered heteroaryl, each of which heterocyclyl or heteroaryl optionally contains 1-2 additional heteroatoms selected from the group consisting of nitrogen, oxygen, and sulfur, and each of which heterocyclyl or heteroaryl is optionally substituted by 1-5 $R^8$ groups. In certain embodiments, the Ring B moiety is a 4- to 6-membered heterocyclyl or 5- to 6-membered heteroaryl, each of which heterocyclyl or heteroaryl optionally contains 1-2 additional heteroatoms selected from the group consisting of nitrogen, oxygen, and sulfur, and each of which heterocyclyl or heteroaryl is optionally substituted by 1-5 $R^8$ groups. In certain embodiments, the Ring B moiety is a 4- to 5-membered heterocyclyl or 5- to 6-membered heteroaryl, each of which heterocyclyl or heteroaryl optionally contains one additional heteroatom selected from the group consisting of nitrogen and oxygen, and each of which heterocyclyl or heteroaryl is optionally substituted by 1-5 $R^8$ groups.

In certain embodiments, the Ring B moiety is a 4- to 7-membered heterocyclyl optionally containing 1-2 additional heteroatoms selected from the group consisting of nitrogen, oxygen, and sulfur, wherein the heterocyclyl is optionally substituted by 1-5 $R^8$ groups. In certain embodiments, the Ring B moiety is a 4- to 6-membered heterocyclyl optionally containing 1-2 additional heteroatoms selected from the group consisting of nitrogen, oxygen, and sulfur, wherein the heterocyclyl is optionally substituted by 1-5 $R^8$ groups. In certain embodiments, the Ring B moiety is a 4- to 5-membered heterocyclyl optionally containing one additional heteroatom selected from the group consisting of nitrogen and oxygen, wherein the heterocyclyl is optionally substituted by 1-5 $R^8$ groups. In certain embodiments, the heterocyclyl is substituted by five $R^8$ groups. In certain embodiments, the heterocyclyl is substituted by four $R^8$ groups. In certain embodiments, the heterocyclyl is substituted by three $R^8$ groups. In certain embodiments, the heterocyclyl is substituted by two $R^8$ groups. In certain embodiments, the heterocyclyl is substituted by one $R^8$ group. In certain embodiments, the heterocyclyl is unsubstituted. In certain embodiments, the heterocyclyl contains 1-2 additional heteroatoms selected from the group consisting of nitrogen, oxygen, and sulfur. In certain embodiments, the heterocyclyl contains one additional nitrogen atom. In certain embodiments, the heterocyclyl contains two additional nitrogen atoms. In certain embodiments, the heterocyclyl further contains one oxygen atom. In certain embodiments, the heterocyclyl further contains two oxygen atoms. In certain embodiments, the heterocyclyl further contains one oxygen atom and one nitrogen atom. In certain embodiments, the heterocyclyl further contains one sulfur atom. In certain embodiments, the heterocyclyl does not contain additional heteroatoms. In certain embodiments, the heterocyclyl is azetidinyl, pyrrolidinyl, pyrazolidinyl, piperidinyl, or isoxazolidinyl, each of which is optionally substituted by 1-5 $R^8$ groups.

In certain embodiments, the Ring B moiety is a 5- to 8-membered heteroaryl optionally containing 1-2 additional heteroatoms selected from the group consisting of nitrogen, oxygen, and sulfur, wherein the heteroaryl is optionally substituted by 1-5 $R^8$ groups. In certain embodiments, the Ring B moiety is a 5- to 6-membered heteroaryl optionally containing 1-2 additional heteroatoms selected from the group consisting of nitrogen, oxygen, and sulfur, wherein the heteroaryl is optionally substituted by 1-5 $R^8$ groups. In certain embodiments, the Ring B moiety is a 5- to 6-membered heteroaryl optionally containing one additional heteroatom selected from the group consisting of nitrogen and oxygen, wherein the heteroaryl is optionally substituted by 1-5 $R^8$ groups. In certain embodiments, the heteroaryl is substituted by five $R^8$ groups. In certain embodiments, the heteroaryl is substituted by four $R^8$ groups. In certain embodiments, the heteroaryl is substituted by three $R^8$ groups. In certain embodiments, the heteroaryl is substituted by two $R^8$ groups. In certain embodiments, the heteroaryl is substituted by one $R^8$ group. In certain embodiments, the heteroaryl is unsubstituted. In certain embodiments, the heteroaryl contains 1-2 additional heteroatoms selected from the group consisting of nitrogen, oxygen, and sulfur. In certain embodiments, the heteroaryl contains one additional nitrogen atom. In certain embodiments, the heteroaryl contains two additional nitrogen atoms. In certain embodiments, the heteroaryl further contains one oxygen atom. In certain embodiments, the heteroaryl further contains two oxygen atoms. In certain embodiments, the heteroaryl further contains one oxygen atom and one additional nitrogen atom. In certain embodiments, the heteroaryl further contains one sulfur atom. In certain embodiments, the heteroaryl does not contain additional heteroatoms. In certain embodiments, the heteroaryl is pyrrolyl, imidazolyl, pyrazolyl, isoxazolyl, oxazolyl, thiazolyl, isothiazolyl, triazolyl, pyridinyl, pyridazinyl, pyrimidinyl, pyrazinyl, or triazyl, each of which is optionally substituted by 1-5 $R^8$ groups.

In certain embodiments, the Ring B moiety is

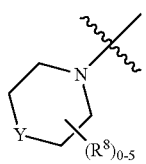

wherein Y is oxygen, —$CH_2$—, —$CHR^8$—, or —$C(R^8)_2$—, and X is

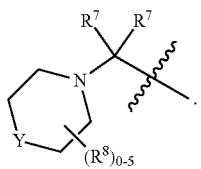

In certain embodiments, Y is oxygen (O). In other embodiments, Y is —$CH_2$—, —$CHR^8$—, or —$C(R^8)_2$—. In certain embodiments, Y is —$CH_2$—. In certain embodiments, Y is —$CHR^8$—. In certain embodiments, Y is —$C(R^8)_2$—. In certain embodiments, the Ring B moiety is substituted by a total of 1-5 $R^8$ groups. In certain embodiments, the Ring B moiety is substituted by a total of 1-3 $R^8$ groups. As such, if Y is —$CHR^8$—, then the Ring B moiety can be substituted by up to four additional $R^8$ groups. Similarly, if Y is —$C(R^8)_2$—, then the Ring B moiety can be substituted by up to three additional $R^8$ groups. In certain embodiments, the Ring B moiety is substituted by five $R^8$ groups. In certain embodiments, the Ring B moiety is substituted by four $R^8$ groups. In certain embodiments, the Ring B moiety is substituted by three $R^8$ groups. In certain embodiments, the Ring B moiety is substituted by two $R^8$ groups. In certain embodiments, the Ring B moiety is substituted by one $R^8$ group. In certain embodiments, the Ring B moiety is unsubstituted. In certain embodiments, the Ring B moiety is

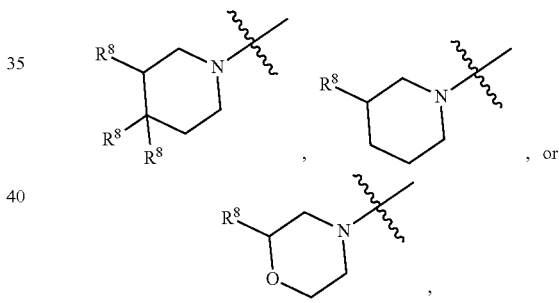

wherein each $R^8$ is independently as described herein.

In certain embodiments, each $R^7$ is independently hydrogen, $C_1$-$C_6$ alkyl, $C_1$-$C_6$ alkyl-OH, or $C_1$-$C_6$ haloalkyl. In certain embodiments, each $R^7$ is independently hydrogen, $C_1$-$C_3$ alkyl, $C_1$-$C_6$ alkyl-OH, or $C_1$-$C_3$ haloalkyl. In certain embodiments, each $R^7$ is independently hydrogen, —$CH_3$, —$CH_2OH$, or —$CF_3$.

In certain embodiments, both $R^7$ groups are hydrogen (H). In certain embodiments, one $R^7$ group is hydrogen. In certain embodiments, one $R^7$ group is hydrogen, and the other $R^7$ group is $C_1$-$C_6$ alkyl, $C_3$-$C_6$ alkyl-OH, or $C_1$-$C_6$ haloalkyl. In certain embodiments, one $R^7$ group is hydrogen and the other $R^7$ group is $C_1$-$C_6$ alkyl. In certain embodiments, one $R^7$ group is hydrogen and the other $R^7$ group is $C_1$-$C_6$ alkyl. In certain embodiments, one $R^7$ group is hydrogen and the other $R^7$ group is —$CH_3$.

In certain embodiments, $R^7$ is $C_1$-$C_6$ alkyl. In certain embodiments, $R^7$ is $C_1$-$C_3$ alkyl. In certain embodiments, $R^7$ is methyl, ethyl, n-propyl, or isopropyl. In certain embodiments, one $R^7$ group is methyl, ethyl, n-propyl, or isopropyl, and the other $R^7$ group is hydrogen. In certain embodiments, $R^7$ is —$CH_3$.

In certain embodiments, $R^7$ is $C_1$-$C_6$ alkyl-OH. In certain embodiments, $R^7$ is $C_1$-$C_3$ alkyl-OH. In certain embodiments, $R^7$ is —$CH_2OH$, —$CH_2CH_2$—OH, —$CH_2CH_2CH_2$—OH, or —$C(CH_3)_2$—OH. In certain embodiments, $R^7$ is —$CH_2OH$. In certain embodiments, one $R^7$ group is $C_1$-$C_6$ alkyl-OH, and the other $R^7$ group is hydrogen. In certain embodiments, one $R^7$ group is $C_1$-$C_3$ alkyl-OH, and the other $R^7$ group is hydrogen. In certain embodiments, one $R^7$ group is —$CH_2OH$, —$CH_2CH_2$—OH, —$CH_2CH_2CH_2$—OH, or —$C(CH_3)_2$—OH, and the other $R^7$ group is hydrogen. In certain embodiments, one $R^7$ group is —$CH_2OH$, and the other $R^7$ group is hydrogen.

In certain embodiments, $R^7$ is $C_1$-$C_6$ haloalkyl. In certain embodiments, $R^7$ is $C_1$-$C_6$ haloalkyl containing 1-7 halogen atoms. In certain embodiments, $R^7$ is $C_1$-$C_3$ haloalkyl. In certain embodiments, $R^7$ is $C_1$-$C_3$ haloalkyl containing 1-7 halogen atoms. In certain embodiments, $R^7$ is $C_1$-$C_3$ haloalkyl containing 1-5 halogen atoms. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, $R^7$ is —$CF_3$, —$CCl_3$, —$CF_2Cl$, —$CFCl_2$, —$CHF_2$, —$CH_2F$, —$CHCl_2$, —$CH_2F$, or —$CHFCl$. In certain embodiments, $R^7$ is —$CF_3$.

In certain embodiments, two $R^7$ groups are taken together with the carbon atom to which they are attached to form a $C_3$-$C_5$ cycloalkyl or 3- to 5-membered heterocyclyl. In certain embodiments, two $R^7$ groups are taken together with the carbon atom to which they are attached to form cyclopropyl or oxetanyl.

In certain embodiments, two $R^7$ groups are taken together with the carbon atom to which they are attached to form a $C_3$-$C_5$ cycloalkyl. In certain embodiments, two $R^7$ groups are taken together with the carbon atom to which they are attached to form cyclopropyl or cyclobutyl. In certain embodiments, two $R^7$ groups are taken together with the carbon atom to which they are attached to form cyclopropyl.

In certain embodiments, two $R^7$ groups are taken together with the carbon atom to which they are attached to form a 3- to 5-membered heterocyclyl. In certain embodiments, two $R^7$ groups are taken together with the carbon atom to which they are attached to form a 3- to 4-membered heterocyclyl. In certain embodiments, the heterocyclyl contains 1-3 heteroatoms selected from the group consisting of nitrogen, oxygen, and sulfur. In certain embodiments, the heterocyclyl contains one nitrogen atom. In certain embodiments, the heterocyclyl contains two nitrogen atoms. In certain embodiments, the heterocyclyl contains one oxygen atom. In certain embodiments, the heterocyclyl contains two oxygen atoms. In certain embodiments, the heterocyclyl contains one oxygen atom and one nitrogen atom. In certain embodiments, the heterocyclyl contains one sulfur atom. In certain embodiments, the heterocyclyl contains one nitrogen atom and one sulfur atom. In certain embodiments, $R^7$ is aziridinyl, oxiranyl, oxetanyl, azetidinyl, tetrahydrofuranyl, dioxolanyl, pyrrolidinyl, pyrazolidinyl, or isoxazolidinyl.

In certain embodiments, each $R^8$ is independently halo, $C_1$-$C_6$ alkyl, $C_1$-$C_6$ alkyl-CN, $C_1$-$C_6$ alkyl-OH, $C_1$-$C_6$ haloalkyl, —CN, oxo, or —$O(C_1$-$C_6$ alkyl). In certain embodiments, each $R^8$ is independently halo, $C_3$-$C_3$ alkyl, $C_1$-$C_6$ alkyl-CN, $C_3$-$C_6$ alkyl-OH, $C_1$-$C_6$ haloalkyl, —CN, oxo, or —$O(C_1$-$C_3$ alkyl). In certain embodiments, each $R^8$ is independently fluoro (F), —$CH_3$, —$CH_2CH_3$, —$CH_2CN$, —$CH_2OH$, —$CF_3$, —CN, oxo, or —$OCH_3$.

In certain embodiments, $R^8$ is halo. In certain embodiments, $R^8$ is chloro, fluoro, or bromo. In certain embodiments, $R^8$ is chloro or fluoro. In certain embodiments, $R^8$ is fluoro.

In certain embodiments, $R^8$ is $C_1$-$C_6$ alkyl. In certain embodiments, $R^8$ is $C_1$-$C_6$ alkyl. In certain embodiments, $R^8$ is methyl, ethyl, n-propyl, or isopropyl. In certain embodiments, $R^8$ is —$CH_3$ or —$CH_2CH_3$.

In certain embodiments, $R^8$ is —CN. In certain embodiments, $R^8$ is $C_1$-$C_6$ alkyl-CN. In certain embodiments, $R^8$ is $C_1$-$C_3$ alkyl-CN. In certain embodiments, $R^8$ is —$CH_2CN$, —$CH_2CH_2$—CN, —$CH_2CH_2CH_2$—CN, or —$C(CH_3)_2$—CN. In certain embodiments, $R^8$ is —$CH_2CN$.

In certain embodiments, $R^8$ is $C_1$-$C_6$ alkyl-OH. In certain embodiments, $R^8$ is $C_1$-$C_3$ alkyl-OH. In certain embodiments, $R^8$ is —$CH_2OH$, —$CH_2CH_2$—OH, —$CH_2CH_2CH_2$—OH, or —$C(CH_3)_2$—OH. In certain embodiments, $R^8$ is —$CH_2OH$.

In certain embodiments, $R^8$ is $C_1$-$C_6$ haloalkyl. In certain embodiments, $R^8$ is $C_1$-$C_6$ haloalkyl containing 1-7 halogen atoms. In certain embodiments, $R^8$ is $C_1$-$C_3$ haloalkyl. In certain embodiments, $R^8$ is $C_1$-$C_3$ haloalkyl containing 1-7 halogen atoms. In certain embodiments, $R^8$ is $C_1$-$C_3$ haloalkyl containing 1-5 halogen atoms. In certain embodiments, the halogen atoms are independently selected from the group consisting of chloro, bromo, and fluoro atoms. In certain embodiments, the halogen atoms are independently selected from the group consisting of chloro and fluoro atoms. In certain embodiments, the halogen atoms are all fluoro atoms. In certain embodiments, the halogen atoms are a combination of chloro and fluoro atoms. In certain embodiments, $R^8$ is —$CF_3$, —$CCl_3$, —$CF_2Cl$, —$CFCl_2$, —$CHF_2$, —$CH_2F$, —$CHCl_2$, —$CH_2F$, or —$CHFCl$. In certain embodiments, $R^8$ is —$CF_3$.

In certain embodiments, $R^8$ is oxo.

In certain embodiments, $R^8$ is —$O(C_1$-$C_6$ alkyl). In certain embodiments, $R^8$ is —$O$—$(C_1$-$C_3$ alkyl). In certain embodiments, $R^8$ is —$O$(methyl), —$O$(ethyl), —$O$(n-propyl), or —$O$(isopropyl). In certain embodiments, $R^8$ is —$OCH_3$ or —$OCH_2CH_3$. In certain embodiments, $R^8$ is —$OCH_3$.

In certain embodiments, two $R^8$ groups are taken together with the carbon atom or atoms to which they are attached to form a spiro or fused $C_3$-$C_5$ cycloalkyl or 3- to 5-membered heterocyclyl. In certain embodiments, two $R^8$ groups are taken together with the carbon atom or atoms to which they are attached to form a spiro or fused cyclopropyl or oxetanyl.

In certain embodiments, two $R^8$ groups are taken together with the carbon atom or atoms to which they are attached to form a spiro or fused $C_3$-$C_{65}$cycloalkyl. In certain embodiments, two $R^8$ groups are taken together with the carbon atom or atoms to which they are attached to form a spiro $C_3$-$C_5$ cycloalkyl. In certain embodiments, two $R^8$ groups are taken together with the carbon atom or atoms to which they are attached to form a spiro cyclopropyl. In certain embodiments, two $R^8$ groups are taken together with the carbon atom or atoms to which they are attached to form a spiro cyclobutyl. In certain embodiments, two $R^8$ groups are taken together with the carbon atom or atoms to which they are attached to form a spiro cyclopentyl. In certain embodiments, two $R^8$ groups are taken together with the carbon atom or atoms to which they are attached to form a fused $C_3$-$C_5$ cycloalkyl. In certain embodiments, two $R^8$ groups are taken together with the carbon atom or atoms to which they are attached to form a fused cyclopropyl. In certain embodiments, two $R^8$ groups are taken together with the carbon atom or atoms to which they are attached to form a fused cyclobutyl. In certain embodiments, two $R^8$ groups are taken together with the carbon atom or atoms to which they are attached to form a fused cyclopentyl. In certain embodiments, two $R^8$ groups are taken together with the carbon atom or atoms to which they are attached to form a spiro or fused cyclopropyl.

In certain embodiments, two $R^8$ groups are taken together with the carbon atom or atoms to which they are attached to form a spiro or fused 3- to 5-membered heterocyclyl. In certain embodiments, two $R^8$ groups are taken together with the carbon atom or atoms to which they are attached to form a spiro 3- to 5-membered heterocyclyl. In certain embodiments, two $R^8$ groups are taken together with the carbon atom or atoms to which they are attached to form a spiro oxetanyl. In certain embodiments, two $R^8$ groups are taken together with the carbon atom or atoms to which they are attached to form a fused 3- to 5-membered heterocyclyl. In certain embodiments, two $R^8$ groups are taken together with the carbon atom or atoms to which they are attached to form a fused oxetanyl. In certain embodiments, two $R^8$ groups are taken together with the carbon atom or atoms to which they are attached to form a spiro or fused oxetanyl. In certain embodiments, the heterocyclyl contains 1-3 heteroatoms selected from the group consisting of nitrogen, oxygen, and sulfur. In certain embodiments, the heterocyclyl contains one nitrogen atom. In certain embodiments, the heterocyclyl contains two nitrogen atoms. In certain embodiments, the heterocyclyl contains one oxygen atom. In certain embodiments, the heterocyclyl contains two oxygen atoms. In certain embodiments, the heterocyclyl contains one oxygen atom and one nitrogen atom. In certain embodiments, the heterocyclyl contains one sulfur atom. In certain embodiments, the heterocyclyl contains one nitrogen atom and one sulfur atom. In certain embodiments, two $R^8$ groups are taken together with the carbon atom to which they are attached to form a spiro aziridinyl, oxiranyl, oxetanyl, azetidinyl, tetrahydrofuranyl, dioxolanyl, pyrrolidinyl, pyrazolidinyl, or isoxazolidinyl. In certain embodiments, two $R^8$ groups are taken together with the carbon atoms to which they are attached to form a fused aziridinyl, oxiranyl, oxetanyl, azetidinyl, tetrahydrofuranyl, dioxolanyl, pyrrolidinyl, pyrazolidinyl, or isoxazolidinyl.

In certain embodiments, X is

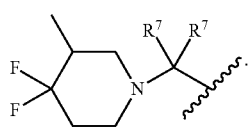

In certain embodiments, X is

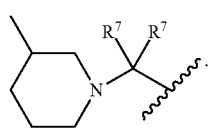

In certain embodiments, X is

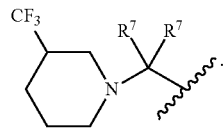

In certain embodiments, X is

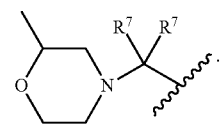

In certain embodiments, X is

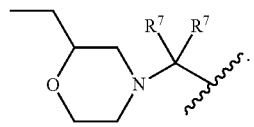

In certain embodiments, X is

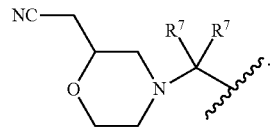

In any of these embodiments, both $R^7$ groups can be hydrogen (H). In any of these embodiments, one $R^7$ group can be hydrogen and one $R^7$ group can be $CH_3$. In any of these embodiments, both $R^7$ groups can be —$CH_3$.

In certain embodiments, the compound is of Formula (I-A) or (I-B):

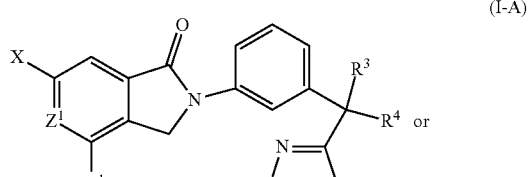

(I-A)

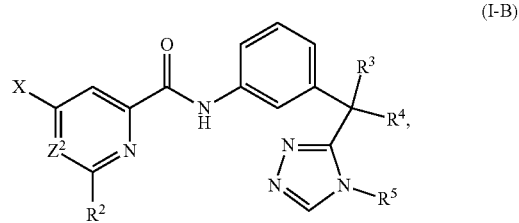

(I-B)

wherein $R^1$, $R^2$, $R^3$, $R^4$, $R^5$, $Z^1$, $Z^2$, and X are as described for the compound of Formula (I).

In certain embodiments, the compound is of Formula (I-a) or (I-b):

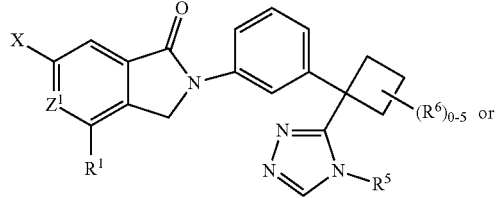
(I-a)

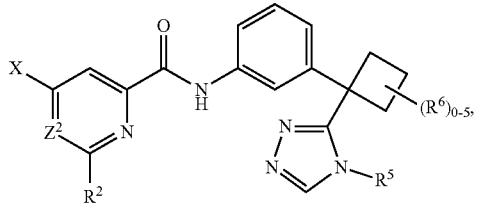
(I-b)

wherein $R^1$, $R^2$, $R^5$, $R^6$, $Z^1$, $Z^2$, and X are as described for the compound of Formula (I).

In certain embodiments, the compound is of Formula (I-C), (I-D), (I-E), (I-F), (I-G), (I-H), or (I-J):

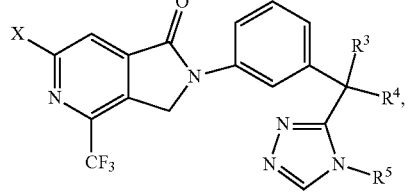
(I-C)

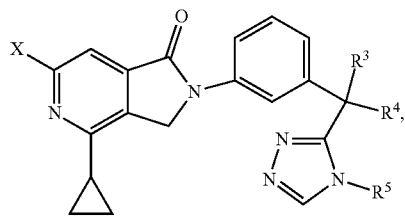
(I-D)

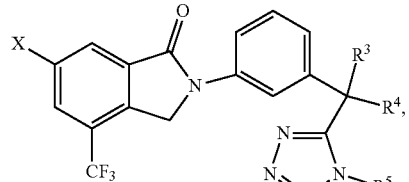
(I-E)

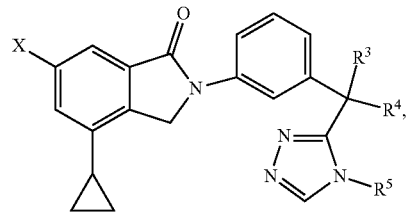
(I-F)

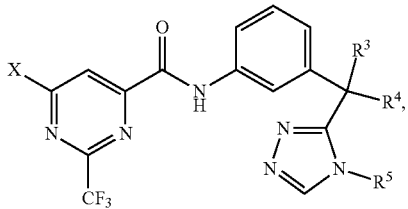
(I-G)

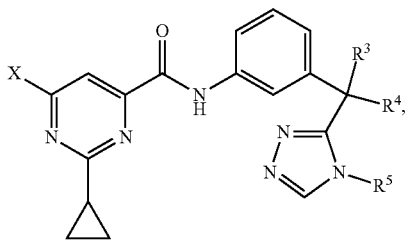
(I-H)

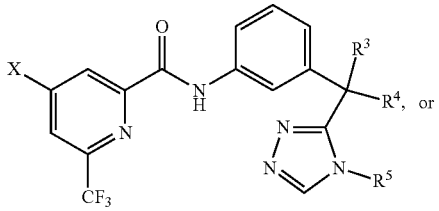
(I-I)

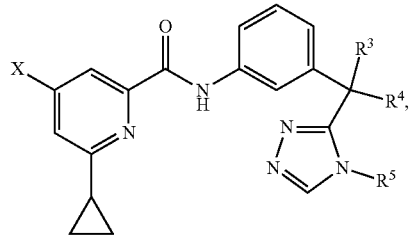
(I-J)

wherein $R^3$, $R^4$, $R^5$, and X are as described for the compound of Formula (I).

In certain embodiments, the compound is of Formula (II-A), (II-B), (II-C), (II-D), (II-E), (II-F), (II-G), or (II-H):

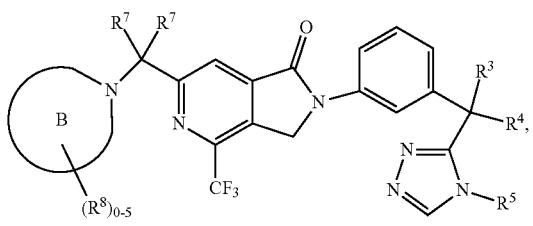
(II-A)

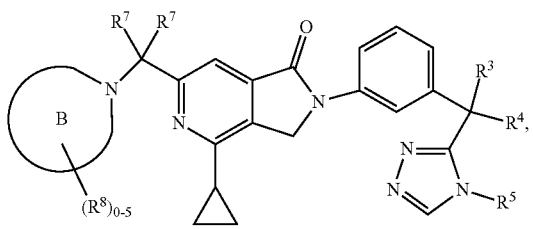
(II-B)

-continued
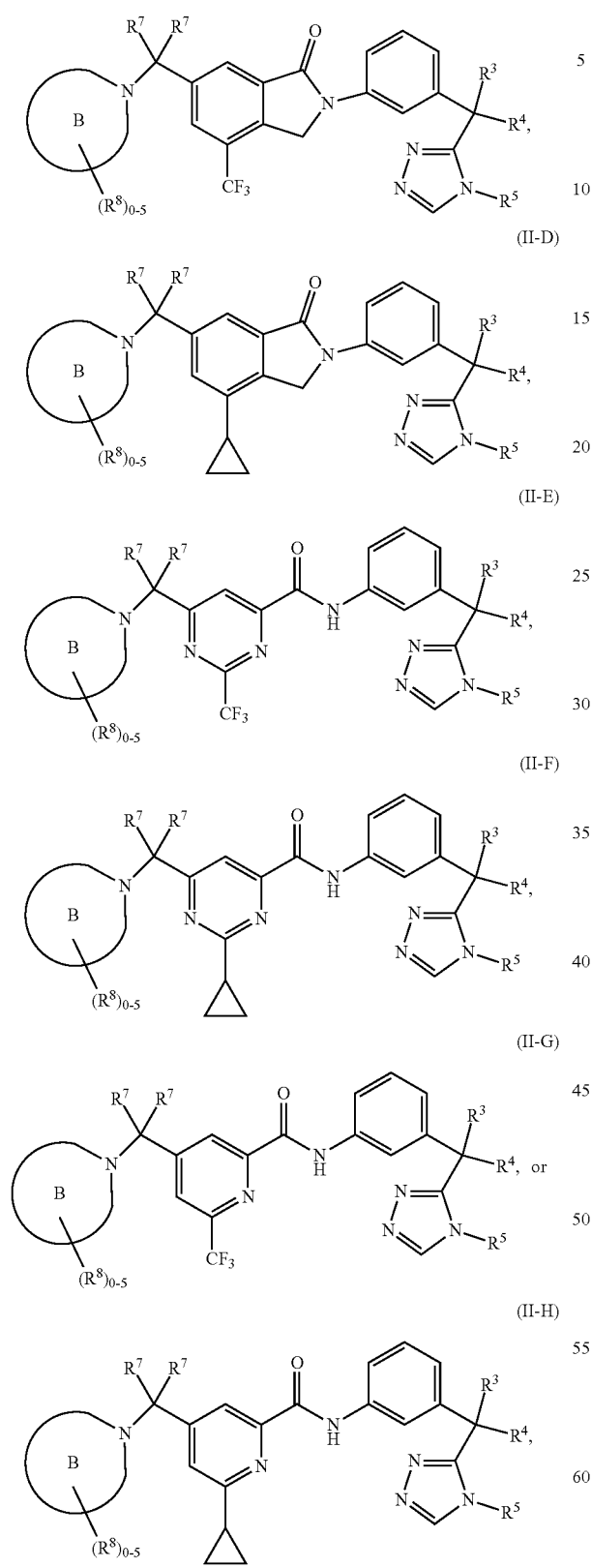
wherein $R^3$, $R^4$, $R^5$, $R^7$, $R^8$, and the Ring B moiety are as described for the compound of Formula (I).
In certain embodiments, the compound is of Formula (III-A), (III-B), (III-C), (III-D), (III-E), (III-F), (III-G), or (III-H):
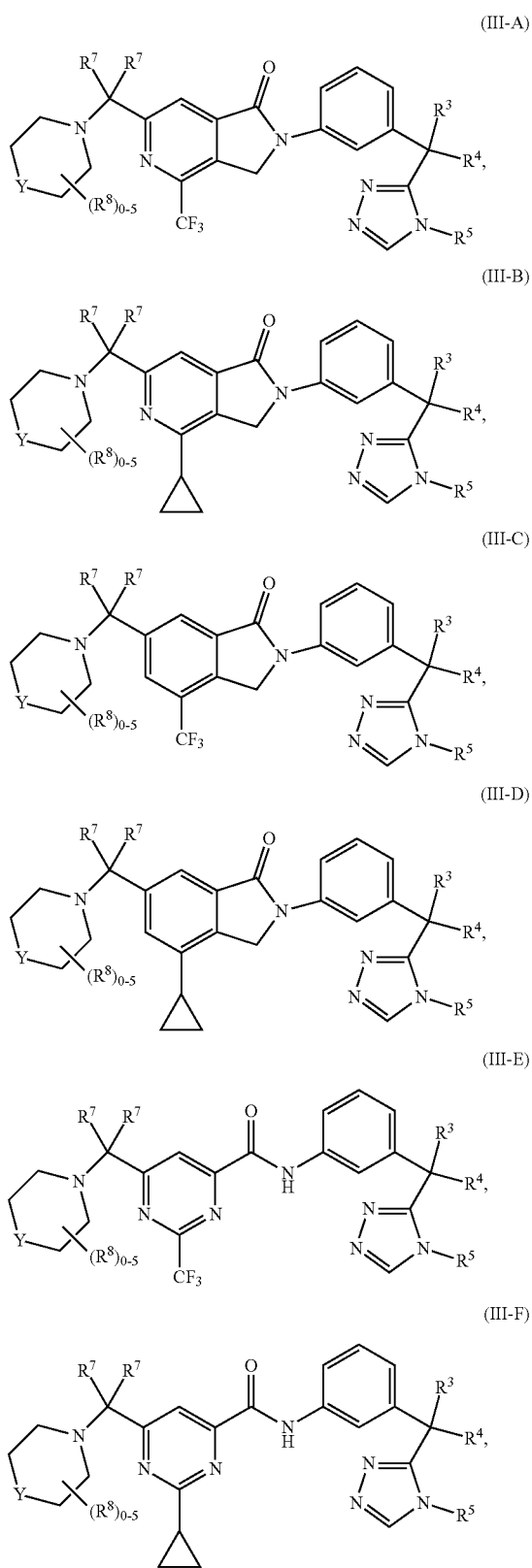

(III-G)
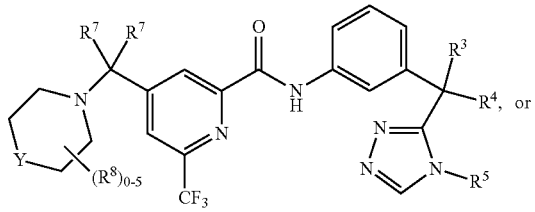

(III-H)
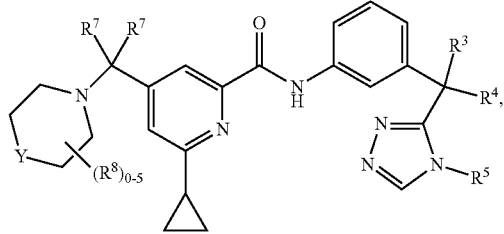

wherein $R^3$, $R^4$, $R^5$, $R^7$, $R^8$, and Y are as described for the compound of Formula (I).

In certain embodiments, the compound is of Formula (IV-A), (IV-B), (IV-C), (IV-D), (IV-E), (IV-F), (IV-G), or (IV-H):

(IV-A)
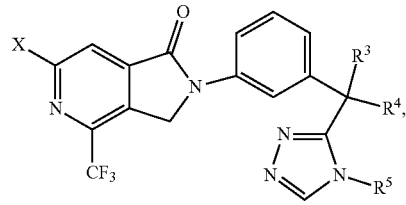

(IV-B)
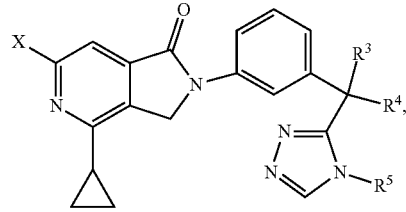

(IV-C)
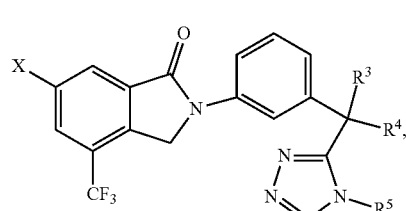

(IV-D)
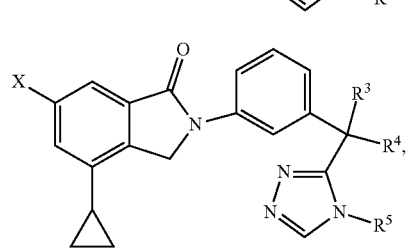

(IV-E)
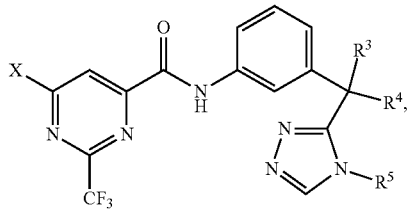

(IV-F)

(IV-G)

(IV-H)
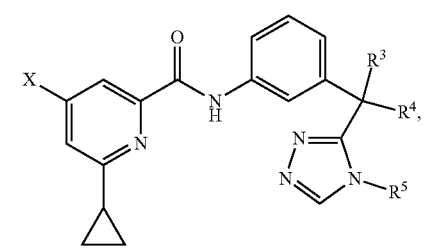

wherein $R^3$, $R^4$, and $R^5$ are as described for the compound of Formula (I), and X is hydrogen, $C_1$-$C_6$ alkyl, $C_1$-$C_6$ haloalkyl, $C_1$-$C_6$ alkyl-OH, $C_1$-$C_6$ alkyl-CN, or $C_3$-$C_6$ cycloalkyl optionally substituted by 1-5 $R^8$ groups. In certain embodiments, X is hydrogen. In certain embodiments, X is $C_1$-$C_6$ alkyl. In certain embodiments, X is $C_1$-$C_6$ haloalkyl. In certain embodiments, X is $C_1$-$C_6$ alkyl-OH. In certain embodiments, X is $C_1$-$C_6$ alkyl-CN. In certain embodiments, X is $C_3$-$C_6$ cycloalkyl optionally substituted by 1-5 $R^8$ groups.

In certain embodiments, the compound is from Table 1, or a pharmaceutically acceptable stereoisomer, tautomer, or salt thereof.

TABLE 1

Representative Compounds of This Disclosure

| Cmpd No. | Structure |
|---|---|
| 1 | |
| 2 | |
| 3 | |
| 4 | |
| 5 | |
| 6 | |
| 7 | 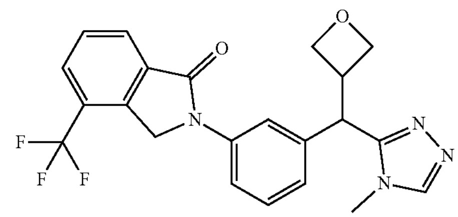 [SMILES: Cn1cnnc1C(c1cccc(N2Cc3c(cccc3C(F)(F)F)C2=O)c1)C1COC1] |
| 8 | 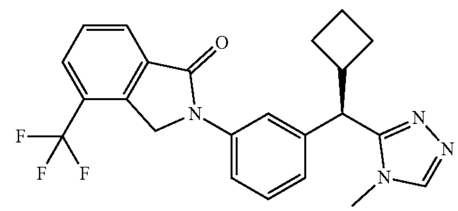 [SMILES: Cn1cnnc1[C@@H](c1cccc(N2Cc3c(cccc3C(F)(F)F)C2=O)c1)C1CCC1] |
| 9 | 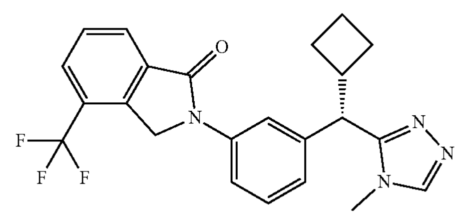 [SMILES: Cn1cnnc1[C@H](c1cccc(N2Cc3c(cccc3C(F)(F)F)C2=O)c1)C1CCC1] |
| 10 | 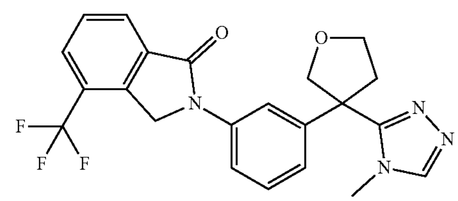 [SMILES: Cn1cnnc1C1(c2cccc(N3Cc4c(cccc4C(F)(F)F)C3=O)c2)CCOC1] |
| 11 | 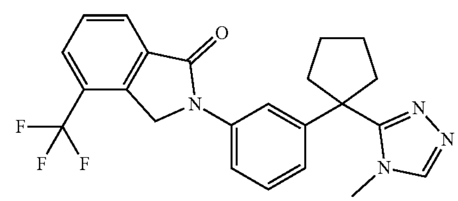 [SMILES: Cn1cnnc1C1(c2cccc(N3Cc4c(cccc4C(F)(F)F)C3=O)c2)CCCC1] |
| 12 | 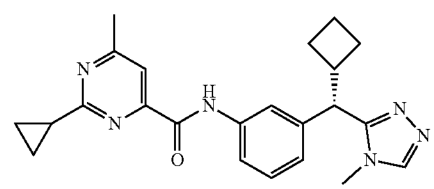 [SMILES: Cc1cc(C(=O)Nc2cccc([C@@H](c3nncn3C)C3CCC3)c2)nc(C2CC2)n1] |
| 13 | 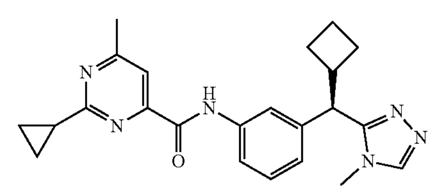 [SMILES: Cc1cc(C(=O)Nc2cccc([C@H](c3nncn3C)C3CCC3)c2)nc(C2CC2)n1] |

TABLE 1-continued
Representative Compounds of This Disclosure
| Cmpd No. | Structure |
|---|---|
| 14 | 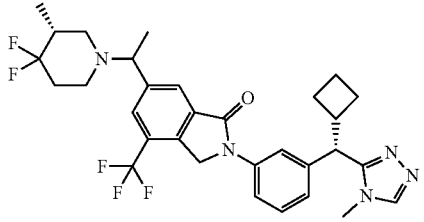 [SMILES: CC(c1cc2c(c(C(F)(F)F)c1)CN(c1cccc([C@@H](c3nncn3C)C3CCC3)c1)C2=O)N1CCC(F)(F)[C@H](C)C1] |
| 15 | 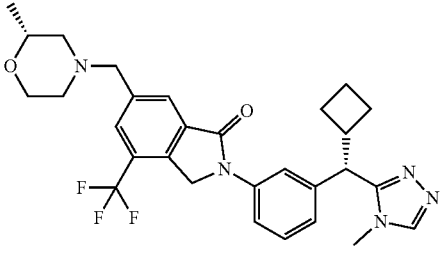 [SMILES: C[C@@H]1CN(Cc2cc3c(c(C(F)(F)F)c2)CN(c2cccc([C@@H](c4nncn4C)C4CCC4)c2)C3=O)CCO1] |
| 16 | 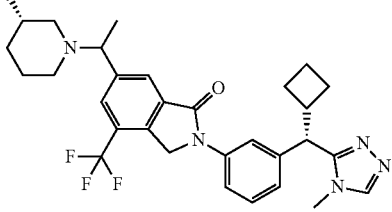 |
| 17 | 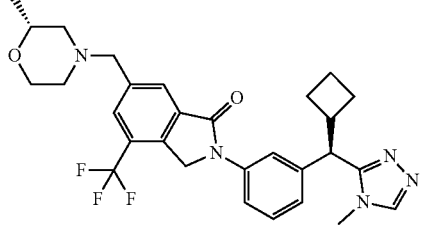 |
| 18 | 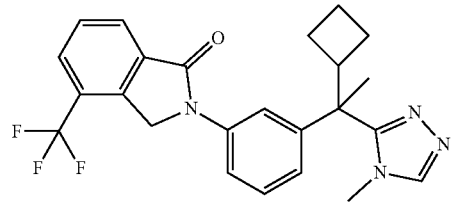 [SMILES: Cn1cnnc1C(C)(c1cccc(N2Cc3c(cccc3C(F)(F)F)C2=O)c1)C1CCC1] |
| 19 | 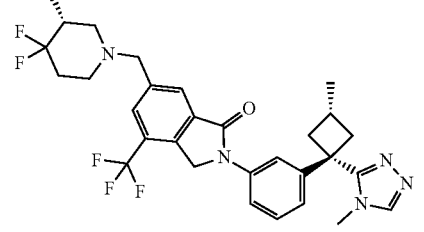 |
| 20 | 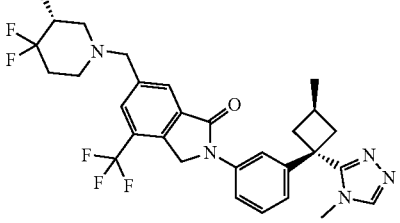 |
| 21 | 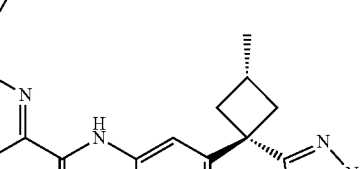 |
| 22 | 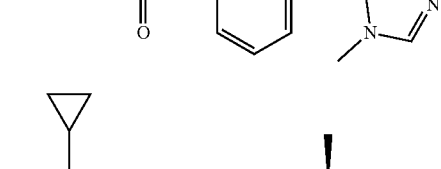 |
| 23 | 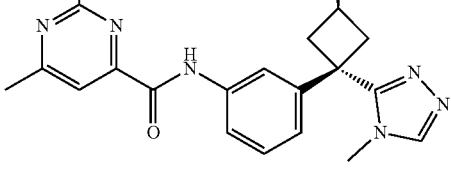 |
| 24 | 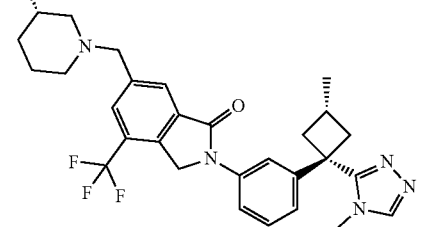 |
| 25 | 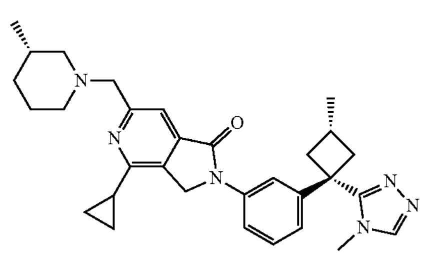 [SMILES: C[C@H]1CCCN(Cc2cc3c(c(C4CC4)n2)CN(c2cccc([C@]4(c5nncn5C)C[C@@H](C)C4)c2)C3=O)C1] |

TABLE 1-continued
Representative Compounds of This Disclosure
| Cmpd No. | Structure |
|---|---|
| 26 | 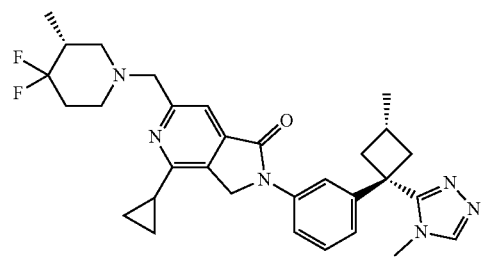 [SMILES: C[C@@H]1CN(Cc2cc3c(c(C4CC4)n2)CN(c2cccc([C@]4(c5nncn5C)C[C@@H](C)C4)c2)C3=O)CCC1(F)F] |
| 27 | 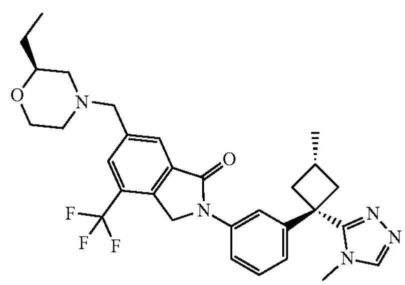 [SMILES: CC[C@H]1CN(Cc2cc3c(c(C(F)(F)F)c2)CN(c2cccc([C@]4(c5nncn5C)C[C@@H](C)C4)c2)C3=O)CCO1] |
| 28 | 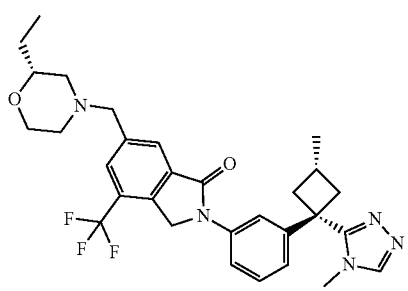 [SMILES: CC[C@@H]1CN(Cc2cc3c(c(C(F)(F)F)c2)CN(c2cccc([C@]4(c5nncn5C)C[C@@H](C)C4)c2)C3=O)CCO1] |
| 29 | 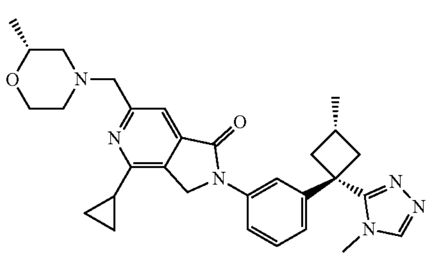 [SMILES: C[C@@H]1CN(Cc2cc3c(c(C4CC4)n2)CN(c2cccc([C@]4(c5nncn5C)C[C@@H](C)C4)c2)C3=O)CCO1] |
| 30 | 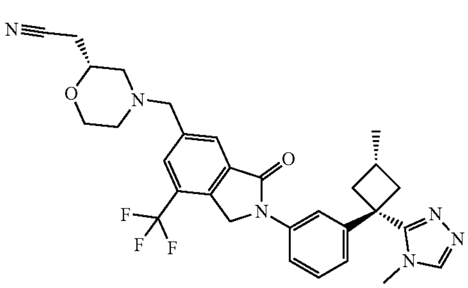 [SMILES: Cn1cnnc1[C@]1(c2cccc(N3Cc4c(cc(CN5CCO[C@H](CC#N)C5)cc4C(F)(F)F)C3=O)c2)C[C@H](C)C1] |
TABLE 1-continued
Representative Compounds of This Disclosure
| Cmpd No. | Structure |
|---|---|
| 31 | 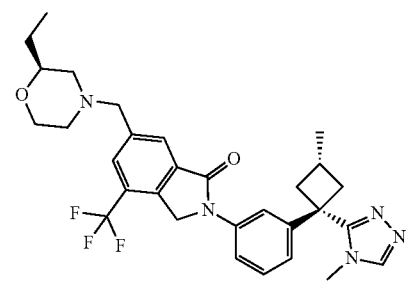 |
| 32 | 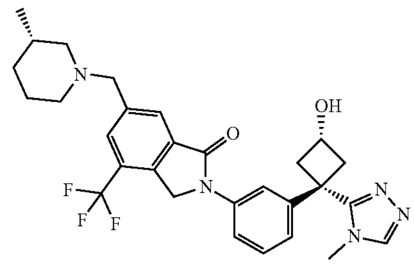 [SMILES: C[C@H]1CCCN(Cc2cc3c(c(C(F)(F)F)c2)CN(c2cccc([C@]4(c5nncn5C)C[C@@H](O)C4)c2)C3=O)C1] |
| 33 | 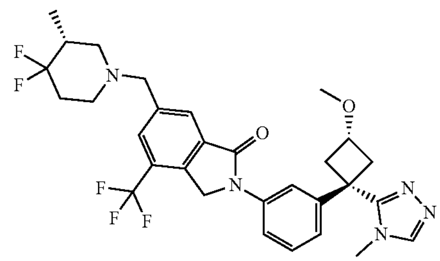 [SMILES: CO[C@H]1C[C@@](c2cccc(N3Cc4c(cc(CN5CCC(F)(F)[C@H](C)C5)cc4C(F)(F)F)C3=O)c2)(c2nncn2C)C1] |
| 34 | 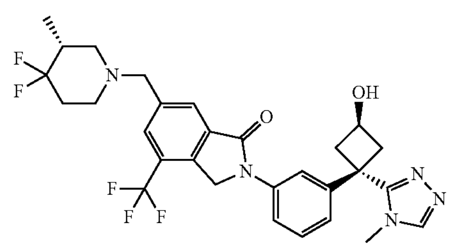 [SMILES: C[C@@H]1CN(Cc2cc3c(c(C(F)(F)F)c2)CN(c2cccc([C@]4(c5nncn5C)C[C@H](O)C4)c2)C3=O)CCC1(F)F] |
| 35 | 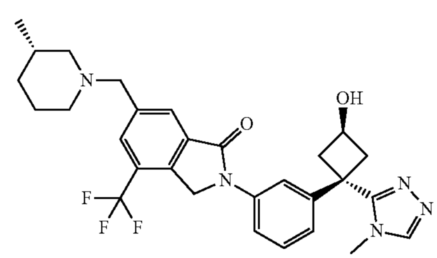 [SMILES: C[C@H]1CCCN(Cc2cc3c(c(C(F)(F)F)c2)CN(c2cccc([C@]4(c5nncn5C)C[C@H](O)C4)c2)C3=O)C1] |
| 36 | 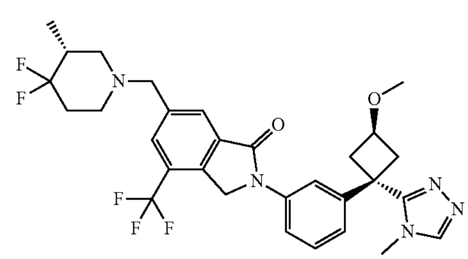 [SMILES: CO[C@H]1C[C@](c2cccc(N3Cc4c(cc(CN5CCC(F)(F)[C@H](C)C5)cc4C(F)(F)F)C3=O)c2)(c2nncn2C)C1] |

TABLE 1-continued
Representative Compounds of This Disclosure
| Cmpd No. | Structure |
|---|---|
| 37 | 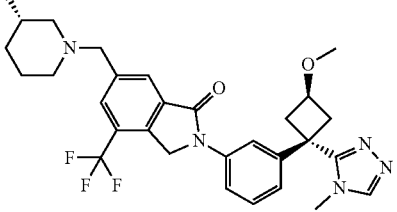 |
| 38 | 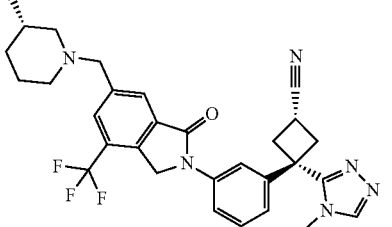 |
| 39 | 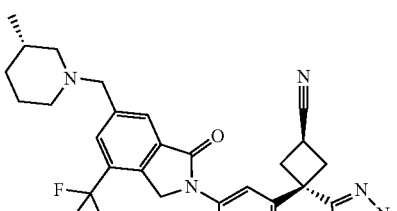 |
| 40 | 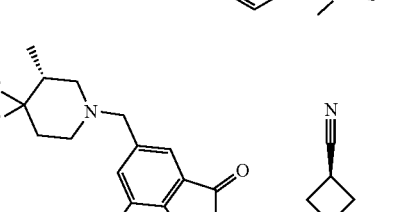 |
| 41 | 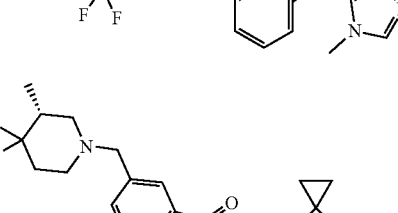 |
| 42 | 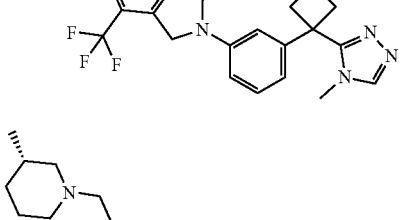 |
| 43 | 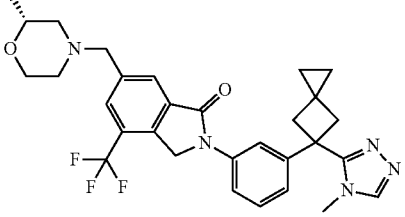 |
| 44 | 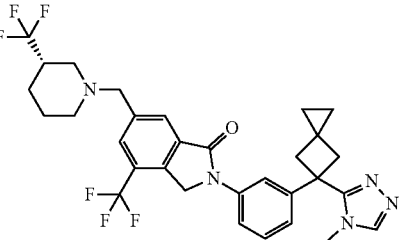 |
| 45 | 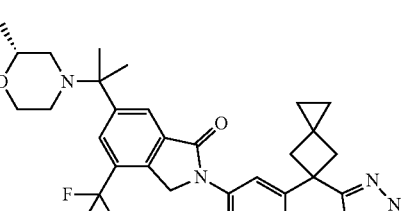 |
| 46 | 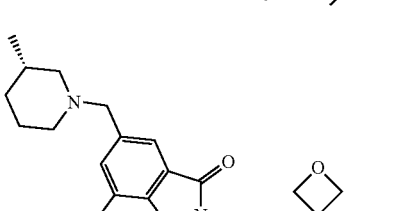 |
| 47 | 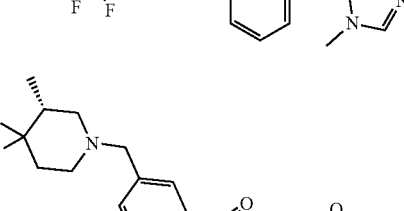 |
| 48 | 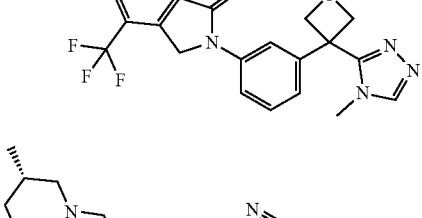 |

TABLE 1-continued

Representative Compounds of This Disclosure

| Cmpd No. | Structure |
|---|---|
| 49 | *(chemical structure)* |
| 50 | *(chemical structure)* |
| 51 | *(chemical structure)* |
| 52 | *(chemical structure)* |
| 53 | *(chemical structure)* |

3. Combinations

Given the mechanism of Cbl-b, particularly effective combinations for the treatment of cancer include a Cbl-b inhibitor with a second anti-cancer agent that enhances the effector function of immune cells. In certain embodiments, the second anti-cancer agent mediates its effect through T-cells or natural killer (NK) cells, a combination with a Cbl-B inhibitor is even more favorable. In certain embodiments, the combination is synergistic.

In certain embodiments, the second anti-cancer agent is a checkpoint inhibitor. Checkpoint inhibitors include compounds that impede the immune checkpoint, a signaling pathway that suppresses the activation of immune cells such as T-cells, NK cells, or macrophages. The most well-known checkpoint inhibitors are binding antagonists against a T-cell target. Illustrative examples of T-cell checkpoint inhibitors include CTLA-4 axis antagonists, LAG3 binding antagonists, PD-1 axis antagonists, TIGIT binding antagonists, TIM3 binding antagonists, and VISTA binding antagonists. An illustrative example of a macrophage checkpoint inhibitor is a CD47 binding antagonist.

In certain embodiments, the second anti-cancer agent is a PARP inhibitor (PARPi). PARP inhibitors include compounds that repair DNA when the DNA becomes damaged. For example, PARP-based therapies work through the inhibition of single-strand DNA repair leading to genomic instability, increased tumor mutational burden, neoantigen release, and enhancement of PD-L1 expression making the tumor more responsive to immunotherapy.

In certain embodiments, the second anti-cancer agent is a taxane. Taxanes include compounds that terminate mitosis via interference with microtubules. For example, the anti-tumor activity of certain chemotherapy agents such as taxanes is now thought to involve the induction of immunogenic cell death of cancer cells leading to the presentation of novel tumor-specific antigens and an adaptive T-cell response [Miura et al. (2014) J Nippon Med Sch. 81: 211-220; Lau et al. (2020) Cancer Immunol Res. 8: 1099-111]. For instance, paclitaxel induced anti-tumor activity has also been shown to promote infiltration and activation of NK cells in the tumor microenvironment [Garafolo et al. (2021) Front. Oncol. 11: 1-19].

In certain embodiments, the second anti-cancer agent is an agent that triggers antibody-dependent cellular cytotoxicity (ADCC). Also referred to as antibody-dependent cell-mediated cytotoxicity, ADCC is whereby an immune effector cell binds to antibodies on a target cell thereby lysing it. In a particular embodiment, the second anti-cancer agent triggers NK cell-mediated ADCC. Illustrative examples of ADCC triggering agents include anti-CD20 binding antagonists and HER2 binding antagonists. In particular embodiments, the ADCC triggering agent is rituximab. In particular embodiments, the ADCC triggering agent is ofatumumab. In particular embodiments, the ADCC triggering agent is trastuzumab.

Provided herein are Cbl-b inhibitor compounds for use in combination with a second anti-cancer agent. Generally, the Cbl-b inhibitor compound and the second anti-cancer agent are administered according to their own doses and schedules. Thus, in certain embodiments, the Cbl-b inhibitor compound is administered at a dose and schedule deemed useful by the practitioner of skill. In certain embodiments, the second anti-cancer agent is administered at a dose and schedule deemed useful by the practitioner of skill. In particular embodiments, the second anti-cancer agent is administered according to its labelled instruction.

In certain embodiments, the amount of the Cbl-b inhibitor compound is therapeutically effective. In certain embodiments, the amount of the second anti-cancer agent is therapeutically effective. In certain embodiments, the amount of the Cbl-b inhibitor compound is therapeutically effective, and the amount of the second anti-cancer agent is therapeutically effective. In certain embodiments, the amount of the Cbl-b inhibitor compound is sub-therapeutic. In certain embodiments, the amount of the second anti-cancer agent is sub-therapeutic. In certain embodiments, the amount of the Cbl-b inhibitor compound is sub-therapeutic, and the amount of the second anti-cancer agent is sub-therapeutic. In certain sub-therapeutic embodiments, the combination is therapeutic while one or more components are at sub-therapeutic doses.

In certain embodiments, the Cbl-b inhibitor compound and the second anti-cancer agent are administered consecutively in either order. As used herein, the terms "consecutively," "serially," and "sequentially" refer to administration of a Cbl-b inhibitor compound after a second anti-cancer agent, or administration of the second anti-cancer agent after the Cbl-b inhibitor compound. For instance, consecutive administration may involve administration of the Cbl-b inhibitor compound in the absence of the second anti-cancer agent during an induction phase (primary therapy), which is followed by a post-induction treatment phase comprising administration of the second anti-cancer agent. The methods may further comprise a maintenance phase comprising administration of the Cbl-b inhibitor compound or the second anti-cancer agent, or both. Alternatively, consecutive administration may involve administration of the second anti-cancer agent in the absence of the Cbl-b inhibitor compound during an induction phase (primary therapy), which is followed by a post-induction treatment phase comprising administration of the Cbl-b inhibitor compound. The methods may further comprise a maintenance phase comprising administration of the Cbl-b inhibitor compound or the second anti-cancer agent, or both.

In certain embodiments, the Cbl-b inhibitor compound and the second anti-cancer agent are administered concurrently. As used herein, the terms "concurrently," "simultaneously," and "in parallel" refer to administration of a Cbl-b inhibitor compound and a second anti-cancer agent during the same doctor visit or during the same phase of treatment. For instance, both the Cbl-b inhibitor compound and the second anti-cancer agent may be administered during one or more of an induction phase, a treatment phase, and a maintenance phase. However, concurrent administration does not require that the Cbl-b inhibitor compound and the second anti-cancer agent be present together in a single formulation or pharmaceutical composition, or that the Cbl-b inhibitor compound and the second anti-cancer agent be administered at precisely the same time.

In certain embodiments, a combination provided herein can be administered directly to an individual to treat cancer in the individual.

In certain embodiments, provided herein is a method of treating cancer, the method comprising administering an effective amount of a combination provided herein to an individual to treat cancer in the individual. In certain embodiments, the individual has a cancer such as a hematologic cancer or non-hematological cancer described herein.

In certain embodiments, provided herein is a method of treating cancer responsive to inhibition of Cbl-b activity, the method comprising administering an effective amount of a combination provided herein to an individual to treat the cancer responsive to inhibition of Cbl-b activity. In certain embodiments, the cancer is a hematologic cancer or non-hematological cancer such as one described herein.

In certain embodiments, provided herein is a method of treating cancer responsive to checkpoint inhibition, the method comprising administering an effective amount of a combination provided herein to an individual to treat the cancer responsive to checkpoint inhibition. In certain embodiments, the cancer is a hematologic cancer or non-hematological cancer such as one described herein.

In certain embodiments, provided herein is a method of treating cancer responsive to PARP inhibition, the method comprising administering an effective amount of a combination provided herein to an individual to treat the cancer responsive to PARP inhibition. In certain embodiments, the cancer is a hematologic cancer or non-hematological cancer such as one described herein.

In certain embodiments, provided herein is a method of treating cancer responsive to a taxane, the method comprising administering an effective amount of a combination provided herein to an individual to treat the cancer responsive to a taxane. In certain embodiments, the cancer is a hematologic cancer or non-hematological cancer such as one described herein.

In certain embodiments, provided herein is a method of treating cancer that is nonresponsive to checkpoint inhibition alone, the method comprising administering an effective amount of a combination provided herein to such an individual to treat the cancer nonresponsive to checkpoint inhibition. In certain embodiments, the cancer is a hematologic cancer or non-hematological cancer such as one described herein.

The Cbl-b inhibitor compound or composition thereof is suitably administered to the individual at one time or over a series of treatments. In certain embodiments, the treatment includes multiple administrations of the Cbl-b inhibitor compound or composition, wherein the interval between administrations may vary. For example, the interval between the first administration and the second administration is about one month, and the intervals between the subsequent administrations are about three months. In certain embodiments, a Cbl-b inhibitor compound is administered at a flat dose. In certain embodiments, a Cbl-b inhibitor compound described herein is administered to an individual at a fixed dose based on the individual's weight (e.g., mg/kg).

The second anti-cancer agent or composition thereof is suitably administered to the individual at one time or over a series of treatments. In certain embodiments, the treatment includes multiple administrations of the second anti-cancer agent or composition, wherein the interval between administrations may vary. For example, the interval between the first administration and the second administration is about one month, and the intervals between the subsequent administrations are about three months. In certain embodiments, a second anti-cancer agent is administered at a flat dose. In certain embodiments, a second anti-cancer agent is administered to an individual at a fixed dose based on the individual's weight (e.g., mg/kg).

In certain embodiments of this disclosure, the cancer is a hematologic cancer. For example, the hematologic cancer may be a lymphoma, a leukemia, or a myeloma. In other aspects of this disclosure, the cancer is a non-hematologic cancer. In particular, the non-hematologic cancer may be a carcinoma, a sarcoma, or a melanoma.

In certain embodiments, the effectiveness of the combination in the methods herein (e.g., method of modulating an immune response in an individual) can be assessed by measuring the biological activity of immune cells present in a sample (e.g., blood sample) isolated from the treated individual. For example, the ability of immune cells isolated from the individual after treatment with a combination provided herein to destroy target cells in a cytotoxicity assay may be measured to assess treatment efficacy. In certain embodiments, the biological activity of immune cells pres-

4. Second Anti-Cancer Agents

In certain embodiments, the second anti-cancer agent is a checkpoint inhibitor. In certain embodiments, the second anti-cancer agent is an agent that triggers NK cell-mediated antibody-dependent cytotoxicity (ADCC). In certain embodiments, the second anti-cancer agent is a PARP inhibitor. In certain embodiments, the second anti-cancer agent is a taxane.

In certain embodiments, the second anti-cancer agent is a T-cell checkpoint inhibitor. In certain embodiments, the second anti-cancer agent is a CTLA-4 axis antagonist. In certain embodiments, the second anti-cancer agent is a CTLA-4 binding antagonist. Useful CTLA-4 antagonists include ipilimumab. In certain embodiments, the second anti-cancer agent is a LAG3 axis antagonist. In certain embodiments, the second anti-cancer agent is a LAG3 binding antagonist. Useful LAG3 antagonists include relatlimab (Bristol Meyers) and fianlimab (Regeneron). In certain embodiments, the second anti-cancer agent is a PD-1 axis antagonist. In certain embodiments, the second anti-cancer agent is a PD-1 binding antagonist. Useful PD-1 antagonists are described below. In certain embodiments, the second anti-cancer agent is a TIGIT axis antagonist. In certain embodiments, the second anti-cancer agent is a TIGIT binding antagonist. Useful TIGIT antagonists include BMS-986207 (Bristol Meyers). In certain embodiments, the second anti-cancer agent is a TIM3 axis antagonist. In certain embodiments, the second anti-cancer agent is a TIM3 binding antagonist. Useful TIGIT antagonists include BMS-986258 (Bristol Meyers). In certain embodiments, the second anti-cancer agent is a VISTA axis antagonist. In certain embodiments, the second anti-cancer agent is a VISTA binding antagonist.

In certain embodiments, the second anti-cancer agent is a macrophage checkpoint inhibitor. In certain embodiments, the second anti-cancer agent is a CD47 axis antagonist. In certain embodiments, the second anti-cancer agent is a CD47 binding antagonist. Useful CD47 antagonists include CC-90002 (Celgene).

In certain embodiments, the second anti-cancer agent is an agent that triggers NK-mediated ADCC. In certain embodiments, the second anti-cancer agent is a HER2 inhibitor. In certain embodiments, the second anti-cancer agent is a HER2 axis antagonist. In certain embodiments, the second anti-cancer agent is a HER2 binding antagonist. Useful HER2 antagonists include neratinib, trastuzumab, dacomitinib, lapatinib, tucatinib, pertuzumab, margetuximab, ado-trastuzumab emtansine, and fam-trastuzumab deruxtecan. In certain embodiments, the second anti-cance agent is a CD20 inhibitor. In certain embodiments, the second anti-cancer agent is a CD20 axis antagonist. In certain embodiments, the second anti-cancer agent is a CD20 binding antagonist. Useful CD20 antagonists include ocrelizumab, rituximab, ofatumumab, and ibritumomab.

In certain embodiments, the second anti-cancer agent is a PARP inhibitor selected from the group consisting of olaparib, talazoparib, and niraparib.

In certain embodiments, the second anti-cancer agent is a taxane selected from the group consisting of paclitaxel and docetaxel.

In the combinations provided herein, the PD-1 axis antagonist can be any PD-1 axis antagonist known to the practitioner of skill. In certain embodiments, the PD-1 axis antagonist is a small molecule. In certain embodiments, the PD-1 axis antagonist is an antibody. In certain embodiments, the PD-1 axis antagonist binds PD-1. In certain embodiments, the PD-1 axis antagonist binds PD-L1. In certain embodiments, the PD-1 axis antagonist binds PD-L2. In certain embodiments, the PD-1 axis antagonist inhibits PD-1 activity. In certain embodiments, the PD-1 axis antagonist inhibits PD-L1 activity. In certain embodiments, the PD-1 axis antagonist inhibits PD-L2 activity.

In certain embodiments, the PD-1 binding antagonist is a molecule that inhibits the binding of PD-1 to its ligand binding partners. In certain embodiments, the PD-1 ligand binding partners are PD-L1 and/or PD-L2. In another embodiment, the PD-L1 binding antagonist is a molecule that inhibits the binding of PD-L1 to its binding partners. In certain embodiments, the PD-L1 binding partners are PD-1 and/or CD80. In another embodiment, the PD-L2 binding antagonist is a molecule that inhibits the binding of PD-L2 to its binding partners. In certain embodiments, the PD-L2 binding partner is PD-1. The antagonist may be an antibody, an antigen binding fragment thereof, an immunoadhesin, a fusion protein, or oligopeptide.

In certain embodiments, the PD-1 binding antagonist is an anti-PD-1 antibody (e.g., a human antibody, a humanized antibody, or a chimeric antibody). In certain embodiments, the anti-PD-1 antibody is a monoclonal antibody. In certain embodiments, the anti-PD-1 antibody is an antibody fragment selected from the group consisting of Fab, Fab'-SH, Fv, scFv, and $(Fab')_2$ fragments. The anti-PD-1 antibody may be a human antibody, a humanized antibody or a chimeric antibody, and may include a human constant region. In certain embodiments, the anti-PD-1 antibody is a humanized antibody. In certain embodiments, the anti-PD-L antibody is a human antibody. In certain embodiments the human constant region is selected from the group consisting of IgG1, IgG2, IgG3, and IgG4 constant regions, and in certain embodiments, the human constant region is an IgG1 or IgG4 constant region.

Examples of monoclonal antibodies that bind to human PD-1 are described in U.S. Pat. Nos. 7,488,802, 7,521,051, 8,008,449, 8,354,509, 8,168,757, and patent application publications WO 2004/004771, WO 2004/072286, WO 2004/056875, and US 2011/0271358. Specific anti-human PD-1 monoclonal antibodies include pembrolizumab (also known as MK-3475), a humanized IgG4 mAb with the structure described in WHO Drug Information, Vol. 27, No. 2, pages 161-162 (2013); nivolumab (BMS-936558), a human IgG4 mAb with the structure described in WHO Drug Information, Vol. 27, No. 1, pages 68-69 (2013); the humanized antibodies h409A11, h409A16, and h409A17, which are described in WO2008/156712, and AMP-514, which is being developed by MedImmune.

In certain embodiments, the anti-PD-1 antibody is selected from the group consisting of MDX-1106 (nivolumab), MK-3475 (lambrolizumab), and CT-011 (pidilizumab). MDX-1106, also known as MDX-1106-04, ONO-4538, BMS-936558, or nivolumab, is an anti-PD-1 antibody described in WO 2006/121168. MK-3475, also known as lambrolizumab, is an anti-PD-1 antibody described in WO 2009/114335. CT-011, also known as hBAT, hBAT-1, or pidilizumab, is an anti-PD-1 antibody described in WO 2009/101611.

In certain embodiments, the PD-1 axis binding antagonist is an anti-PD-L1 antibody. In certain embodiments, the anti-PD-L1 antibody is capable of inhibiting binding between PD-1 and PD-1 and/or between PD-L1 and CD80.

In certain embodiments, the anti-PD-1 antibody is an antibody fragment selected from the group consisting of Fab, Fab'-SH, Fv, scFv, and (Fab')$_2$ fragments. The anti-PD-L1 antibody may be a human antibody, a humanized antibody, or a chimeric antibody, and may include a human constant region. In certain embodiments, the anti-PD-L1 antibody is a humanized antibody. In certain embodiments, the anti-PD-L1 antibody is a human antibody. In certain embodiments the human constant region is selected from the group consisting of IgG1, IgG2, IgG3, and IgG4 constant regions, and in certain embodiments, the human constant region is an IgG1 or IgG4 constant region.

Examples of monoclonal antibodies that bind to human PD-1 are described in WO 2013/019906, WO 2010/077634 A1, and U.S. Pat. No. 8,383,796. Specific anti-human PD-L1 monoclonal antibodies useful as the PD-1 antagonist in the treatment method, medicaments, and uses of the present disclosure include MPDL3280A, BMS-936559, MEDI4736, MSB0010718C, and an antibody which comprises the heavy chain and light chain variable regions of SEQ ID NO:24 and SEQ ID NO:21, respectively, of WO 2013/019906. In certain embodiments, the anti-PD-L1 antibody is atezolizumab. In certain embodiments, the anti-PD-L1 antibody is avelumab. In certain embodiments, the anti-PD-L1 antibody is durvalumab. In certain embodiments, the anti-PD-L1 antibody is selected from the group consisting of YW243.55.570, MPDL3280A, MDX-1105, and MEDI4736. Antibody YW243.55.570 is an anti-PD-L1 described in WO 2010/077634. MDX-1105, also known as BMS-936559, is an anti-PD-L1 antibody described in WO 2007/005874 MEDI4736 is an anti-PD-1 monoclonal antibody described in WO 2011/066389 and US 2013/034559.

In certain embodiments, the PD-1 axis binding antagonist is an anti-PD-L2 antibody. In certain embodiments, the anti-PD-L2 antibody is capable of inhibiting binding between PD-L2 and PD-1. In certain embodiments, the anti-PD-L2 antibody is a monoclonal antibody. In certain embodiments, the anti-PD-L2 antibody is an antibody fragment selected from the group consisting of Fab, Fab'-SH, Fv, scFv, and (Fab')$_2$ fragments. The anti-PD-L2 antibody may be a human antibody, a humanized antibody, or a chimeric antibody, and may include a human constant region. In certain embodiments, the anti-PD-L2 antibody is a humanized antibody. In certain embodiments, the anti-PD-L2 antibody is a human antibody. In certain embodiments the human constant region is selected from the group consisting of IgG1, IgG2, IgG3, and IgG4 constant regions, and in certain embodiments, the human constant region is an IgG1 or IgG4 constant region.

Other useful PD-1 axis antagonists include an immunoadhesins that specifically bind to PD-1 or PD-L1 or PD-L2, and in certain embodiments specifically binds to human PD-1 or human PD-L1 or human PD-L2, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO 2010/027827 and WO 2011/066342. Specific fusion proteins useful as the PD-1 axis antagonist include AMP-224 (also known as B7-DCIg), which is a PD-L2-FC fusion protein and binds to human PD-1.

In certain embodiments, the PD-1 axis antagonist is selected from the group consisting of: CA-170, BMS-8, BMS-202, BMS-936558, CK-301, and AUNP12. In certain embodiments, the PD-1 axis antagonist is selected from the group consisting of: avelumab, nivolumab, pembrolizumab, atezolizumab, durvalumab, AMP-224 (GlaxoSmithKline), MEDI0680/AMP-514 (AstraZeneca), PDR001 (Novartis), cemiplimab, TSR-042 (Tesaro), Tizlelizumab/BGB-A317 (Beigene), CK-301 (Checkpoint Therapeutics), BMS-936559 (Bristol-Meyers Squibb), camrelizumab, sintilimab, toripalimab, genolimzumab, and A167 (Sichuan Kelun-Biotech Biopharmaceutical). In certain embodiments, the PD-1 axis antagonist is selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), (LLY) AM0001 (Armo Biosciences), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), and RXI-762 (RXi). In certain embodiments, the PD-1 axis antagonist is selected from the group consisting of: PRS-332 (Pieris Pharmaceuticals), ALPN-202 (Alpine Immune Science), TSR-075 (Tesaro/Anaptys Bio), MCLA-145 (Merus), MGD013 (Macrogenics), and MGD019 (Macrogenics). In certain embodiments, the PD-1 axis antagonist is selected from an anti-PD1 mono-specific or bi-specific antibody described in, for example, WO 2016/077397, WO 2018/156777, and International Application No. PCT/US2013/034213, filed May 23, 2018.

In certain embodiments, the PD-1 axis antagonist is selected from the group consisting of pembrolizumab (MK-3475 or lambrolizumab, Keytruda; Merck); nivolumab (Opdivo; Bristol-Myers Squibb); and cemiplimab (Libtayo; Regeneron). In certain embodiments, the PD-1 axis antagonist is selected from the group consisting of JTX-4014 (Jounce Therapeutics); spartalizumab (PDR001; Novartis); Camrelizumab (SHR1210; Jiangsu HengRui Medicine Co., Ltd); sintilimab (IBI308; Innovent and Eli Lilly); tislelizumab (BGB-A317; Novartis); toripalimab (JS 001; Coherus); Dostarlimab (TSR-042, WBP-285; GlaxoSmithKline); INCMGA00012 (MGA012; Incyte and MacroGenics); AMP-224 (AstraZeneca/MedImmune and GlaxoSmithKline); and AMP-514 (MEDI0680; AstraZeneca). In certain embodiments, the PD-1 axis antagonist is pembrolizumab. In certain embodiments, the PD-1 axis antagonist is nivolumab. In certain embodiments, the PD-1 axis antagonist is cemiplimab In certain embodiments, the PD-1 axis antagonist is selected from the group consisting of atezolizumab (Tecentriq; Roche Genentech); avelumab (Bavencio; Merck Serono and Pfizer); and durvalumab (Imfinzi; AstraZeneca). In certain embodiments, the PD-1 axis antagonist is selected from the group consisting of envafolimab (KNO35; TRACON); CK-301 (Checkpoint Therapeutics); AUNP12 (Aurigene and Laboratoires Pierre Fabre); CA-170 (Aurigene and Curis); and BMS-986189 (Bristol-Myers Squibb). In certain embodiments, the PD-1 axis antagonist is atezolizumab. In certain embodiments, the PD-1 axis antagonist is avelumab. In certain embodiments, the PD-1 axis antagonist is durvalumab.

5. Pharmaceutical Compositions and Methods of Administration

The Cbl-b inhibitor compounds and second agents provided herein can be formulated into pharmaceutical compositions using methods available in the art and those disclosed herein. In particular embodiments, the Cbl-b inhibitor compound is formulated in a pharmaceutical composition comprising the compound and one or more pharmaceutically acceptable carriers, diluents, or excipients. In certain embodiments, the PD-1 axis antagonist is formulated according to the formulations known in the art for the inhibitor. In particular embodiments, the Cbl-b inhibitor compound is formulated in a pharmaceutical composition suitable for oral administration. In particular embodiments, the PD-1 axis antagonist is formulated in a pharmaceutical composition suitable for parenteral administration. While the Cbl-b inhibitor compound and PD-1 axis antagonist are not expected to be formulated in the same composition, this embodiment is not excluded from the description herein.

The methods provided herein encompass administering pharmaceutical compositions comprising a Cbl-b compound or a PD-1 axis antagonist and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions provided herein may be administered by any route known in the art. Exemplary routes of administration include, but are not limited to, oral, intravenous, inhalation, intraarterial, intradermal, intramuscular, intraperitoneal, intravenous, nasal, parenteral, pulmonary, and subcutaneous routes. In certain embodiments, a pharmaceutical composition provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing, and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided herein are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In certain embodiments, the pharmaceutical composition comprises an anti-foaming agent. Any suitable anti-foaming agent may be used. In certain embodiments, the anti-foaming agent is selected from an alcohol, an ether, an oil, a wax, a silicone, a surfactant, and combinations thereof. In certain embodiments, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethyl-hexanol, dimethicone, oleyl alcohol, simethicone, and combinations thereof.

In certain embodiments, the pharmaceutical composition comprises a co-solvent. Illustrative examples of co-solvents include ethanol, poly(ethylene) glycol, butylene glycol, dimethylacetamide, glycerin, and propylene glycol.

In certain embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In certain embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In certain embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In certain embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated herein by reference in its entirety.

In certain embodiments, the pharmaceutical composition comprises a solvent. In certain embodiments, the solvent is saline solution, such as a sterile isotonic saline solution or dextrose solution. In certain embodiments, the solvent is water for injection.

In certain embodiments, the pharmaceutical compositions are in a particulate form, such as a microparticle or a nanoparticle. Microparticles and nanoparticles may be formed from any suitable material, such as a polymer or a lipid. In certain embodiments, the microparticles or nanoparticles are micelles, liposomes, or polymersomes.

Further provided herein are anhydrous pharmaceutical compositions and dosage forms comprising therapeutic agent, since, in certain embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

In human therapeutics, the doctor will determine the posology which he considers most appropriate according to a preventive or curative treatment and according to the age, weight, condition, and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amounts of the Cbl-b compound or composition and PD-1 axis antagonist or composition which will be effective in the prevention or treatment of a disorder or one or more symptoms thereof will vary with the nature and severity of the disease or condition, and the route by which the agents are administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram).

In certain embodiments, the dosage of the Cbl-b compound provided herein, based on weight of the compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the Cbl-b compound is 0.1 mg to 1000 mg, 0.1 mg to 900 mg, 0.1 mg to 800 mg, 0.1 mg to 750 mg, 0.1 mg to 700 mg, 0.1 mg to 600 mg, 0.1 mg to 500 mg, 0.1 mg to 400 mg, 0.1 mg to 300 mg, 0.1 mg to 250 mg, 0.1 mg to 200 mg, 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 mg to 2.5 mg, 0.25 mg to 20 mg, 0.25 mg to 15 mg, 0.25 mg to 12 mg, 0.25 mg to 10 mg, 0.25 mg to 7.5 mg, 0.25 mg to 5 mg, 0.25 mg to 2.5 mg, 0.5 mg to 20 mg, 0.5 to 15 mg, 0.5 mg to 12 mg, 0.5 mg to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, the dosage of the PD-1 axis antagonist is according to the product label or other instruction. In certain embodiments, the dosage of the PD-1 axis antagonist, based on weight of the antagonist, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the PD-1 axis antagonist is 0.1 mg to 1000 mg, 0.1 mg to 900 mg, 0.1 mg to 800 mg, 0.1 mg to 750 mg, 0.1 mg to 700 mg, 0.1 mg to 600 mg, 0.1 mg to 500 mg, 0.1 mg to 400 mg, 0.1 mg to 300 mg, 0.1 mg to 250 mg, 0.1 mg to 200 mg, 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 mg to 2.5 mg, 0.25 mg to 20 mg, 0.25 mg to 15 mg, 0.25 mg to 12 mg, 0.25 mg to 10 mg, 0.25 mg to 7.5 mg, 0.25 mg to 5 mg, 0.25 mg to 2.5 mg, 0.5 mg to 20 mg, 0.5 mg to 15 mg, 0.5 mg to 12 mg, 0.5 mg to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose of either agent can be administered according to a suitable schedule, for example, once, two times, three times, or four times weekly. It may be necessary to use dosages of the agents outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat, or ameliorate such disorders, but insufficient to cause, or sufficient to reduce, adverse effects associated with the agents provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an agent provided herein followed by one or more maintenance doses.

In certain embodiments, a dose of an agent provided herein can be administered to achieve a steady-state concentration of the antibody in blood or serum of the subject. The steady-state concentration can be determined by measurement according to techniques available to those of skill or can be based on the physical characteristics of the subject such as height, weight, and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

6. Therapeutic Applications

The combinations provided herein may be useful for the treatment of any disease or condition involving abnormal cell growth or proliferation. In certain embodiments, the disease or condition is a disease or condition that can benefit from treatment with a Cbl-b inhibitor compound or a PD-1 axis antagonist, or both. In certain embodiments, the disease or condition is a cancer. In certain embodiments, the disease or condition is a solid tumor. In certain embodiments, the disease or condition is a hematological cancer.

Any suitable cancer may be treated with combinations provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer (including triple-negative breast cancer, or TNBC), bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fallopian tube carcinoma, fibrous histiocytoma, Ewing sarcoma, eye cancer, germ cell tumor, gallbladder cancer, gastric cancer, gastric/gastroesophageal junction (GEJ) cancer, gastrointestinal carcinoid tumor, gastrointestinal stromal tumor, gestational trophoblastic disease, glioma, head and neck cancer, hepatocellular cancer, histiocytosis, Hodgkin lymphoma, diffuse large B cell lymphoma (DLBCL) including Richter transformation (RT), hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, metastatic melanoma, Merkel cell carcinoma, mesothelioma, malignant pleural mesothelioma (MPM), metastatic squamous neck cancer with occult primary, squamous cell carcinoma of the head and neck (HNSCC), midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer (NSCLC), oropharyngeal cancer, osteosarcoma, ovarian cancer, platinum-resistant epithelial ovarian cancer (EOC), pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, primary peritoneal carcinoma, prostate cancer, metastatic castration-resistant prostate cancer (mCRPC), rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, urothelial cancer, muscle-invasive urothelial cancer, and Wilms tumor.

In certain embodiments, the disease to be treated with the combinations provided herein is gastric cancer, colorectal cancer, renal cell carcinoma, cervical cancer, non-small cell lung carcinoma, ovarian cancer, uterine cancer, fallopian tube carcinoma, primary peritoneal carcinoma, uterine corpus carcinoma, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In certain embodiments, the disease is ovarian cancer. In certain embodiments, the disease is breast cancer. In certain embodiments, the disease is triple-negative breast cancer (TNBC). In certain embodiments, the disease is lung cancer. In certain embodiments, the disease is non-small cell lung cancer (NSCLC). In certain embodiments, the disease is head and neck cancer. In certain embodiments, the disease is renal cell carcinoma. In certain embodiments, the disease is brain carcinoma. In certain embodiments, the disease is endometrial cancer.

7. Kits

In certain embodiments, a compound or combination provided herein is provided in the form of a kit, i.e., a packaged combination of reagents in predetermined amounts with instructions for performing a procedure. In other embodiments, the procedure is a therapeutic procedure. In certain embodiments, the kit comprises a Cbl-b inhibitor compound, or a composition thereof, and instructions for use in combination with a PD-1 axis antagonist. In certain embodiments, the kit comprises a PD-1 axis antagonist, or a composition thereof, and instructions for use in combination with a Cbl-b inhibitor compound. In certain embodiments, the kit comprises a Cbl-b inhibitor compound, or a composition thereof, and a PD-1 axis antagonist, or composition thereof.

EXAMPLES

Example 1

This example provides assays and results for treating tumor models in vivo with single agent Cbl-b compounds described herein.

As shown in FIG. 1, the effects of compound 23 on total primary human T-cells were assessed. Cells were stimulated with plate bound anti-CD3 (right) or anti-CD3/anti-CD28 (left) in the presence or absence of the indicated concentration of compound 23. Release of IL-2 or IFN-γ were assessed by ELISA. Compound 23 inhibition of Cbl-b enhanced IL-2 and IFN-γ secretion in primary human T-cells stimulated with anti-CD3 antibodies, in both the presence and absence of CD28 co-stimulation, although to a lesser degree in the absence of co-stimulation.

Figure 2:
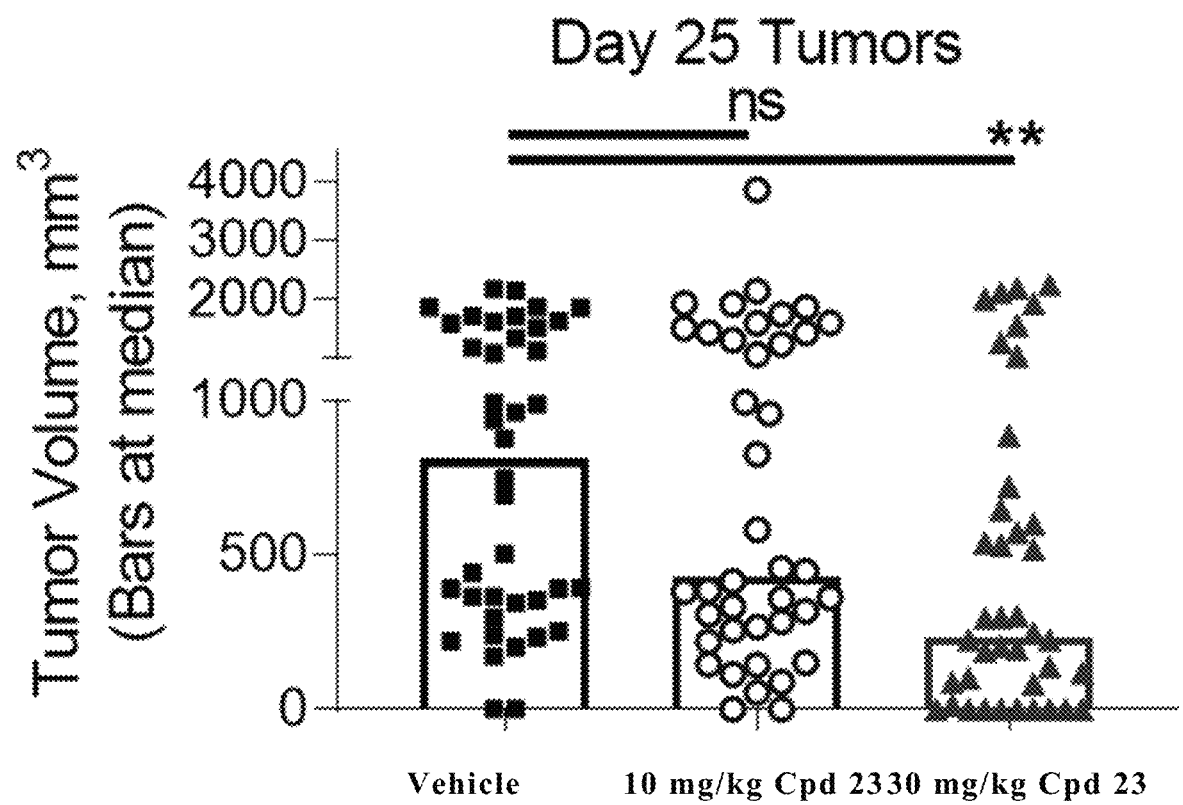
FIG. 2 provides tumor volume in mice bearing tumors 25 days following administration of vehicle or compound 23.

As shown in FIG. 2, the effects of compound 23 on CT26 tumor volume in mouse models were assessed. Mice bearing tumors on their left and right flanks were treated from Day 7 to Day 32 with oral compound 23 at 10 mg/kg (blue circles) or 30 mg/kg (red circles) or vehicle (black squares). Volumes at Day 25 are indicated. Statistics were calculated with one-way ANOVA and Dunn's multiple comparisons test **$P≤0.01$.

Another in vivo study evaluated the ability of compound 23 treatment, started before the primary tumor resection, to eradicate 4T1 breast carcinoma metastatic disease. The 4T1 triple negative mammary carcinoma is a transplantable tumor cell line that is highly tumorigenic and invasive and, unlike most tumor models, spontaneously metastasizes from a primary tumor growing in the mammary gland to multiple distant sites including lymph nodes, blood, liver, lung, brain, and bone. Tumor cells are easily transplanted into the mammary glands so that the primary tumor grows in the anatomically relevant site. The progressive spread of 4T1 metastases to other organs is very similar to that of human mammary cancer. Animals die from disseminated metastatic disease regardless of resection of the primary tumor (Pulaski et al., 2000, Current Protocols in Immunology 39(1):20.2.1-20.2.16). As shown in FIG. 3, mice bearing 4T1 tumors in the 4th mammary fat pad on the ventral flank were treated from Day 8 to Day 46 by daily oral administration of either: vehicle (0.5% methylcellulose, 0.2% Polysorbate 80 in deionized water+1 eq HCl) or compound 23 at 30 mg/kg daily. Beginning on Day 7, tumor volumes were measured twice weekly until they reached a mean tumor volume of 145 mm$^3$ when the primary tumors were resected on Day 14 and 15 (dotted line). Median survival time were calculated for each group and body weights were monitored until the end of the study on Day 140. Body weights were measured twice weekly then once weekly starting Day 47. FIG. 3 shows percentage survival over time through Day 140. Statistical significance of differences in conditional survival between groups was evaluated using the Log-rank (Mantel-Cox) test. Significance was reported as not significant (ns) $P>0.05$, *$P≤0.05$, $P≤0.01$, *$P≤0.001$, and ****$P≤0.0001$. Treatment with compound 23 dosed orally at 30 mg/kg significantly increased median survival time compared to vehicle control. Median survival is reported as undefined for the compound 23 group, as survival exceeds 50% at Day 140. Importantly, 54% of the mice treated with compound 23 remained tumor free until the end of the study, suggesting that compound 23 can significantly extend survival in a model of metastatic disease.

A shown in these experiments, in vivo oral administration of compound 23 in mice demonstrated significant anti-tumor activity in a colon carcinoma tumor models, CT26, as well as a metastatic triple negative breast tumor model, 4T1.

Example 2

In this example, the gene expression changes induced in tumors from mice treated with compound 23 studies were investigated. To perform this assessment, the nCounter Pan-Cancer Immune Profiling Panel was used, which is a multiplexed gene expression panel developed by NanoString Technologies that measures expression of 770 immune and cancer related genes (Eastel et al., 2019, Expert Review of Molecular Diagnostics, 19(7):591-598). This technology is a unique gene expression tool that covers many important features of the immune response in the tumor microenvironment and was used to facilitate the understanding of immune related changes in tumors treated with compound 23.

Figure 4A:
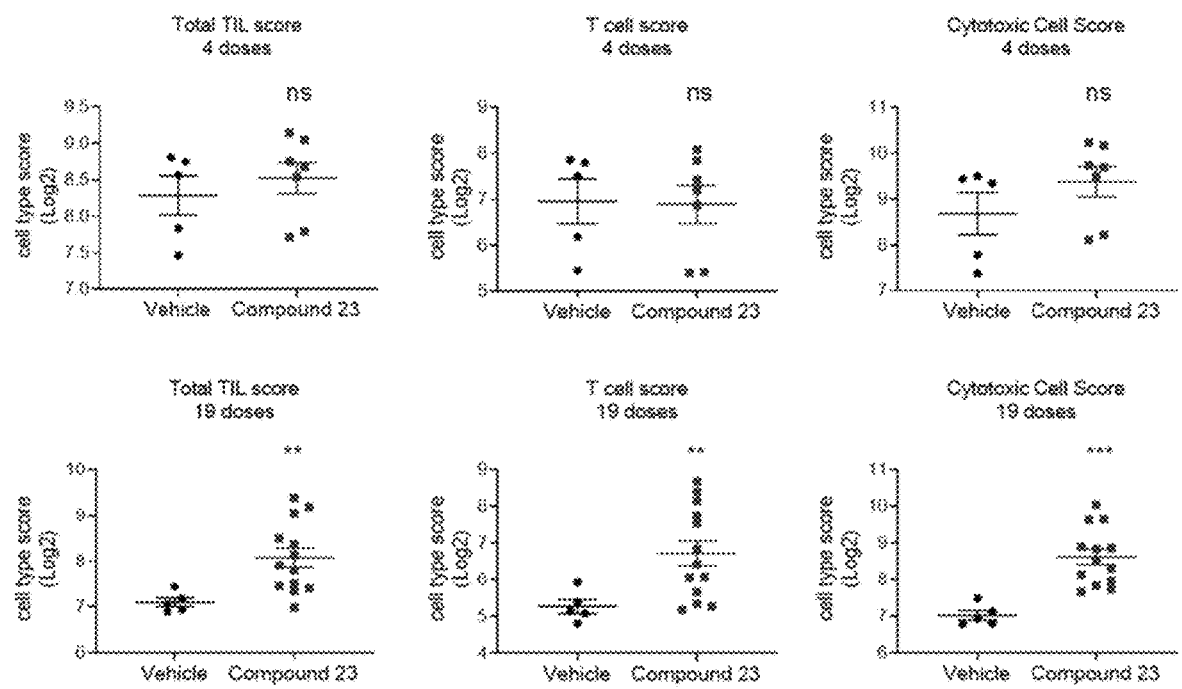
FIG. 4A provides the effects of orally administered compound 23 on tumor inflitrating lymphocytes (TIL) after 4 or 19 daily doses.

In FIG. 4A, CT26 tumors were harvested after 4 doses and after 19 doses of compound 23 or vehicle and gene expression was directly measured using the nCounter Mouse PanCancer Immune Profiling Panel. Analysis was performed using the nSolver 4.0 and the nCounter Advanced Analysis software comparing gene expression in compound 23 to vehicle treated tumors. FIG. 4A (top row) shows individual TIL, T-cell, and cytotoxic cell scores between vehicle and compound 23 treated groups after 4 doses. FIG. 4A (bottom row) shows individual TIL, T-cell, and cytotoxic cell scores between vehicle and compound 23 treated groups after 19 doses. Statistical significance of differences in mean cell type scores between compound 23 and vehicle treated groups was evaluated using Mann-Whitney test (*$P≤0.05$, $P≤0.01$, and *$P≤0.001$).

Figure 4B:
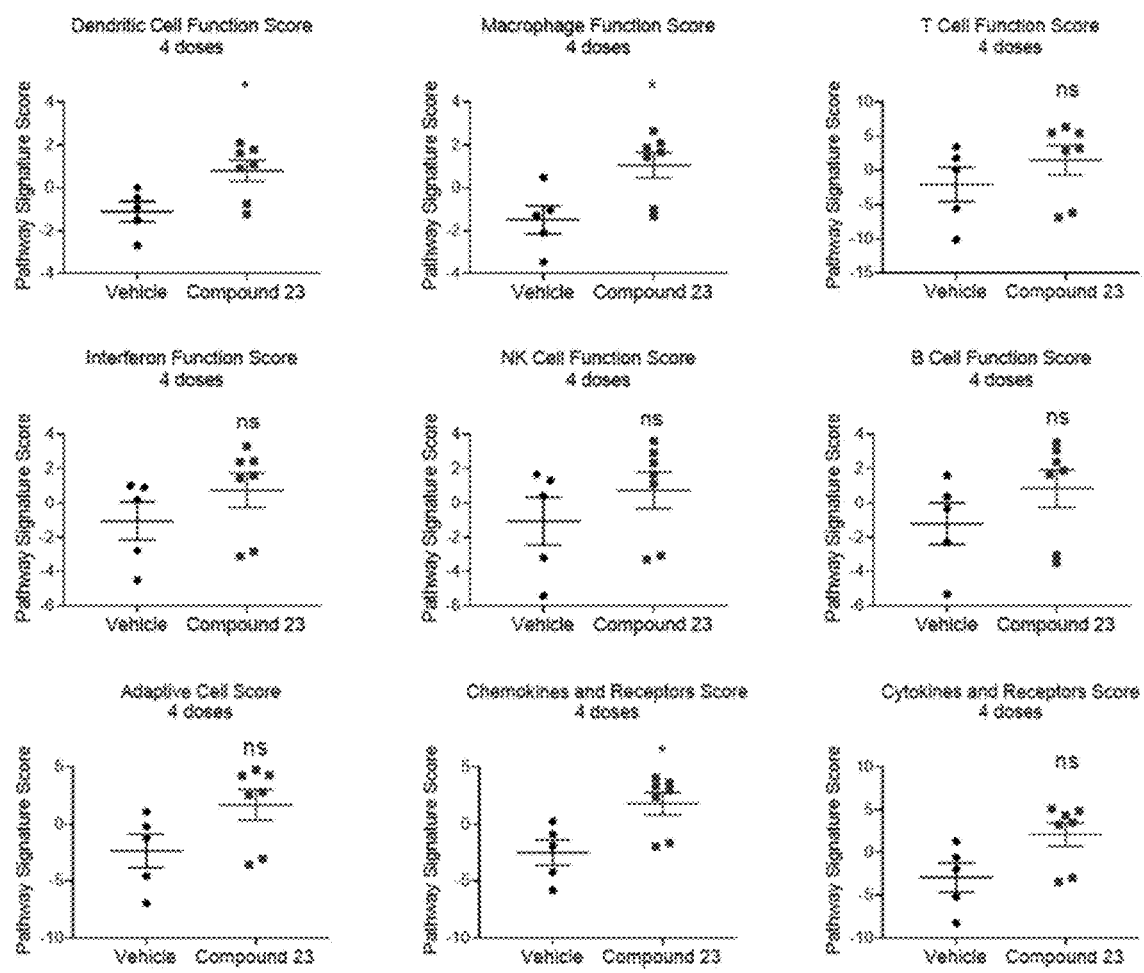
FIG. 4B provides the effects of orally administered compound 23 on gene expression immune related pathway scores in CT26 tumor tissue after 4 doses.

In FIG. 4B, CT26 tumors were harvested after 4 treatment doses and gene expression was directly measured using the nCounter Mouse PanCancer Immune Profiling Panel. Analysis was performed using the nSolver 4.0 and the nCounter Advanced Analysis software comparing gene expression in compound 23 to vehicle treated tumors. As indicated in the titles above each panel, scatter plots of individual Pathway Signature Scores of vehicle and compound 23 treated tumors are shown. Statistical significance of differences in Pathway Signature Scores between compound 23 and vehicle treated groups was evaluated using Mann-Whitney test (*$P≤0.05$, $P≤0.01$, and *$P≤0.001$).

Figure 4C:
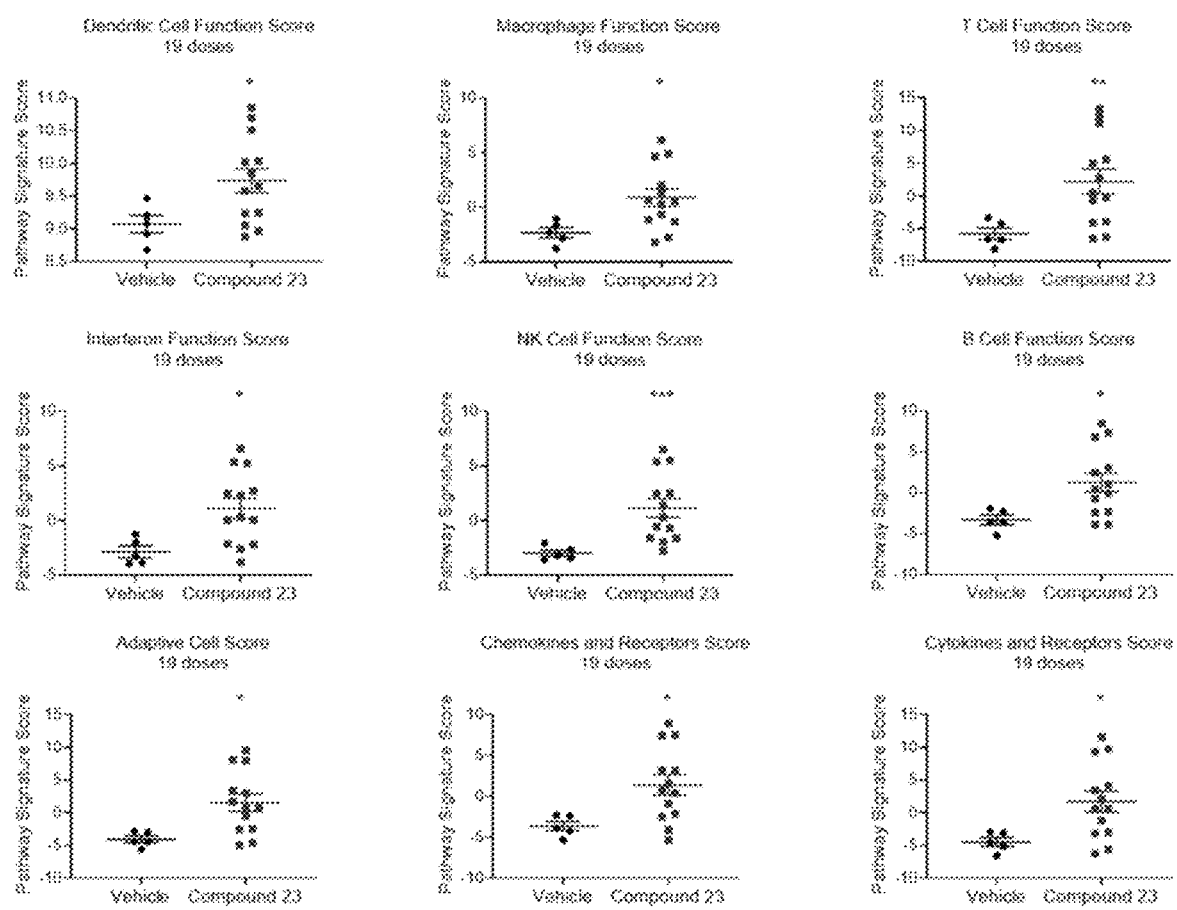
FIG. 4C provides the effects of orally administered compound 23 on gene expression immune related pathway scores in CT26 tumor tissue after 19 doses.

In FIG. 4C, CT26 tumors were harvested after 19 treatment doses and gene expression was directly measured using the nCounter Mouse PanCancer Immune Profiling Panel. Analysis was performed using the nSolver 4.0 and the nCounter Advanced Analysis software comparing gene expression in compound 23 to vehicle treated tumors. As indicated in the titles above each panel, scatter plots of individual Pathway Signature Scores of vehicle and compound 23 treated tumors are shown. Statistical significance of differences in Pathway Signature Scores between compound 23 and vehicle treated groups was evaluated using Mann-Whitney test (*$P≤0.05$, $P≤0.01$, and *$P≤0.001$).

The immune context of tumors from compound 23 treated mice were significantly changed compared to tumors from vehicle treated mice. After 4 doses, single agent oral compound 23 administered daily at 30 mg/kg resulted in a clear trend of increased infiltration of tumor infiltrating lymphocytes (TIL) (P=0.6679), T-cell (P=0.7551), and cytotoxic cells (P=0.1061) (FIG. 4A). At the later time point, following 19 doses of oral compound 23, there were significant increases in TIL (P=0.0044), T-cell (P=0.0098), and cytotoxic cell (P=0.0002) infiltration in CT26 tumors relative to vehicle treated animals (FIG. 4B).

After 4 doses of compound 23, tumors exhibited significant gene expression changes in pathways associated with innate immune signaling, including dendritic cell function and macrophage function and chemokine receptors and pathways (FIG. 4C). Although there was a trend for increases in T-cell, B cell, NK cell, and adaptive immune function, these changes were not significant. However, after 19 doses, compound 23 treated CT26 tumors exhibited significantly enhanced function of immune related pathway scores, including ones related to dendritic cell function, macrophage function, T-cell function, NK cell function, B cell function as well as interferon function, adaptive immunity, chemokine and receptor response, and cytokine and receptor signature response (FIG. 4C). Collectively, these data demonstrate that compound 23 induced anti-tumor activity in the CT26 syngeneic tumor model, enhancing both intratumoral density and function of immune cells.

Figure 5:
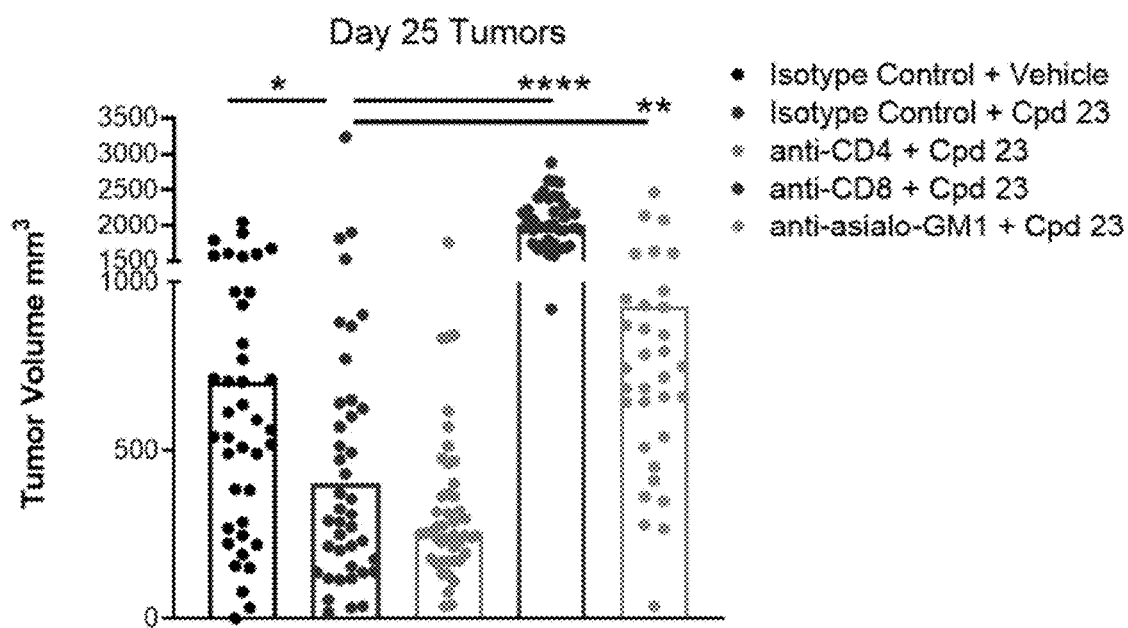
FIG. 5 provides antitumor efficacty in mice bearing CT26 tumors following oral administration of compound 23 at 30 mg/kg in the presence of depleting antibodies for CD4+ cells, CD8+ cells, or NK cells (anti-asialo-GM1).

As shown in FIG. 5, mice bearing CT26 tumors on their left and right flanks were treated from Day 9 to Day 25 with oral compound 23 at 30 mg/kg, PO QD, in the presence of depleting antibodies for CD4+ cells, CD8+ cells, or NK cells (anti-asialo-GM1). Tumor volume at Day 25 is indicated. CD8+ T-cell or NK cell depletion abrogates compound 23 activity. Stats were calculated with Mann-Whitney (Vehicle vs. compound 23) or one-way ANOVA with Dunn's multiple comparisons test (compound 23 vs. Depletion groups); (*P≤0.05, P≤0.01, **P≤0.0001). The efficacy of compound 23 on tumors is CD8+ T function and on NK cell function.

Example 3

This example provides assays and results for treating tumor models in vivo with combinations of Cbl-b compounds and anti-PD1 antibodies as described herein. The antibody is a mouse anti-PD1 RMP1-14 antibody, useful in mouse in vivo assays as model for administration of human PD-1 axis antagonists for treatment of human cancer.

Figure 6:
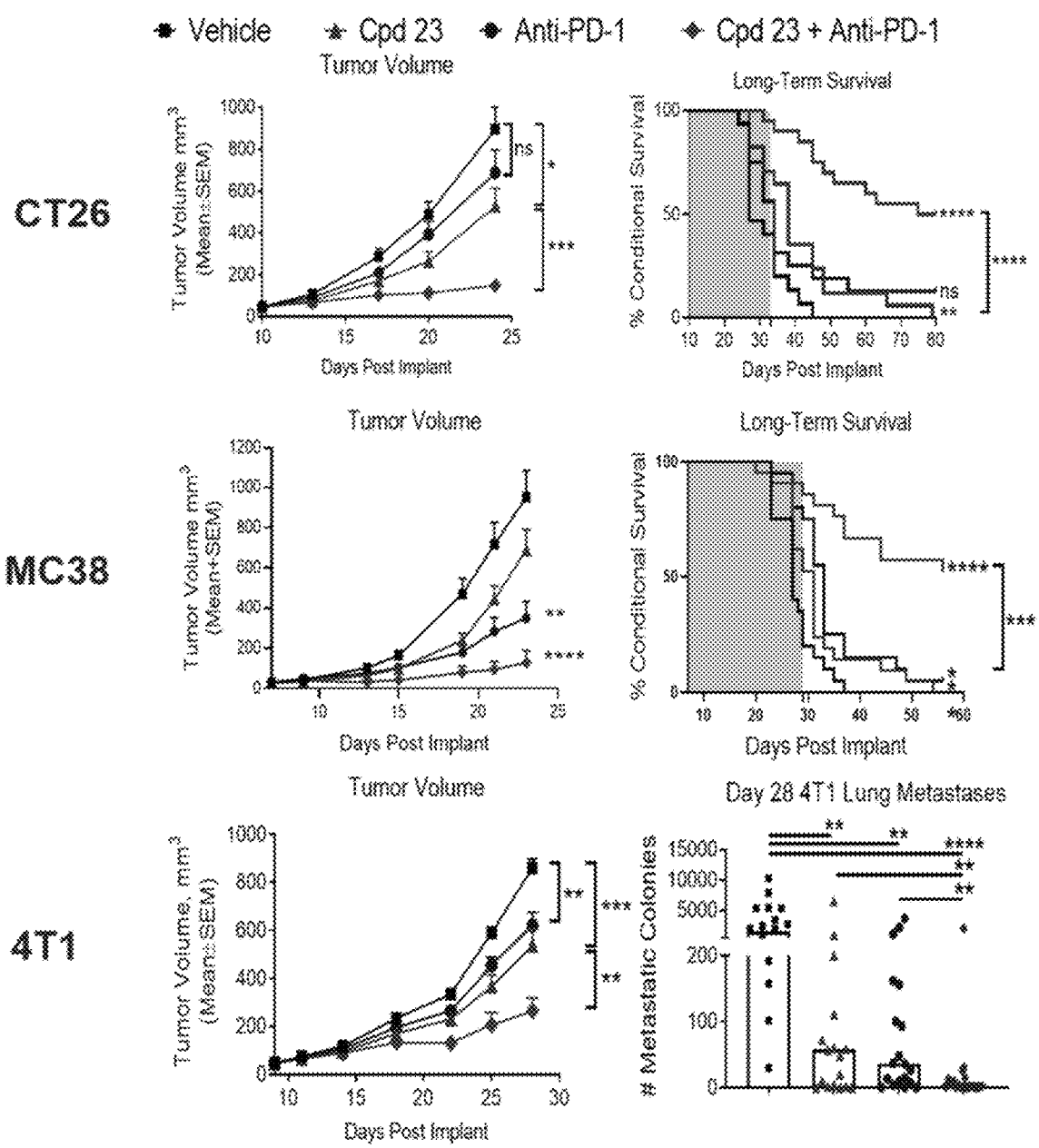
FIG. 6 provides synergy of compound 23 and anti-PD1 antibody in mice with CT26, MC38, or 4T1 tumors.

FIG. 6 provides results in three tumor models. With the CT26 Model, mice bearing CT26 tumors on their left and right flanks were treated from Day 10 to Day 33 by administration of either: vehicle (0.5% methylcellulose, 0.2% Polysorbate 80 in deionized water+1 eq HCl) daily, orally (PO) compound 23 at 30 mg/kg daily, PO; anti-PD-1 antibody at 10 mg/kg twice weekly by intraperitoneal (IP) injection; or the combination of compound 23 at 30 mg/kg daily, PO and anti-PD-1 antibody at 10 mg/kg twice weekly by IP injection. Beginning on Day 10, tumor volumes were measured twice weekly. In FIG. 6 (CT26), the left graph shows group mean tumor volumes±SEM, on Days 10 through 24. Statistical significance of differences in mean tumor volumes between groups was evaluated from Day 10 to Day 24 using repeated measure two-way ANOVA with Dunnett's multiple comparisons test (not significant (ns) P>0.05, *P≤0.05, P≤0.01, *P<0.001, and **** P≤0.0001). In FIG. 6 (CT26), the right graph shows the percentage animals surviving between Days 10 to 80 as defined by reaching the conditional survival endpoint of bearing a tumor with volume equal to or greater than 2000 mm$^3$, unless having previously met a humane endpoint.

In the results reported in FIG. 6 (at CT26), single agent compound 23 dosed orally at 30 mg/kg showed anti-tumor activity in the CT26 syngeneic tumor model, with a significantly reduced tumor volume, a TGI of 62% compared to vehicle controls, and a median survival time of 38 days compared to 27 days for controls. Anti-PD-1 dosed at 10 mg/kg had weaker effects than compound 23, with a TGI of 47% and a median survival of 34 days. However, the combination of compound 23 dosed together with anti-PD-1 resulted the strongest anti-tumor activity, with a TGI of 88% and a median survival of 77.5 days; 50% of combination-treated mice were tumor free at the end of the study. Therefore, compound 23 treatment significantly reduces tumor growth and synergizes with PD-1 antibody blockade, leading to rejection of established tumors.

In the MC38 Model, mice bearing MC38 tumors on their left and right flanks were treated from Day 10 to Day 29 by administration of either: vehicle (0.5% methylcellulose, 0.2% Polysorbate 80 in deionized water+1 eq HCl) daily, orally (PO) compound 23 at 30 mg/kg daily, PO; anti-PD-1 antibody at 10 mg/kg twice weekly by intraperitoneal (IP) injection; or the combination of compound 23 at 30 mg/kg daily, PO and anti-PD-1 antibody at 10 mg/kg twice weekly by IP injection. Beginning on Day 10, tumor volumes were measured twice weekly. In FIG. 6 (MC38), the left graph shows group mean tumor volumes±SEM, on Days 10 through 24. Statistical significance of differences in mean tumor volumes between groups was evaluated from Day 7 to Day 23 using repeated measure two-way ANOVA with Dunnett's multiple comparisons test (not significant (ns) P>0.05, *P≤0.05, P≤0.01, *P≤0.001, and **** P≤0.0001). In FIG. 6 (MC38), the right graph shows the percentage animals of surviving between Days 7 to 56 as defined by reaching the conditional survival endpoint of bearing a tumor with volume equal to or greater than 2000 mm3, unless having previously met a humane endpoint.

In the results reported at FIG. 6 (at MC38), single agent compound 23 showed anti-tumor activity that resulted in significantly smaller primary tumors compared to the vehicle control group. Single agent anti-PD-1 also significantly reduced the size of primary tumors compared to the vehicle control group. The combination of compound 23 plus anti-PD-1 therapy resulted in robust anti-tumor activity, with significant reduction in primary tumor volume compared to either vehicle controls or treatment with single agent compound 23 or single agent anti-PD-1. The combination therapy showed significant improvement in primary tumor volume compared to vehicle controls or treatment with single agent compound 23 or single agent anti-PD-1 (FIG. 6, MC38). Therefore, compound 23 treatment significantly reduces tumor growth and synergizes with PD-1 antibody blockade, leading to rejection of established tumors and reduction of tumor burden.

In the 4T1 Model, mice bearing orthotopic 4T1 tumors in their 4th mammary fat pad on the left ventral flank were treated from Day 9 to Day 28 by administration of either: vehicle control (0.5% methylcellulose, 0.2% Polysorbate 80 in deionized water+1 eq HCl) given daily PO; compound 23 at 30 mg/kg given daily PO; anti-PD-1 blocking antibody at 10 mg/kg twice weekly given by IP injection; or the combination of compound 23 at 30 mg/kg daily, PO and anti-PD-1 antibody at 10 mg/kg twice weekly by IP injection. Beginning on Day 9, tumor volumes and body weights were measured twice weekly. In FIG. 6 (4T1), the left graph shows group mean tumor volumes±SEM, on Days 9 through 28. Statistical significance of differences in mean tumor volumes between groups was evaluated from Day 9 to Day 28 using a mixed-effects model and Dunnett's multiple comparisons test (brackets or lines between groups summarize statistical significance: not significant (ns) P>0.05, *P≤0.05, P≤0.01, *P≤0.001, and ****P≤0.0001). In FIG. 6 (4T1), the right graph shows the number of 4T1 metastatic tumor cell colonies measured in lungs from the four treatment groups harvested on Day 28 with bars at group median values. Statistical significance of differences in the number of colonies between groups was evaluated using Kruskal-Wallis one-way ANOVA with Dunn's multiple comparisons test.

In the experiment presented in FIG. 6 (at 4T1), single agent compound 23 showed anti-tumor activity that resulted in significantly smaller primary tumors and reduced metastatic lung tumor burden compared to the vehicle control group. Single agent anti-PD-1 also significantly reduced the size of primary tumors and resulted in lower metastatic lung tumor burden compared to the vehicle control group. The combination of compound 23 plus anti-PD-1 therapy resulted in robust anti-tumor activity, with significant reduction in primary tumor volume and metastatic lung tumor burden compared to either vehicle controls or treatment with single agent compound 23 or single agent anti-PD-1. Furthermore, the combination therapy resulted in complete regression of the primary tumor in 16% of mice, and 47% of mice had no metastatic colonies detected in their lungs. The combination therapy showed significant improvement in primary tumor volume and metastatic lung tumor burden compared to vehicle controls or treatment with single agent compound 23 or single agent anti-PD-1 (FIG. 6 at 4T1). Therefore, compound 23 treatment significantly reduces tumor growth and synergizes with PD-1 antibody blockade, leading to rejection of established tumors and reduction of metastatic tumor burden.

Example 4

This example provides assays and results for the effects of Cbl-b compound treatment on immune cell phenotypes in mouse tumor models and correlation of treatment efficacy with immune cell levels.

Figure 7:
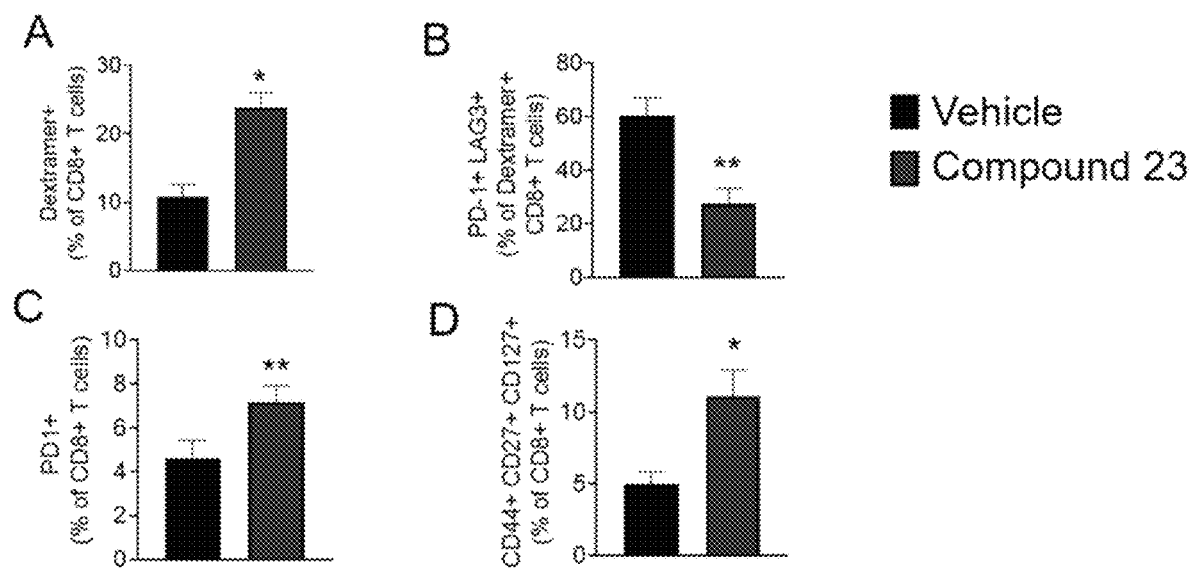
FIG. 7, panels 7A-7D, provide the effect of compound 23 treatment on CD8+ T-cell immune phenotype, both in tumor and blood samples from treated 4T1-tumor-bearing mice.

In FIG. 7, mice bearing orthotopic 4T1 tumors in their 4th mammary fat pad on the left ventral flank were treated from Day 9 to Day 28 by administration of either: vehicle control (0.5% methylcellulose, 0.2% Polysorbate 80 in deionized water+1 eq HCl) given daily PO; compound 23 at 30 mg/kg given daily PO; and tumor and blood samples were harvested on Day 28 and analyzed by Flow Cytometry.

FIG. 7A shows that compound 23 increased the frequency of tumor gp70 antigen-specific CD8+ T-cells (AH1 Dextramer+CD8+ T-cells) in 4T1 tumors from treated mice. FIG. 7B shows that compound 23 decreased the frequency of tumor gp70 antigen-specific CD8+ T-cells (AH1 Dextramer+CD8+ T-cells) with exhaustion phenotype (PD-1+ LAG3+) in in 4T1 tumors from treated mice. FIG. 7C shows that compound 23 increased the frequency of circulating CD8+ T-cells with activated phenotype (PD-1+) in the blood of treated 4T1-tumor-bearing mice. FIG. 7D shows that compound 23 increased the frequency of circulating CD8+ T-cells with memory phenotype (CD44+CD27+CD127+) in the blood of treated 4T1-tumor-bearing mice.

Figure 8:
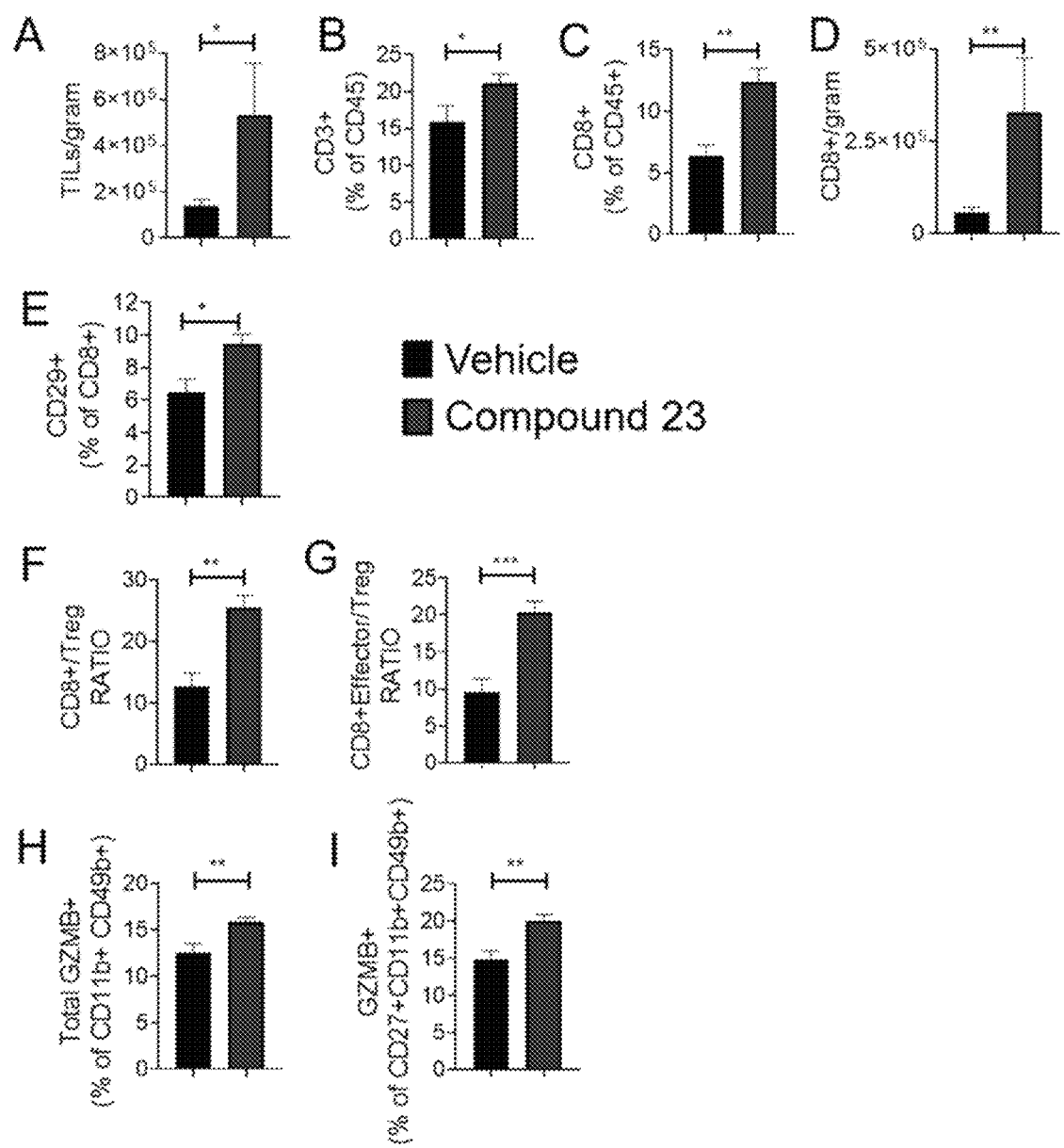
FIG. 8, panels 8A-8I, provide the effect of compound 23 treatment on the density and phenotype of tumor-infiltrating leukocytes from treated CT2 v6-tumor-bearing mice.

In FIG. 8, mice bearing CT26 tumors on their left and right flanks were treated from Day 10 to Day 28 by administration of either vehicle (0.5% methylcellulose, 0.2% Polysorbate 80 in deionized water+1 eq HCl) daily or orally (PO) compound 23 at 30 mg/kg daily. CT26 tumors were harvested after 19 doses of compound 23 or vehicle and tumor-infiltrating immune cell density and phenotype was assessed by flow cytometry.

FIG. 8A shows that compound 23 increased the number of tumor-infiltrating leukocytes (TIL) per gram of tumor in CT26 tumors from treated mice. FIG. 8B shows that compound 23 increased the frequency of total CD3+ T-cells as a percentage of CD45+ leukocytes in CT26 tumors from treated mice. FIGS. 8C and 8D shows that compound 23 increased the frequency of total CD8+ T-cells as a percentage of CD45+ leukocytes and the number of total CD8+ T-cells per gram of tumor in CT26 tumors from treated mice. FIG. 8E shows that compound 23 increased the frequency of CD8+ T-cells that express the activation marker CD29 (CD29+) in CT26 tumors from treated mice. FIGS. 8F and 8G shows that compound 23 increased the CD8+ T-cells to Tregs ratio and CD8+ effector T-cells (identified as PD1+) to Tregs ratio in CT26 tumors from treated mice. FIGS. 8H and 8I shows that compound 23 increased frequency of Tumor-infiltrating NK cells with cytotoxic phenotype in CT26 tumors from treated mice. FIG. 8H shows the frequency of activated NK cells (CD11b+) that express Granzyme+, and FIG. 8I shows the frequency of activated NK cells (CD27+ CD11b+) that express Granzyme+ in CT26 tumors from compound 23-treated mice.

Figure 9:
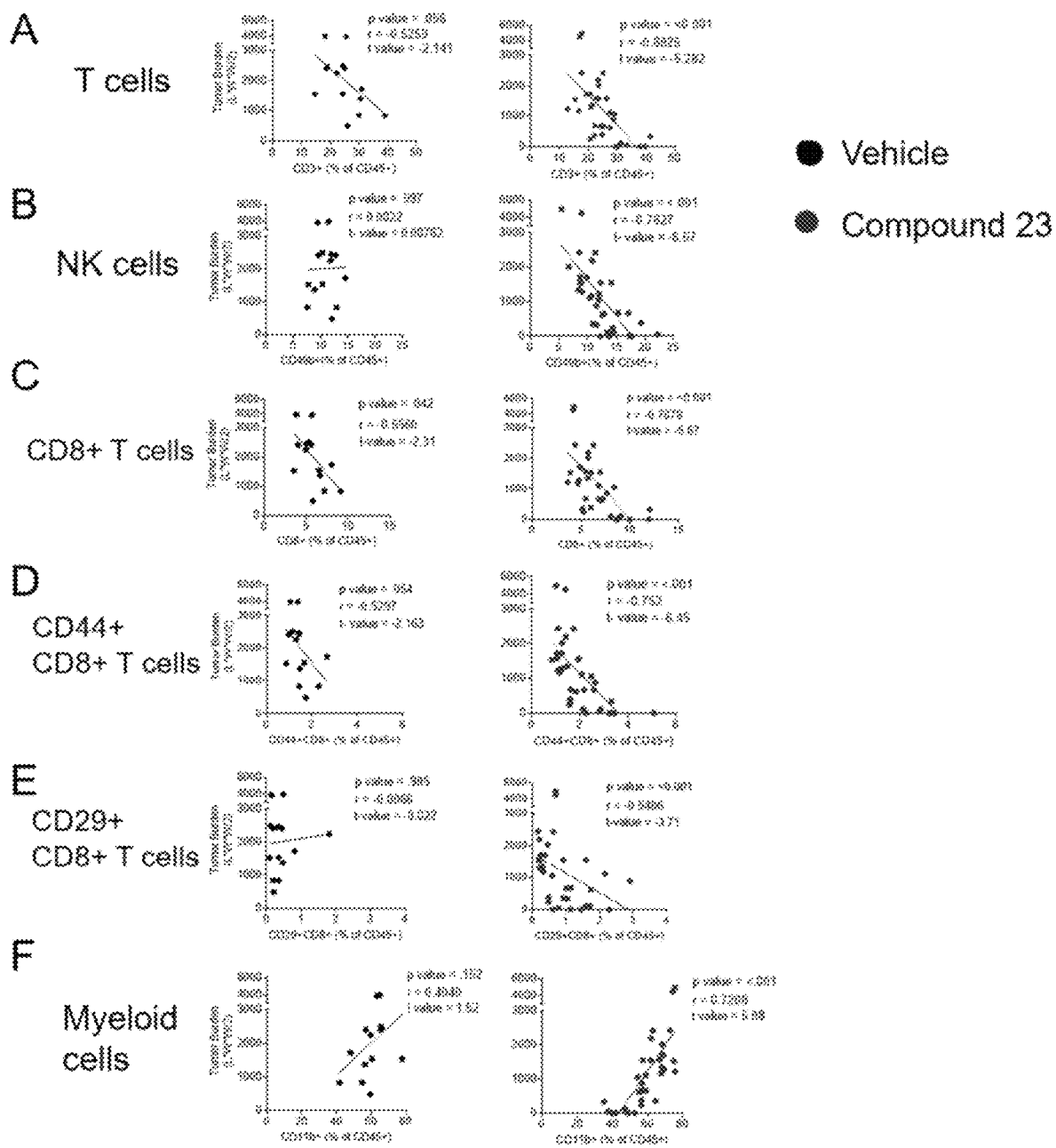
FIG. 9, panels 9A-9F, provide the strong correlation of antitumor activity of compound 23 with increased levels of circulating T and NK cells, CD8+ T-cells, and activated CD8+ T-cells, and decreased levels of circulating myeloid cells (CD11b+) in the blood of treated CT26-tumor-bearing mice.

In FIG. 9, mice bearing CT26 tumors on their left and right flanks were treated from Day 10 to Day 28 by administration of either vehicle (0.5% methylcellulose, 0.2% Polysorbate 80 in deionized water+1 eq HCl) daily or orally (PO) compound 23 at 30 mg/kg daily. CT26 tumors were harvested after 19 doses of compound 23 or vehicle and frequency and phenotype of immune cells was assessed in the blood by flow cytometry. Spearman correlation test was applied to calculate the correlation between levels of circulating immune cells and the tumor volume at d28.

Tumor regression in response to compound 23 treatments correlated strongly with elevated frequency of total circulating T-cells (FIG. 9A) and NK cells (FIG. 9B) in the blood of treated CT26-tumor-bearing mice. Similar positive correlations were observed between tumor volume and the frequency of circulating CD8+ T-cells (FIG. 9C) and activated CD8+ T-cells expressing the activation markers CD44 (FIG. 9D) and CD29 (FIG. 9E). In contrast, increased tumor growth inhibition correlated with decreased levels of circulating myeloid cells, characterized by the expression of the CD11b marker (FIG. 9F).

Example 5

This example provides assays and results for treating tumor models in vivo with combinations of Cbl-b compounds and checkpoint inhibitors as described herein. The two illustrative examples of a checkpoint inhibitor include an anti-CTLA-binding antagonist and an anti-LAG3 binding antagonist.

Figure 10A:
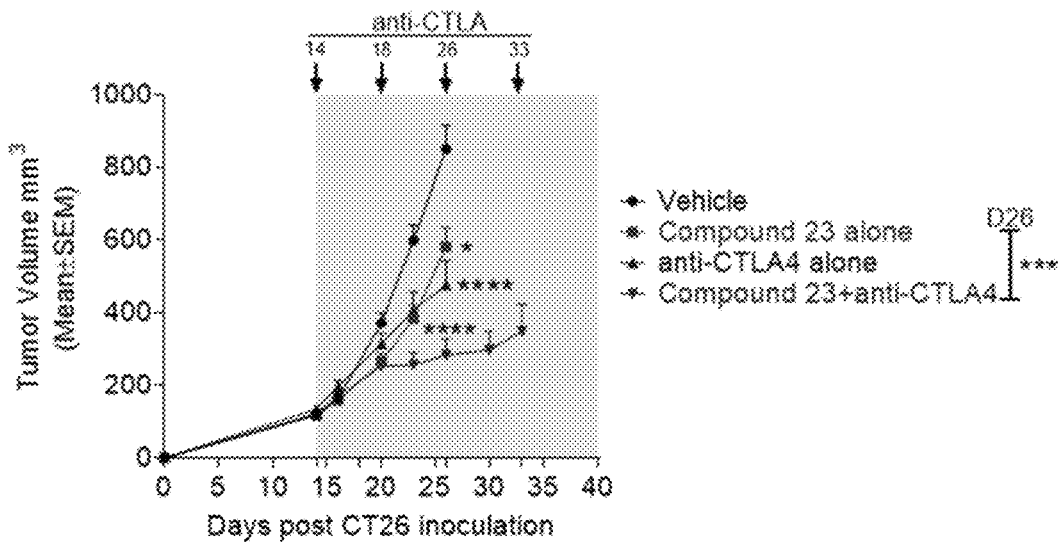
FIGS. 10A and 10B provide synergy of compound 23 and anti-CTLA-4 antibody in mice with CT26 tumors. The shaded areas depict the QD dosing of compound 23.
Figure 10B:
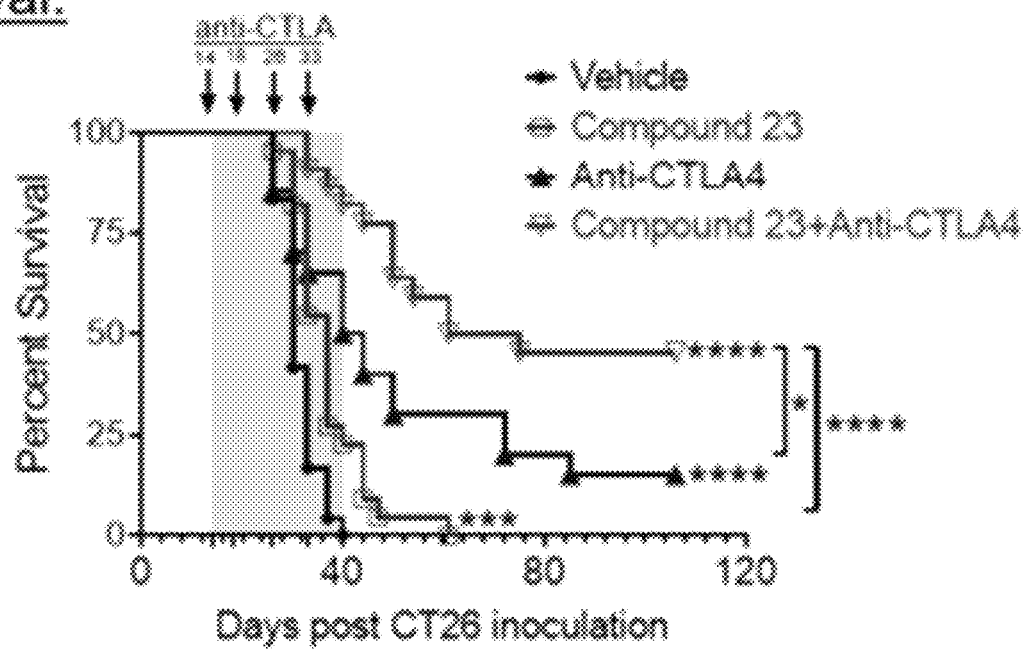

Mice bearing CT26 tumors on their left and right flanks were treated from Day 14 to Day 40 by administration of either: vehicle (0.5% methylcellulose, 0.2% Polysorbate 80 in deionized water+1 eq HCl) daily, orally (PO) compound 23 at 30 mg/kg daily, PO; anti-CTLA-4 antibody at 10 mg/kg (Day 14) and 5 mg/kg (Day 18, 26, 33) by intraperitoneal (IP) injection; or the combination of compound 23 and anti-CTLA-4 antibody. Beginning on Day 14, tumor volumes were measured twice weekly. FIG. 10A shows group mean tumor volumes±SEM, on Day 14 through 40. Statistical significance of differences in mean tumor volumes between groups was evaluated from Day 14 to Day 40 using repeated measure two-way ANOVA with Dunnett's multiple comparisons test (not significant (ns) P>0.05, *P≤0.05, P≤0.01, *P≤0.001, and **** P≤0.0001). FIG. 10B shows the percentage animals of surviving between Day 14 to 106 as defined by reaching the conditional survival endpoint of bearing a tumor with volume equal to or greater than 2000 mm$^3$, unless having previously met a humane endpoint.

Figure 11A:
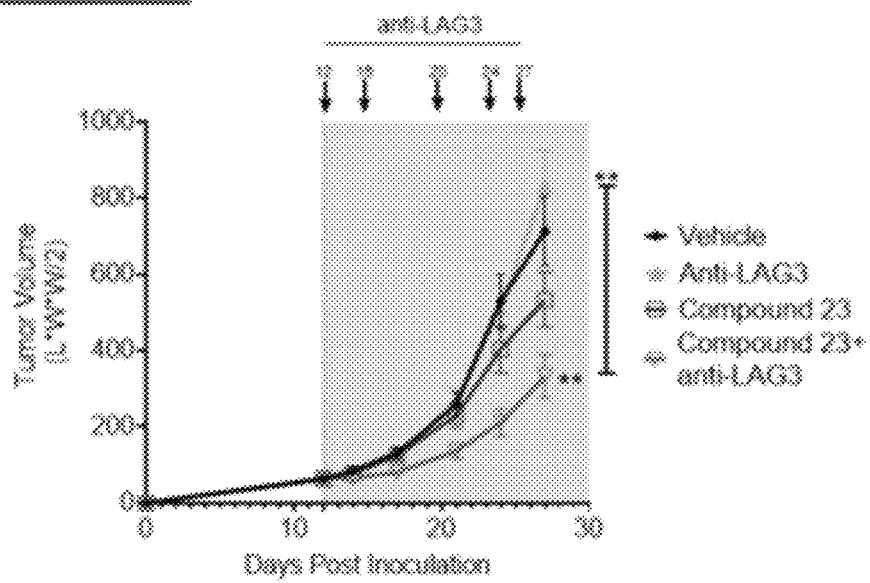
FIGS. 11A and 11B provide synergy of compound 23 and anti-LAG3 antibody in mice with CT26 tumors. The shaded areas depict the QD dosing of compound 23.
Figure 11B:
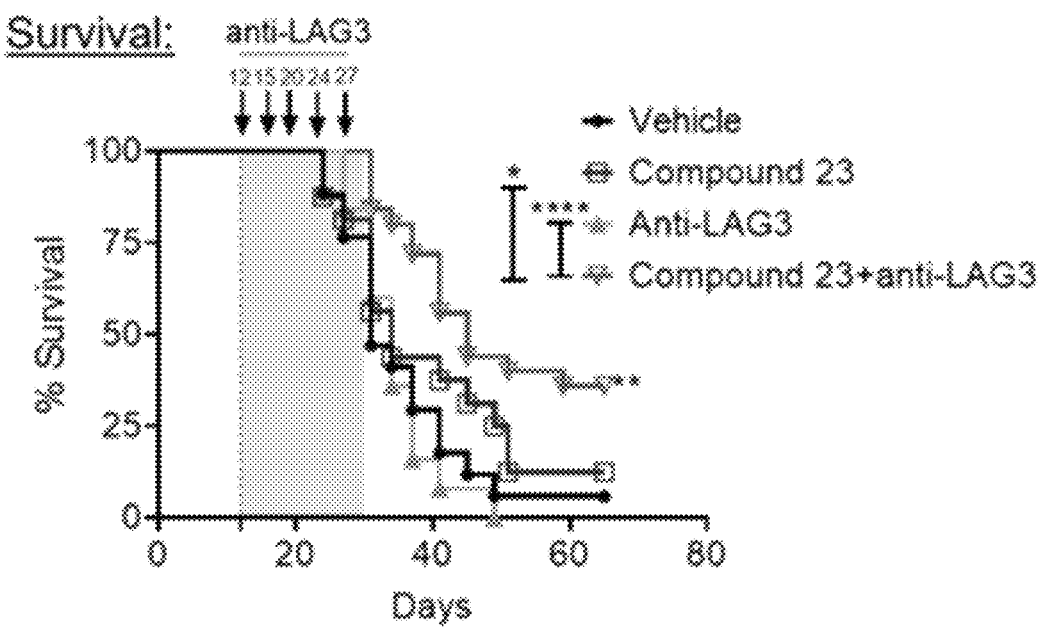

Mice bearing CT26 tumors on their left and right flanks were treated from Day 12 to Day 30 by administration of either: vehicle (0.5% methylcellulose, 0.2% Polysorbate 80 in deionized water+1 eq HCl) daily, orally (PO) compound 23 at 30 mg/kg daily, PO; anti-LAG3 antibody at 10 mg/kg on Day 12, 15, 20, 24, and 27 by intraperitoneal (IP)

injection; or the combination of compound 23 and anti-LAG3 antibody. Beginning on Day 12, tumor volumes were measured twice weekly. FIG. 11A shows group mean tumor volumes±SEM, on Day 12 through 30. Statistical significance of differences in mean tumor volumes between groups was evaluated from Day 10 to Day 30 using repeated measure two-way ANOVA with Dunnett's multiple comparisons test (not significant (ns) P>0.05, *P≤0.05, P≤0.01, *P≤0.001, and **** P≤0.0001). FIG. 11B shows the percentage animals of surviving between Day 12 to 65 as defined by reaching the conditional survival endpoint of bearing a tumor with volume equal to or greater than 2000 mm³, unless having previously met a humane endpoint.

Example 6

This example provides assays and results for treating tumor models in vivo with combinations of Cbl-b compounds and a macrophage checkpoint inhibitor.

Mice bearing A20 tumors on their flank were treated by administration of either: vehicle (0.5% methylcellulose, 0.2% Polysorbate 80 in deionized water+1 eq HCl) daily, orally (PO) compound 23 at 30 mg/kg daily, PO; anti-CD47 antibody by intraperitoneal (IP) injection; or the combination of compound 23 and anti-CD47 antibody. Tumor volumes were measured twice weekly. Statistical significance of differences in mean tumor volumes between groups were evaluated using repeated measure two-way ANOVA with Dunnett's multiple comparisons test (not significant (ns) P>0.05, *P<0.05, P<0.01, *P<0.001, and **** P≤0.0001). The percentage animals of surviving between the relevant time points was defined by reaching the conditional survival endpoint of bearing a tumor with volume equal to or greater than 2000 mm³, unless having previously met a humane endpoint.

Example 7

This example provides assays and results for treating tumor models in vivo with combinations of Cbl-b compounds and an ADCC triggering agent.

Figure 12A:
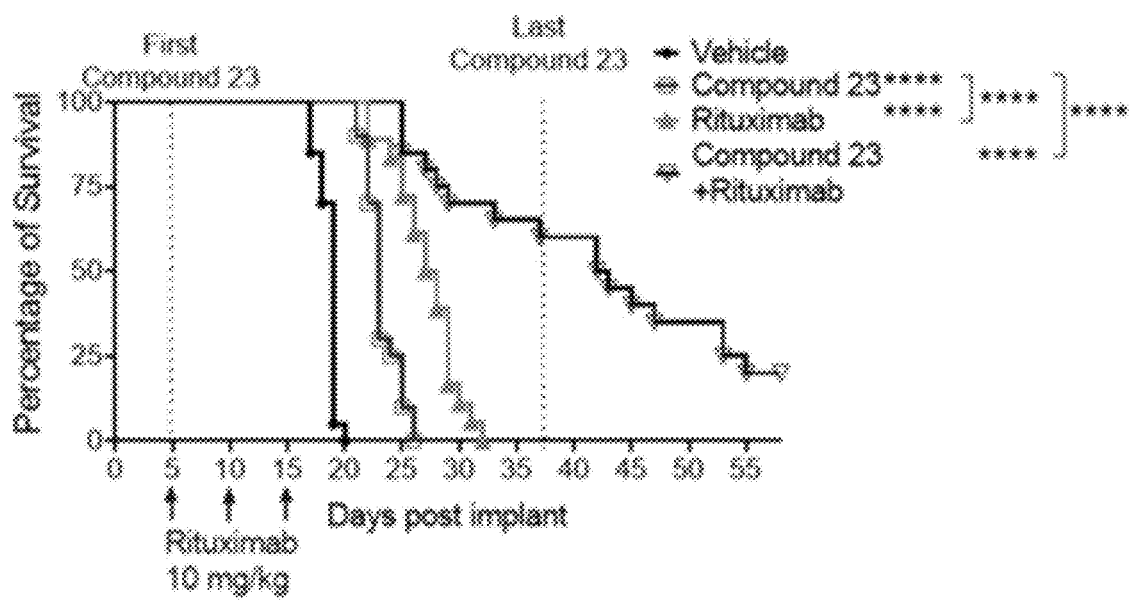
FIG. 12, panels 12A and 12B provide the enhanced effects of compound 23 and anti-CD20 antibody in a human non-Hodgkin's lymphoma animal model and that the effect of the anti-CD20 antibody is primarily mediated by NK cells.

Female CB17 mice with severe combined immunodeficiency (SCID) were intravenously (IV) injected in the tail vein with Raji cells on Day 0 and treated from Day 5 to Day 37 by administration of either: vehicle (0.5% methylcellulose, 0.2% Polysorbate 80 in deionized water+1 eq HCl) daily, orally (PO) or compound 23 at 30 mg/kg daily, PO. Anti-CD20 antibody (rituximab) at 20 mg/kg was intraperitoneally (IP) administered on Day 5, 10, and 15, either alone or in combination with compound 23 at 30 mg/kg daily, PO. In SCID-Beige mice, Raji tumors have a primary tropism for the bone marrow and untreated mice reliably develop hind-limb paralysis at 3-5 weeks as a consequence of spinal cord compression by tumor expanding from vertebral bodies. Mice that developed hind-limb paralysis over time were killed and percentage of surviving animals between Day 5 to 58 was plotted and the results are shown in FIG. 12A. Survival of mice treated with compound 23 alone or rituximab alone was significantly higher (p<0.0001) when compared to untreated mice, but significantly lower when compared to mice treated with the combination of compound 23 and rituximab (p<0.0001).

In another experiment, female CB17 mice with severe combined immunodeficiency (SCID) were intravenously (IV) injected in the tail vein with Raji cells on Day 0 and treated from Day 5 to Day 37 by administration of either: vehicle (0.5% methylcellulose, 0.2% Polysorbate 80 in deionized water+1 eq HCl) daily, orally (PO); compound 23 at 30 mg/kg daily, PO; or the combination of compound 23 at 30 mg/kg daily, PO and rituximab at 20 mg/kg administered on Day 5, 10, and 15 by IP injection. Three additional groups of mice were treated in the presence of depleting antibodies for NK cells (anti-asialo-GM1).

Figure 12B:
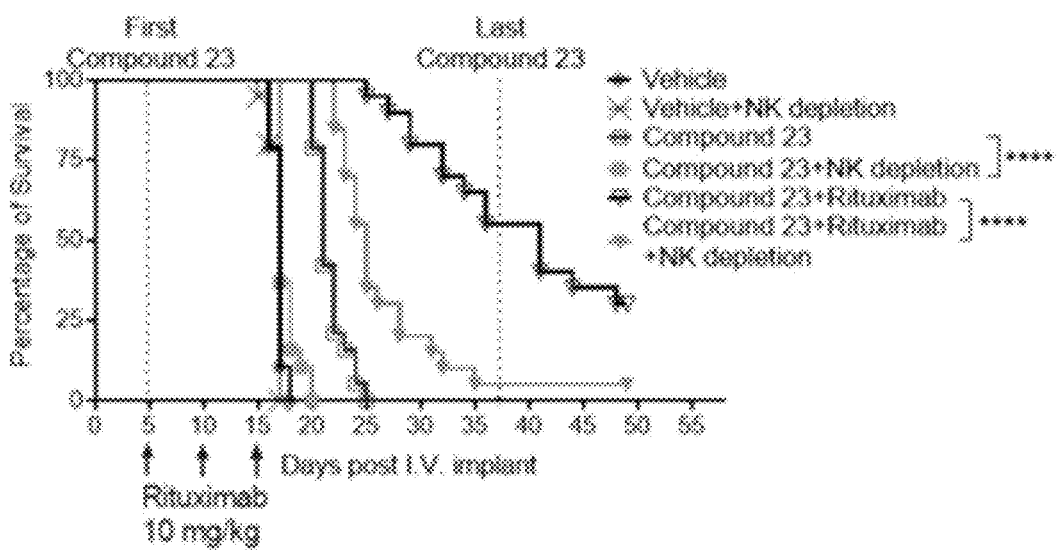

In SCID-Beige mice, Raji tumors have a primary tropism for the bone marrow and untreated mice reliably develop hind-limb paralysis at 3-5 weeks as a consequence of spinal cord compression by tumor expanding from vertebral bodies. Mice that developed hind-limb paralysis over time were killed and percentage of surviving animals between Day 5 to 58 was plotted and shown in FIG. 12B. As it can be seen, NK cell depletion abrogates compound 23 activity (p<0.0001) and partially abrogate the activity of the combination of compound 23 and rituximab (p<0.0001).

Example 8

This example provides assays and results for treating tumor models in vitro with combinations of Cbl-b compounds and a PARP inhibitor.

BT549 (BRCA wild type) (A) and DoTc 4510 (BRCA2 mutated) (B) cells were seeded in duplicate into tissue culture treated black-sided, clear-bottom 96-well plates at $5,000^{cells}/_{well}$ and allowed to adhere and establish for 24 h. Cells were treated with indicated concentrations of DMSO, compound 23, or Olaparib (FIGS. 13A and 13B) either alone or in combination and were labelled with 1× Essen Bioscience IncuCyte® Caspase-3/7 Green Reagent (final concentration 5 µM). Treated plates were imaged every 2 hours for 72 hours with the IncuCyte® S3 Live-Cell Analysis System. At each timepoint, one image per well was taken in both brightfield and FITC channels on the IncuCyte® S3 Live-Cell Analysis System. Images were analyzed for number of green objects per mm² using the IncuCyte S3 v2017A software.

Figure 13:
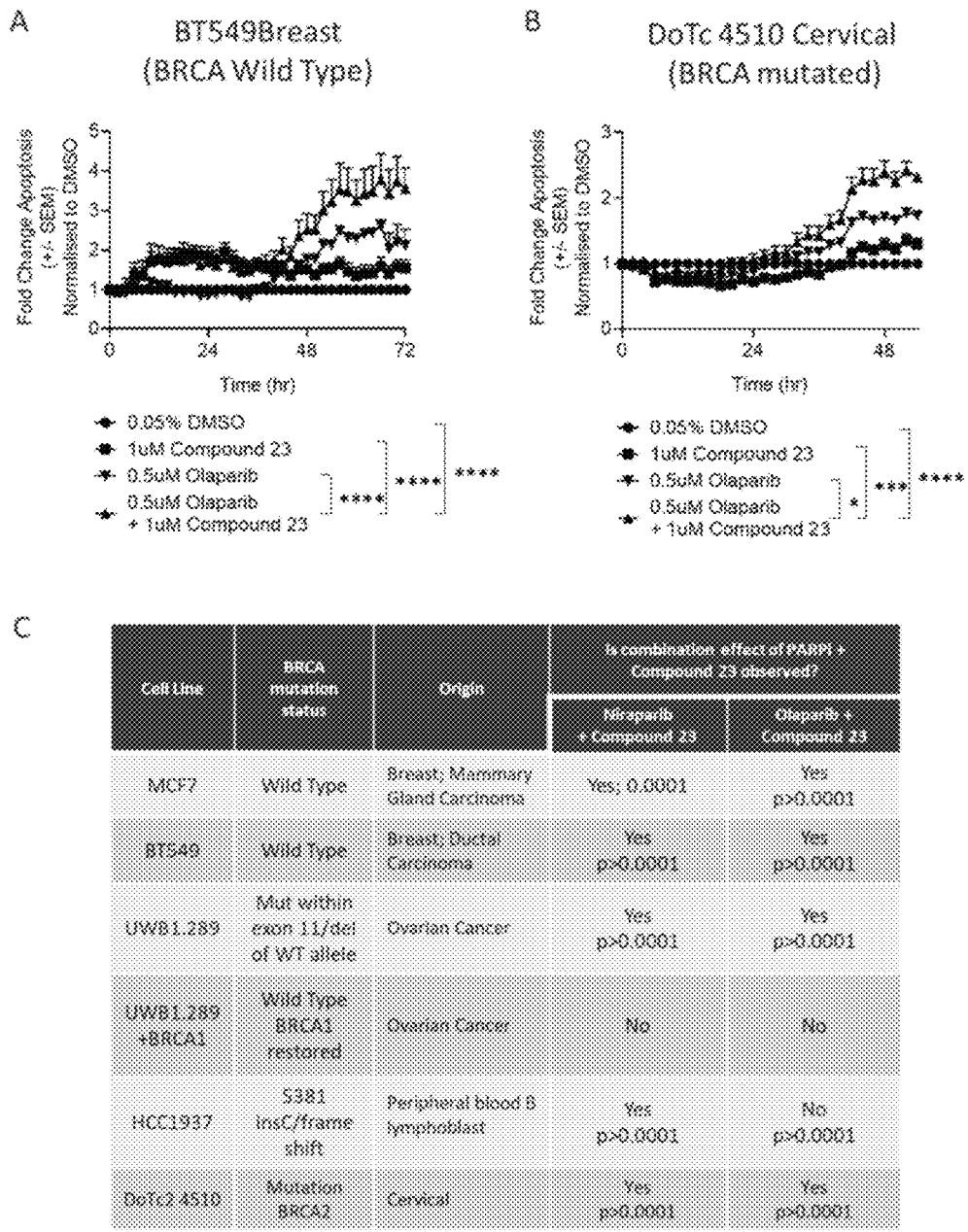
FIG. 13, panels 13A-13C provide the enhanced effects of compound 23 and a PARP inhibitor in BRCA wild type and BRCA mutated tumor cell lines.

Using a caspase 3/7 apoptosis Incucyte assay, the effect of compound 23, PARPi and the combination of compound 23, and PARPi on tumor cell apoptosis was assessed in both BRCA wild type and mutated tumor cell lines in vitro. BT549 tumor cells (BRCA wild type) treated with 1 µM compound 23 or 0.05 µM olaparib alone did not undergo a significant increase in apoptosis, compared to the 0.05% DMSO control. However, a significant increase in the number of tumor cells undergoing apoptosis was observed in response to the combination of compound 23 and olaparib compared to either DMSO control (p<0.0001), compound 23 alone (p<0.0001), or olaparib alone (p<0.0001) (FIG. 13A).

DoTc 4510 tumor cells (uterus tissue that is mutant for BRCA2) treated with compound 23 or olaparib alone did not significantly increase tumor cell apoptosis, compared to the 0.05% DMSO control. However, a significant increase in the number of tumor cells undergoing apoptosis was observed in response to the combination of compound 23 and olaparib compared to either DMSO control (p<0.0001), compound 23 alone (p<0.0001), or olaparib alone (p<0.0001) (FIG. 13B).

The caspase 3/7 tumor cell apoptosis assay was used to assess tumor cell apoptosis in response to compound 23 either alone or in combination with PARPi in multiple cell lines: The caspase 3/7 tumor cell apoptosis assay was used to assess tumor cell apoptosis in response to compound 23 and PARPi alone or in combination in multiple cell lines: MCF-7 (BRCA wild type), UWB1.289 (a BRCA 1-null human ovarian cancer line), UWB1.289 BRCA+ (a BRCA 1-null human ovarian cancer line, in which wild-type BRCA1 was restored), HCC1937 (a cell line that synthesizes a truncated BRCA1 protein that is the product of a disease-producing mutant allele (5382insC) and no wild-type protein, and the DoTc 4510 cell line (uterus tissue that is mutant for BRCA2). All cell lines tested showed an increase in the number of tumor cells undergoing apoptosis after the combination treatment of compound 23 and PARPi compared to compound 23, PARPi or 0.05% DMSO alone (FIG. 13C).

Example 9

This example provides assays and results for treating tumor models in vitro with combinations of Cbl-b compounds and a taxane.

BT549 cells were seeded in duplicate into tissue culture treated black-sided, clear-bottom 96-well plates at 5,000 $^{cells}/_{well}$ and allowed to adhere and establish for 24 h. Cells were treated with DMSO, compound 23, or Paclitaxel either alone or in combination and were labelled with 1× Essen Bioscience IncuCyte® Caspase-3/7 Green Reagent (final concentration 5 µM). Treated plates were imaged every 2 hours for 48 hours with the IncuCyte® S3 Live-Cell Analysis System. At each timepoint, one image per well was taken in both brightfield and FITC channels on the IncuCyte® S3 Live-Cell Analysis System. Images were analyzed for number of green objects per $mm^2$ using the IncuCyte S3 v2017A software.

Figure 14:
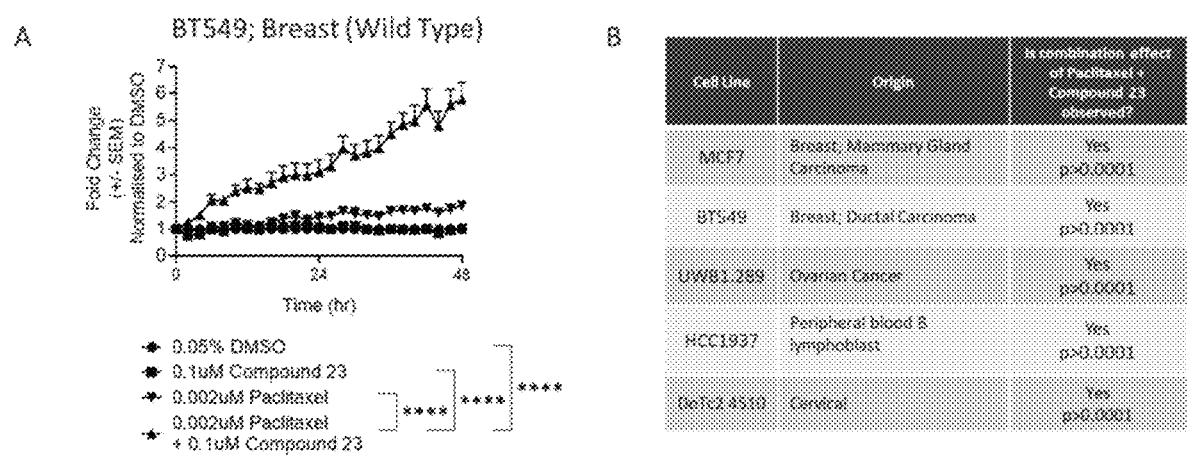
FIG. 14, panels 14A and 14B provide the enhanced effects of compound 23 and a taxane in tumor cells.

Using a caspase 3/7 apoptosis Incucyte® assay, the effect of compound 23, paclitaxel and the combination of compound 23 and paclitaxel on tumor cell apoptosis was assessed in the BT549 tumor cell line (a mammary gland carcinoma) in vitro. BT549 cells treated with 0.1 µM compound 23 or 0.002 µM paclitaxel alone did not undergo a significant increase in apoptosis, compared to the 0.05% DMSO control. However, a significant increase in the number of tumor cells undergoing apoptosis was observed in response to the combination of compound 23 and paclitaxel compared to either DMSO control ($p<0.0001$), compound 23 alone ($p<0.0001$), or paclitaxel alone ($p<0.0001$) (FIG. 14A).

The caspase 3/7 tumor cell apoptosis assay was used to assess tumor cell apoptosis in response to compound 23 alone or in combination with paclitaxel in multiple cell lines: MCF-7 (mammary gland carcinoma), UWB1.289 (ovarian cancer), HCC1937 (peripheral blood B lymphoblast), and DoTc 4510 (cervical cancer). All cell lines tested showed an increase in the number of tumor cells undergoing apoptosis after the combination treatment of compound 23 and paclitaxel compared to compound 23, paclitaxel or 0.05% DMSO alone (FIG. 14B).

Example 10

This example provides assays and results for treating tumor in vivo with combinations of Cbl-b compounds and an anti-TIGIT antibody.

Figure 15:
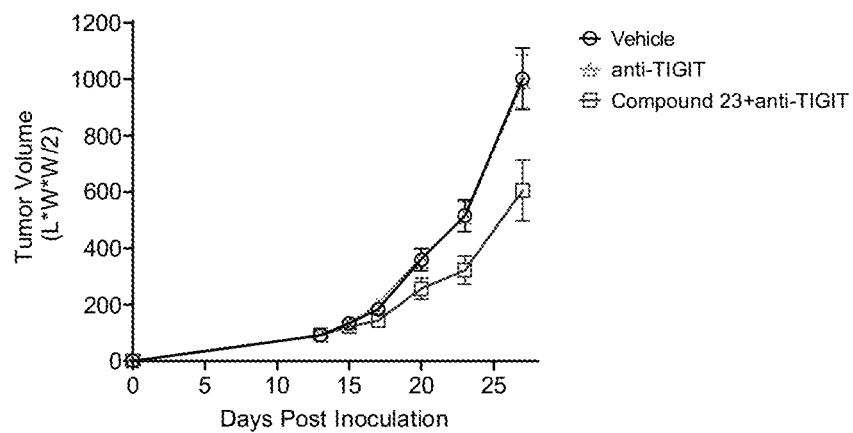
FIG. 15, panels 15A and 15B provide the enhanced effects of compound 23 and an anti-TIGIT antibody.
Figure 15:
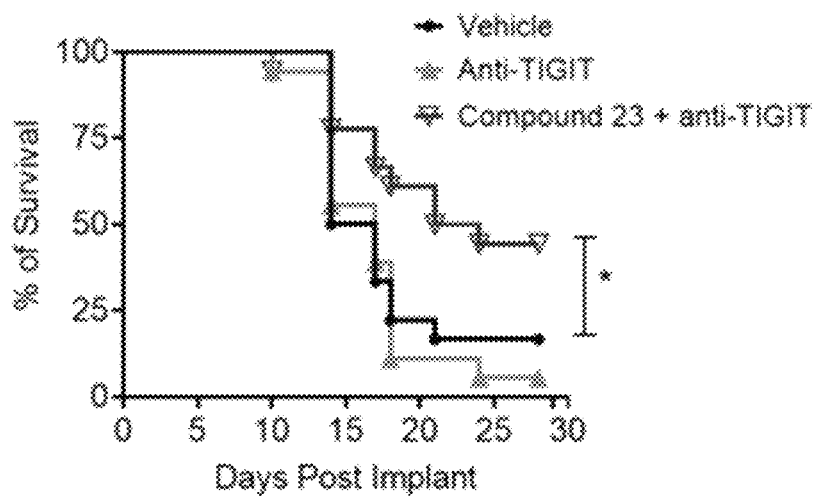

Mice bearing CT26 tumors on their left and right flanks were treated from Day 13 post implantation by administration of either: vehicle (0.5% methylcellulose, 0.2% Polysorbate 80 in deionized water+1 eq HCl) daily, orally (PO) Compound 23 at 30 mg/kg daily, PO; anti-TIGIT antibody at 10 mg/kg BioXcell Clone 1G9 (Day 13, 16 20 24) by intraperitoneal (IP) injection; or the combination of Compound 23 and anti-TIGIT antibody. Beginning Day 13, tumor volumes were measured twice weekly. Bottom graph shows the percentage animals surviving to day 30 as defined by reaching the conditional survival endpoint of bearing a tumor with volume equal to or greater than 2000 mm3, unless having previously met a humane endpoint. Statistical significance of differences in survival was calculated using Log-rank (Mantel-Cox) test (FIG. 15B).

EQUIVALENTS

The disclosure set forth above may encompass multiple distinct embodiments with independent utility. Although each of these embodiments has been disclosed in a certain form(s), the specific embodiments thereof as disclosed and illustrated herein are not to be considered in a limiting sense, because numerous variations are possible. The subject matter of this disclosure includes all novel and nonobvious combinations and subcombinations of the various elements, features, functions, and/or properties disclosed herein. The following claims particularly point out certain combinations and subcombinations regarded as novel and nonobvious. Embodiments in other combinations and subcombinations of features, functions, elements, and/or properties may be claimed in this application, in applications claiming priority from this application, or in related applications. Such claims, whether directed to a different embodiment or to the same embodiment, and whether broader, narrower, equal, or different in scope in comparison to the original claims, also are regarded as included within the subject matter of the present disclosure.

One or more features from any embodiments described herein or in the figures may be combined with one or more features of any other embodiments described herein or in the figures without departing from the scope of this disclosure.

All publications, patents, and patent applications cited in this specification are herein incorporated by reference as if each individual publication, patent, or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed is:

1. A method of treating colon cancer or colorectal cancer or breast cancer in a subject in need thereof, comprising administering to the subject
   (a) 0.1 mg to 50 mg of a Cbl-b inhibitor compound of the following formula;

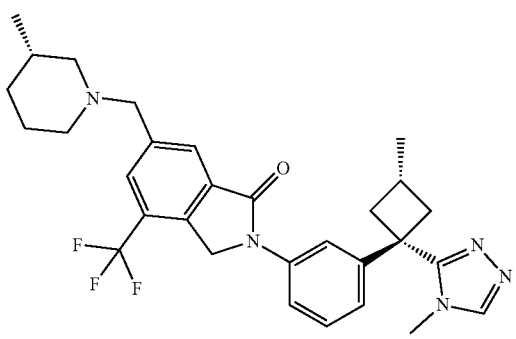 [SMILES: C[C@H]1CCCN(Cc2cc3c(c(C(F)(F)F)c2)CN(c2cccc([C@]4(c5nncn5C)C[C@@H](C)C4)c2)C3=O)C1]

and (b) one or more checkpoint inhibitors selected from a group consisting of anti-PD-1 antibodies, anti-CTLA4 antibodies or LAG3 antibodies.

2. The method of claim 1 wherein the anti-PD1 antibody is Pembrolizumab.

3. The method of claim 1 wherein the anti-PD1 antibody is nivolumab.

4. The method of claim 1 wherein the anti-PD1 antibody is cemiplimab.

* * * * *